(12) United States Patent
Alizoti et al.

(10) Patent No.: US 11,975,140 B2
(45) Date of Patent: May 7, 2024

(54) MEDICATION DELIVERY SYSTEM WITH MASK

(71) Applicant: Trudell Medical International, London (CA)

(72) Inventors: Neritan Alizoti, London (CA); Stephen Costella, London (CA); Daniel Engelbreth, London (CA); Noel Gulka, London (CA); Alanna Kirchner, London (CA); Adam Meyer, London (CA); Robert Morton, London (CA); Bart Nowak, London (CA); Greg Romanczuk, London (CA); Ronak Sakaria, London (CA)

(73) Assignee: TRUDELL MEDICAL INTERNATIONAL, London (CA)

( * ) Notice: Subject to any disclaimer, the term of this patent is extended or adjusted under 35 U.S.C. 154(b) by 378 days.

(21) Appl. No.: 17/098,933

(22) Filed: Nov. 16, 2020

(65) Prior Publication Data
US 2021/0170119 A1 Jun. 10, 2021

Related U.S. Application Data

(63) Continuation of application No. 15/600,039, filed on May 19, 2017, now Pat. No. 10,850,050.
(Continued)

(51) Int. Cl.
*A61M 15/00* (2006.01)
*A61B 5/00* (2006.01)
(Continued)

(52) U.S. Cl.
CPC ........... *A61M 15/002* (2014.02); *A61B 5/087* (2013.01); *A61B 5/4833* (2013.01);
(Continued)

(58) Field of Classification Search
CPC ............ A61M 15/002; A61M 15/0021; A61M 15/00; A61M 15/0013; A61M 15/0015;
(Continued)

(56) References Cited

U.S. PATENT DOCUMENTS 2,535,844 A 12/1950 Emerson
2,882,026 A 4/1959 Eichelman
(Continued)

FOREIGN PATENT DOCUMENTS

AU B-29969/89 8/1990
CA 2 607 458 A1 11/2006
(Continued)

OTHER PUBLICATIONS

Written Opinion of the International Searching Authority in International Application No. PCT/IB2017/052968 dated Sep. 5, 2017, 10 pages.
(Continued)

*Primary Examiner* — Kevin C Sirmons
*Assistant Examiner* — Alexandra Lalonde
(74) *Attorney, Agent, or Firm* — Crowell & Moring LLP

(57) ABSTRACT

A medication delivery system having a holding chamber capable of delivering dosages of medicament from a metered dose inhaler. The holding chamber includes an actuator detector, a flow detector, and a display. In another embodiment, a medication delivery system includes a holding chamber having an input end and an output end, a metered dose inhaler operably coupled to the input end of the holding chamber, and a metered dose inhaler identifier associated with the holding chamber and operable to identify the metered dose inhaler coupled to the holding chamber.

25 Claims, 48 Drawing Sheets

Related U.S. Application Data

(60) Provisional application No. 62/366,327, filed on Jul. 25, 2016, provisional application No. 62/338,798, filed on May 19, 2016.

(51) Int. Cl.
*A61B 5/087* (2006.01)
*A61M 39/22* (2006.01)
*A61M 16/00* (2006.01)
*A61M 16/16* (2006.01)
*A61M 39/24* (2006.01)

(52) U.S. Cl.
CPC ........ *A61M 15/0086* (2013.01); *A61M 39/22* (2013.01); *A61B 2562/08* (2013.01); *A61M 15/0021* (2014.02); *A61M 15/009* (2013.01); *A61M 2016/0039* (2013.01); *A61M 16/161* (2014.02); *A61M 2039/2433* (2013.01); *A61M 2205/0283* (2013.01); *A61M 2205/332* (2013.01); *A61M 2205/3334* (2013.01); *A61M 2205/3368* (2013.01); *A61M 2205/3375* (2013.01); *A61M 2205/3553* (2013.01); *A61M 2205/3584* (2013.01); *A61M 2205/3592* (2013.01); *A61M 2205/50* (2013.01); *A61M 2205/502* (2013.01); *A61M 2205/581* (2013.01); *A61M 2205/582* (2013.01); *A61M 2205/583* (2013.01); *A61M 2205/6009* (2013.01); *A61M 2205/6054* (2013.01); *A61M 2205/6081* (2013.01); *A61M 2205/8206* (2013.01); *A61M 2205/825* (2013.01); *A61M 2230/432* (2013.01)

(58) Field of Classification Search
CPC .......... A61M 15/0016; A61M 15/0018; A61M 15/0091; A61M 15/0096; A61M 15/0001; A61M 15/009; A61M 2205/332; A61M 2205/33; A61M 2205/58; A61M 2205/581; A61M 2205/582; A61M 2205/583; A61M 2205/14; A61M 2205/43; A61M 2205/44; A61M 2205/13; A61M 16/06; A61M 2016/0039; A61M 15/0093; A61M 15/0095; A61M 15/0098; A61M 15/0065; A61M 15/0086; A61M 2205/0283; A61M 2205/3327; A61M 2205/3331; A61M 2205/3344; A61M 2205/3368; A61M 2205/3375; A61M 2205/50; A61M 2205/502; A61M 2205/8206; A61M 2205/82; A61M 2205/076; A61M 16/00; A61M 16/0003; A61M 16/161; A61M 16/16; A61M 16/20; A61M 16/201; A61M 16/202; A61M 16/1065; A61M 16/107; A61M 16/208; A61M 16/204; A61M 16/205; A61M 2016/003; A61M 2025/022; A61M 35/00; A61M 35/10; A61M 39/22; A61M 39/24; A61M 2039/242; A61M 2039/2433; A61M 2039/244; A61M 2039/2446; A61M 2039/246; A61M 2039/2466; A61M 2210/0625; A61M 2205/3334; A61M 2205/587; A61J 1/00; A61J 7/0053; A61J 7/00; A61J 15/0003; A61J 15/00
See application file for complete search history.

(56) References Cited

U.S. PATENT DOCUMENTS

| | | |
|---|---|---|
| 2,951,644 A | 9/1960 | Mahon et al. |
| 3,172,406 A | 3/1965 | Bird et al. |
| 3,269,665 A | 8/1966 | Cheney |
| 3,467,092 A | 9/1969 | Bird et al. |
| 3,490,697 A | 1/1970 | Best, Jr. |
| 3,580,249 A | 5/1971 | Takaoka |
| 3,584,621 A | 6/1971 | Bird et al. |
| 3,630,196 A | 12/1971 | Bird et al. |
| 3,658,059 A | 4/1972 | Steil |
| 3,664,337 A | 5/1972 | Lindsey et al. |
| 3,826,255 A | 7/1974 | Havstad et al. |
| 3,838,686 A | 10/1974 | Szekely |
| 3,874,379 A | 4/1975 | Enfield et al. |
| 3,896,101 A | 7/1975 | McIntosh et al. |
| 3,903,884 A | 9/1975 | Huston et al. |
| 3,990,442 A | 11/1976 | Patneau |
| 4,093,124 A | 6/1978 | Morane et al. |
| 4,094,317 A | 6/1978 | Wasnich |
| 4,106,503 A | 8/1978 | Rosenthal et al. |
| 4,116,387 A | 9/1978 | Kremer, Jr. et al. |
| 4,139,128 A | 2/1979 | Ewald |
| 4,150,071 A | 4/1979 | Pecina |
| 4,183,361 A | 1/1980 | Russo |
| 4,198,969 A | 4/1980 | Virag |
| 4,206,644 A | 6/1980 | Platt |
| 4,210,140 A | 7/1980 | James et al. |
| 4,210,155 A | 7/1980 | Grimes |
| 4,251,033 A | 2/1981 | Rich et al. |
| 4,253,468 A | 3/1981 | Lehmbeck |
| 4,268,460 A | 5/1981 | Boiarski et al. |
| 4,291,688 A | 9/1981 | Kistler |
| 4,333,450 A | 6/1982 | Lester |
| 4,413,784 A | 11/1983 | Dea |
| 4,452,239 A | 6/1984 | Malem |
| 4,456,179 A | 6/1984 | Kremer |
| 4,470,412 A | 9/1984 | Nowacki et al. |
| 4,484,577 A | 11/1984 | Sackner et al. |
| 4,508,118 A | 4/1985 | Toth |
| 4,509,515 A | 4/1985 | Altounyan et al. |
| 4,509,688 A | 4/1985 | Gagne et al. |
| 4,588,129 A | 5/1986 | Shanks |
| 4,620,670 A | 11/1986 | Hughes |
| 4,622,968 A | 11/1986 | Persson |
| 4,627,432 A | 12/1986 | Newell et al. |
| 4,657,007 A | 4/1987 | Carlin et al. |
| 4,674,491 A | 6/1987 | Brugger et al. |
| 4,677,975 A | 7/1987 | Edgar et al. |
| 4,746,067 A | 5/1988 | Svoboda |
| 4,758,224 A | 7/1988 | Siposs |
| 4,792,097 A | 12/1988 | Kremer, Jr. et al. |
| 4,809,692 A | 3/1989 | Nowacki et al. |
| 4,832,015 A | 5/1989 | Nowacki et al. |
| 4,911,157 A | 3/1990 | Miller |
| 4,984,158 A | 1/1991 | Hillsman |
| 5,012,803 A | 5/1991 | Foley et al. |
| 5,012,804 A | 5/1991 | Foley et al. |
| 5,020,527 A | 6/1991 | Dessertine |
| 5,020,530 A | 6/1991 | Hillsman |
| 5,042,467 A | 8/1991 | Foley |
| 5,054,477 A | 10/1991 | Terada et al. |
| 5,054,478 A | 10/1991 | Grychowski et al. |
| 5,078,131 A | 1/1992 | Foley |
| 5,086,765 A | 2/1992 | Levine |
| 5,165,392 A | 11/1992 | Small |
| 5,167,506 A | 12/1992 | Kilis et al. |
| 5,170,782 A | 12/1992 | Kocinski |
| 5,241,954 A | 9/1993 | Glenn |
| 5,277,175 A | 1/1994 | Riggs et al. |
| 5,280,784 A | 1/1994 | Kohler |
| 5,284,133 A | 2/1994 | Burns et al. |
| 5,299,565 A | 4/1994 | Brown |
| 5,301,662 A | 4/1994 | Bagwell et al. |
| 5,301,663 A | 4/1994 | Small, Jr. |
| 5,309,900 A | 5/1994 | Knoch et al. |
| 5,312,046 A | 5/1994 | Knoch et al. |

(56) References Cited

U.S. PATENT DOCUMENTS

| | | |
|---|---|---|
| 5,312,281 A | 5/1994 | Takahashi et al. |
| 5,318,015 A | 6/1994 | Mansson et al. |
| 5,331,953 A | 7/1994 | Andersson et al. |
| 5,333,106 A | 7/1994 | Lanpher et al. |
| 5,337,926 A | 8/1994 | Drobish et al. |
| 5,349,947 A | 9/1994 | Newhouse et al. |
| 5,363,842 A | 11/1994 | Mishelevich et al. |
| 5,383,470 A | 1/1995 | Kolbly |
| 5,385,140 A | 1/1995 | Smith |
| 5,392,648 A | 2/1995 | Robertson |
| 5,398,714 A | 3/1995 | Price |
| 5,427,089 A | 6/1995 | Kraemer |
| 5,431,154 A | 7/1995 | Seigel et al. |
| 5,458,136 A | 10/1995 | Jaser et al. |
| 5,461,695 A | 10/1995 | Knoch |
| 5,477,849 A | 12/1995 | Fry |
| 5,479,920 A | 1/1996 | Piper et al. |
| 5,487,378 A | 1/1996 | Robertson et al. |
| 5,497,765 A | 3/1996 | Praud et al. |
| 5,505,192 A | 4/1996 | Samiotes et al. |
| 5,505,193 A | 4/1996 | Ballini et al. |
| 5,505,195 A | 4/1996 | Wolf et al. |
| 5,511,538 A | 4/1996 | Haber et al. |
| 5,511,539 A | 4/1996 | Lien |
| 5,515,842 A | 5/1996 | Ramseyer et al. |
| 5,520,166 A | 5/1996 | Ritson et al. |
| 5,522,380 A | 6/1996 | Dwork |
| 5,533,497 A | 7/1996 | Ryder |
| 5,533,501 A | 7/1996 | Denyer |
| 5,544,647 A | 8/1996 | Jewett et al. |
| 5,549,102 A | 8/1996 | Lintl et al. |
| 5,570,682 A | 11/1996 | Johnson |
| 5,582,162 A | 12/1996 | Petersson |
| 5,584,285 A | 12/1996 | Salter et al. |
| 5,598,839 A | 2/1997 | Niles et al. |
| 5,613,489 A | 3/1997 | Miller et al. |
| 5,617,844 A | 4/1997 | King |
| 5,622,162 A | 4/1997 | Johansson et al. |
| 5,630,409 A | 5/1997 | Bono et al. |
| 5,645,049 A | 7/1997 | Foley et al. |
| 5,687,912 A | 11/1997 | Denyer |
| 5,701,886 A | 12/1997 | Ryatt |
| 5,704,344 A | 1/1998 | Cole |
| 5,740,793 A | 4/1998 | Hodson et al. |
| 5,752,505 A | 5/1998 | Ohki et al. |
| 5,758,638 A | 6/1998 | Kreamer |
| 5,765,553 A | 6/1998 | Richards et al. |
| 5,792,057 A | 8/1998 | Rubsamen et al. |
| 5,794,612 A | 8/1998 | Wachter et al. |
| 5,803,078 A | 9/1998 | Brauner |
| 5,809,997 A | 9/1998 | Wolf |
| 5,816,240 A | 10/1998 | Komesaroff |
| 5,819,726 A | 10/1998 | Rubsamen et al. |
| 5,823,179 A | 10/1998 | Grychowski et al. |
| 5,848,588 A | 12/1998 | Foley et al. |
| 5,865,172 A | 2/1999 | Butler et al. |
| 5,875,774 A | 3/1999 | Clementi et al. |
| 5,881,718 A | 3/1999 | Mortensen et al. |
| 5,899,201 A | 5/1999 | Schultz et al. |
| 5,937,852 A | 8/1999 | Butler et al. |
| 5,954,049 A | 9/1999 | Foley et al. |
| 5,988,160 A | 11/1999 | Foley et al. |
| 6,026,807 A | 2/2000 | Puderbaugh et al. |
| 6,039,042 A | 3/2000 | Sladek |
| 6,033,841 A | 4/2000 | Verdun et al. |
| 6,044,841 A | 4/2000 | Verdum et al. |
| 6,073,628 A | 6/2000 | Butler et al. |
| 6,089,225 A | 7/2000 | Brown et al. |
| 6,116,233 A | 9/2000 | Denyer et al. |
| 6,116,239 A | 9/2000 | Volgyesi |
| 6,129,080 A | 10/2000 | Pitcher et al. |
| 6,131,568 A | 10/2000 | Denyer et al. |
| 6,138,669 A | 10/2000 | Rocci, Jr. et al. |
| 6,148,815 A | 11/2000 | Wolf |
| 6,176,237 B1 | 1/2001 | Wunderlich et al. |
| 6,179,164 B1 | 1/2001 | Fuchs |
| 6,192,876 B1 | 2/2001 | Denyer et al. |
| 6,202,642 B1 | 3/2001 | McKinnon et al. |
| 6,223,745 B1 | 5/2001 | Hammarlund et al. |
| 6,234,167 B1 | 5/2001 | Cox et al. |
| 6,237,589 B1 | 5/2001 | Denyer et al. |
| 6,253,767 B1 | 7/2001 | Mantz |
| 6,293,279 B1 | 9/2001 | Schmidt et al. |
| 6,338,443 B1 | 1/2002 | Piper |
| 6,345,617 B1 | 2/2002 | Engelbreth et al. |
| 6,358,058 B1 | 3/2002 | Strupat et al. |
| 6,397,847 B1 * | 6/2002 | Scarberry ......... A61M 16/0605 2/430 |
| 6,435,176 B1 | 8/2002 | Berg et al. |
| 6,435,177 B1 | 8/2002 | Schmidt et al. |
| 6,450,163 B1 | 9/2002 | Blacker et al. |
| 6,481,435 B2 | 11/2002 | Hochrainer et al. |
| 6,513,519 B2 | 2/2003 | Gallem |
| 6,543,448 B1 | 4/2003 | Smith et al. |
| 6,557,549 B2 | 5/2003 | Schmidt |
| 6,578,571 B1 | 6/2003 | Watt |
| 6,584,971 B1 | 7/2003 | Denyer et al. |
| 6,595,203 B1 | 7/2003 | Bird |
| 6,606,992 B1 | 8/2003 | Schuler et al. |
| 6,612,303 B1 | 9/2003 | Grychowski et al. |
| 6,644,304 B2 | 11/2003 | Grychowski et al. |
| 6,651,651 B1 | 11/2003 | Bonney et al. |
| 6,679,250 B2 | 1/2004 | Walker et al. |
| 6,698,421 B2 | 3/2004 | Attolini |
| 6,708,688 B1 | 3/2004 | Rubin et al. |
| 6,748,945 B2 | 6/2004 | Grychowski et al. |
| 6,823,862 B2 | 11/2004 | McNaughton |
| 6,839,604 B2 | 1/2005 | Godfrey et al. |
| 6,848,443 B2 | 2/2005 | Schmidt |
| 6,857,427 B2 | 2/2005 | Ziegler et al. |
| 6,880,722 B2 | 4/2005 | Anderson et al. |
| 6,883,517 B2 | 4/2005 | Halamish |
| 6,885,684 B2 | 4/2005 | Ichino |
| 6,904,907 B2 | 6/2005 | Speldrich et al. |
| 6,904,908 B2 | 6/2005 | Bruce et al. |
| 6,908,449 B2 | 6/2005 | Willis et al. |
| 6,929,003 B2 | 8/2005 | Blacker et al. |
| 6,932,083 B2 | 8/2005 | Jones et al. |
| 6,934,220 B1 | 8/2005 | Cruitt et al. |
| 6,958,691 B1 | 10/2005 | Anderson et al. |
| 6,990,975 B1 | 1/2006 | Jones et al. |
| 6,994,083 B2 | 2/2006 | Foley et al. |
| 7,009,517 B2 | 3/2006 | Wood |
| 7,013,896 B2 | 3/2006 | Schmidt |
| 7,022,764 B2 | 4/2006 | Murray |
| 7,036,505 B2 | 5/2006 | Bacon et al. |
| 7,051,731 B1 | 5/2006 | Rogerson |
| 7,072,738 B2 | 7/2006 | Bonney et al. |
| 7,080,643 B2 | 7/2006 | Grychowski et al. |
| 7,089,786 B2 | 8/2006 | Walker |
| 7,091,864 B2 | 8/2006 | Veitch et al. |
| 7,131,439 B2 | 11/2006 | Blacker et al. |
| 7,131,440 B2 | 11/2006 | Sonntag |
| 7,151,456 B2 | 12/2006 | Godfrey |
| 7,159,533 B1 | 1/2007 | Redd et al. |
| 7,191,777 B2 | 3/2007 | Brand et al. |
| 7,198,172 B2 | 4/2007 | Harvey et al. |
| 7,201,165 B2 | 4/2007 | Bruce et al. |
| 7,233,228 B2 | 6/2007 | Lintell |
| 7,252,085 B2 | 8/2007 | Kunschir |
| 7,255,106 B2 | 8/2007 | Gallem et al. |
| 7,261,102 B2 | 8/2007 | Barney et al. |
| 7,267,120 B2 | 9/2007 | Rustad et al. |
| 7,270,123 B2 | 9/2007 | Grychowski et al. |
| 7,331,340 B2 | 2/2008 | Barney |
| 7,383,837 B2 | 6/2008 | Robertson et al. |
| 7,424,888 B2 | 6/2008 | Harvey et al. |
| 7,404,400 B2 | 7/2008 | Lulla et al. |
| 7,458,372 B2 | 12/2008 | Feiner et al. |
| 7,495,546 B2 | 2/2009 | Lintell |
| 7,559,322 B2 | 7/2009 | Foley et al. |
| 7,562,656 B2 | 7/2009 | Gallem et al. |
| 7,568,480 B2 | 8/2009 | Foley et al. |
| 7,597,099 B2 | 10/2009 | Jones et al. |

(56) References Cited

U.S. PATENT DOCUMENTS

| | | |
|---|---|---|
| 7,634,995 B2 | 12/2009 | Grychowski et al. |
| 7,661,423 B2 | 2/2010 | Brand et al. |
| 7,730,847 B1 | 6/2010 | Redd et al. |
| 7,748,382 B2 | 7/2010 | Denyer et al. |
| 7,748,385 B2 | 7/2010 | Lieberman et al. |
| 7,758,886 B2 | 7/2010 | Jauernig et al. |
| 7,819,116 B2 | 10/2010 | Brand et al. |
| 7,837,648 B2 | 11/2010 | Blair et al. |
| 8,165,892 B2 | 4/2012 | Carter et al. |
| 8,261,738 B2 | 9/2012 | Denyer et al. |
| 8,403,861 B2 | 3/2013 | Williams et al. |
| 8,424,517 B2 | 4/2013 | Sutherland et al. |
| 8,464,707 B2 | 6/2013 | Jongejan et al. |
| 8,550,067 B2 | 10/2013 | Bruce et al. |
| 8,607,783 B2 | 12/2013 | Takei et al. |
| 8,807,131 B1 | 8/2014 | Tunnell et al. |
| 9,035,765 B2 | 5/2015 | Engelhard et al. |
| 9,072,846 B2 | 7/2015 | Helmlinger |
| 9,242,056 B2 | 1/2016 | Andersen et al. |
| D757,926 S | 5/2016 | Van Sickle et al. |
| 9,352,107 B2 | 5/2016 | Von Hollen et al. |
| 9,427,534 B2 | 8/2016 | Bruin et al. |
| 9,452,317 B2 | 9/2016 | Arkush |
| 9,468,729 B2 | 10/2016 | Sutherland et al. |
| D771,800 S | 11/2016 | Engelhard et al. |
| 9,764,104 B2 | 9/2017 | Gumaste et al. |
| 9,782,551 B2 | 10/2017 | Morrison et al. |
| 10,350,375 B2 | 7/2019 | Hickey et al. |
| 10,894,142 B2 | 1/2021 | Costella et al. |
| 2002/0020762 A1 | 2/2002 | Selzer et al. |
| 2002/0029779 A1 | 3/2002 | Schmidt et al. |
| 2002/0090601 A1 | 7/2002 | Strupat et al. |
| 2002/0104531 A1 | 8/2002 | Malone |
| 2002/0157663 A1 | 10/2002 | Blacker et al. |
| 2002/0175594 A1 | 11/2002 | Kornbluh et al. |
| 2003/0075171 A1 | 4/2003 | Jones et al. |
| 2003/0089368 A1 | 5/2003 | Zhao |
| 2003/0136399 A1 | 7/2003 | Foley et al. |
| 2003/0159694 A1 | 8/2003 | McNaughton |
| 2003/0205226 A1 | 11/2003 | Gallem et al. |
| 2004/0007231 A1 | 1/2004 | Zhou |
| 2004/0094148 A1 | 5/2004 | Lulla et al. |
| 2005/0039741 A1 | 2/2005 | Gallem et al. |
| 2005/0087178 A1 | 4/2005 | Milton |
| 2005/0183718 A1 | 8/2005 | Wuttke et al. |
| 2006/0011196 A2 | 1/2006 | Gallem et al. |
| 2006/0089545 A1 | 4/2006 | Ratjen et al. |
| 2006/0157052 A1 | 7/2006 | Foley et al. |
| 2006/0254579 A1 | 11/2006 | Grychowski et al. |
| 2007/0017506 A1 | 1/2007 | Bell et al. |
| 2007/0023036 A1 | 2/2007 | Grychowski et al. |
| 2007/0125372 A1 | 6/2007 | Chen |
| 2007/0204864 A1 | 9/2007 | Grychowski et al. |
| 2007/0235028 A1 | 10/2007 | Bruce et al. |
| 2008/0083407 A1 | 4/2008 | Grychowski et al. |
| 2008/0257345 A1 | 10/2008 | Snyder et al. |
| 2009/0065067 A1 | 3/2009 | Bushman et al. |
| 2009/0194104 A1 | 8/2009 | Van Sickle |
| 2009/0272820 A1 | 11/2009 | Foley et al. |
| 2009/0314292 A1 | 12/2009 | Overfield et al. |
| 2010/0191192 A1 | 7/2010 | Prasad et al. |
| 2010/0192948 A1 | 8/2010 | Sutherland et al. |
| 2010/0250280 A1 | 9/2010 | Sutherland |
| 2010/0252036 A1 | 10/2010 | Sutherland et al. |
| 2010/0324439 A1 | 12/2010 | Davenport |
| 2010/0331877 A1 | 12/2010 | Li et al. |
| 2011/0180563 A1 | 7/2011 | Fitchett et al. |
| 2011/0226237 A1 | 9/2011 | Morrison |
| 2011/0226242 A1 | 9/2011 | Von Hollen et al. |
| 2012/0012106 A1 | 1/2012 | Bari |
| 2012/0165693 A1 | 6/2012 | Williams et al. |
| 2012/0190998 A1* | 7/2012 | Armitstead ....... A61M 16/0633 128/204.23 |
| 2012/0240923 A1 | 9/2012 | Denyer et al. |
| 2012/0285236 A1 | 11/2012 | Haartsen et al. |
| 2012/0291779 A1 | 11/2012 | Haartsen et al. |
| 2012/0312302 A1 | 12/2012 | Cardelius et al. |
| 2013/0008436 A1* | 1/2013 | Von Hollen ........ A61M 15/009 128/200.14 |
| 2013/0053719 A1 | 2/2013 | Wekell |
| 2013/0092158 A1 | 4/2013 | Levy et al. |
| 2013/0151162 A1 | 6/2013 | Harris et al. |
| 2013/0186392 A1 | 7/2013 | Haartsen et al. |
| 2014/0000598 A1 | 1/2014 | Sutherland et al. |
| 2014/0000599 A1 | 1/2014 | Dyche et al. |
| 2014/0106324 A1 | 4/2014 | Adams et al. |
| 2014/0182584 A1 | 7/2014 | Sutherland et al. |
| 2014/0257126 A1 | 9/2014 | Vink et al. |
| 2014/0311483 A1 | 10/2014 | Engelbreth et al. |
| 2014/0311492 A1 | 10/2014 | Stuebiger et al. |
| 2014/0318534 A1 | 10/2014 | Engelbreth |
| 2014/0352690 A1 | 12/2014 | Kolb et al. |
| 2015/0011906 A1 | 1/2015 | Wallach |
| 2015/0053202 A1 | 2/2015 | Knell et al. |
| 2015/0059739 A1 | 3/2015 | Aslam |
| 2015/0061867 A1 | 3/2015 | Engelhard et al. |
| 2015/0099994 A1 | 4/2015 | Spencer et al. |
| 2015/0100276 A1 | 4/2015 | Huang et al. |
| 2015/0100335 A1 | 4/2015 | Engelhard et al. |
| 2015/0112707 A1 | 4/2015 | Manice et al. |
| 2015/0122261 A1 | 5/2015 | Pettit |
| 2015/0164373 A1 | 6/2015 | Davis et al. |
| 2015/0174348 A1 | 6/2015 | Tunnell et al. |
| 2015/0174349 A1 | 6/2015 | Tunnell et al. |
| 2015/0235548 A1 | 8/2015 | Engelhard et al. |
| 2015/0283337 A1 | 10/2015 | Adams et al. |
| 2015/0352281 A1 | 10/2015 | Pfrang |
| 2015/0320958 A1 | 11/2015 | Metysek et al. |
| 2016/0045681 A1 | 2/2016 | Cheatham, III et al. |
| 2016/0045682 A1 | 2/2016 | Boyden et al. |
| 2016/0045683 A1 | 2/2016 | Cheatham, III et al. |
| 2016/0045685 A1 | 2/2016 | Hyde et al. |
| 2016/0051776 A1 | 2/2016 | Von Hollen |
| 2016/0058960 A1 | 3/2016 | Papania et al. |
| 2016/0082208 A1 | 3/2016 | Ballam et al. |
| 2016/0106375 A1 | 4/2016 | Leydon |
| 2016/0106935 A1 | 4/2016 | Sezan et al. |
| 2016/0129182 A1 | 5/2016 | Schuster et al. |
| 2016/0129206 A1 | 5/2016 | Engelbreth |
| 2016/0136366 A1 | 5/2016 | Bennett |
| 2016/0136367 A1 | 5/2016 | Varney |
| 2016/0144141 A1 | 5/2016 | Biwas et al. |
| 2016/0144142 A1 | 5/2016 | Baker et al. |
| 2016/0166766 A1 | 6/2016 | Schuster et al. |
| 2016/0166787 A1* | 6/2016 | Morrison .......... A61M 15/0085 128/200.16 |
| 2016/0184535 A1 | 6/2016 | Edwards et al. |
| 2016/0193436 A1 | 7/2016 | Khasawneh |
| 2016/0213868 A1 | 7/2016 | Khasawneh et al. |
| 2016/0256639 A1 | 9/2016 | Van Sickle et al. |
| 2016/0287139 A1 | 10/2016 | Luttrell |
| 2016/0314256 A1 | 10/2016 | Su et al. |
| 2016/0325058 A1 | 11/2016 | Samson et al. |
| 2016/0331917 A1 | 11/2016 | Bennett et al. |
| 2016/0339187 A1 | 11/2016 | Smaldone |
| 2016/0339190 A1 | 11/2016 | Morrison et al. |
| 2016/0354562 A1 | 12/2016 | Morrison |
| 2016/0354571 A1* | 12/2016 | Grashow ............. A61M 16/065 |
| 2017/0020776 A1 | 1/2017 | Khasawneh et al. |
| 2017/0127945 A1 | 5/2017 | Reed |
| 2017/0173282 A1 | 6/2017 | O'Sullivan et al. |
| 2017/0296772 A1 | 10/2017 | Costella et al. |
| 2017/0333661 A1 | 11/2017 | Bennett et al. |
| 2017/0361045 A1 | 12/2017 | Fu et al. |
| 2018/0008790 A1 | 1/2018 | Costella et al. |
| 2019/0160237 A1 | 5/2019 | O'Callaghan et al. |
| 2020/0001026 A1 | 1/2020 | Starr et al. |

FOREIGN PATENT DOCUMENTS

| | | |
|---|---|---|
| DE | 2804852 A1 | 11/1986 |
| DE | 8703534 U1 | 8/1987 |
| DE | 19902847 C1 | 5/2000 |
| DE | 19953317 C1 | 2/2001 |

(56) References Cited

FOREIGN PATENT DOCUMENTS

| | | |
|---|---|---|
| DE | 102010024912 B4 | 2/2013 |
| EP | 0 281 650 A1 | 9/1988 |
| EP | 0 414 536 A2 | 2/1991 |
| EP | 0 281 650 B1 | 3/1992 |
| EP | 0 514 085 A1 | 11/1992 |
| EP | 0387222 B1 | 7/1993 |
| EP | 0 587 380 A1 | 3/1994 |
| EP | 0 601 708 A2 | 6/1994 |
| EP | 0 641 570 A1 | 3/1995 |
| EP | 0 711 609 A3 | 10/1996 |
| EP | 0 587 380 B1 | 11/1997 |
| EP | 0824023 A1 | 2/1998 |
| EP | 0617628 B1 | 5/1998 |
| EP | 0 855 224 A2 | 7/1999 |
| EP | 0 855 224 A3 | 7/1999 |
| EP | 0 601 708 B1 | 3/2000 |
| EP | 1338296 A1 | 8/2003 |
| EP | 0 855 224 B1 | 5/2004 |
| EP | 0 938 906 B1 | 11/2005 |
| EP | 1330283 B1 | 9/2006 |
| EP | 1993642 B1 | 1/2012 |
| EP | 1670533 B1 | 7/2012 |
| EP | 2300083 B1 | 5/2013 |
| EP | 2609954 A2 | 7/2013 |
| EP | 2376156 B1 | 1/2014 |
| EP | 2859906 A1 | 4/2015 |
| EP | 2563436 B1 | 10/2015 |
| EP | 2512566 B1 | 5/2016 |
| EP | 1613214 B1 | 10/2016 |
| EP | 3053620 A3 | 10/2016 |
| EP | 3097937 A1 | 11/2016 |
| FR | 1 070 292 A | 7/1954 |
| FR | 2 763 507 A | 11/1998 |
| GB | 497530 | 12/1939 |
| GB | 675524 | 7/1952 |
| GB | 2 253 200 A | 9/1992 |
| GB | 2 299 512 A | 10/1996 |
| GB | 2 310 607 A | 9/1997 |
| GB | 2406283 A | 3/2005 |
| GB | 2479953 A | 2/2011 |
| GB | 2490770 A | 11/2012 |
| GB | 2512047 A | 9/2014 |
| GB | 2479953 B | 4/2015 |
| WO | WO 88/03419 A1 | 5/1988 |
| WO | WO 90/09203 A1 | 8/1990 |
| WO | WO9010470 A1 | 9/1990 |
| WO | WO9207599 A1 | 5/1992 |
| WO | WO 93/11817 A1 | 6/1993 |
| WO | WO9312823 A2 | 7/1993 |
| WO | WO 94/17753 A1 | 8/1994 |
| WO | WO9507723 A1 | 2/1995 |
| WO | WO 95/20414 A1 | 8/1995 |
| WO | WO9522365 A1 | 8/1995 |
| WO | WO9729799 A2 | 8/1997 |
| WO | WO 98/19727 A1 | 5/1998 |
| WO | WO 98/26828 A2 | 6/1998 |
| WO | WO 98/41265 A1 | 9/1998 |
| WO | WO 98/44974 A1 | 10/1998 |
| WO | WO1999008737 | 2/1999 |
| WO | WO9911310 A1 | 3/1999 |
| WO | WO 99/40959 A1 | 8/1999 |
| WO | WO 99/53982 A1 | 10/1999 |
| WO | WO2000035524 A2 | 6/2000 |
| WO | WO 00/59565 A1 | 10/2000 |
| WO | WO 02/04056 A1 | 1/2002 |
| WO | WO0205879 A1 | 1/2002 |
| WO | WO0209574 A2 | 2/2002 |
| WO | WO 02/24263 A2 | 3/2002 |
| WO | WO02058771 A1 | 8/2002 |
| WO | WO03020349 A2 | 3/2003 |
| WO | WO03063937 A1 | 8/2003 |
| WO | WO03092576 A2 | 11/2003 |
| WO | WO03107523 A1 | 12/2003 |
| WO | WO2005042076 A1 | 5/2005 |
| WO | WO2005074455 A2 | 8/2005 |
| WO | WO2006123956 A1 | 11/2006 |
| WO | WO2007101438 A1 | 9/2007 |
| WO | WO2008112353 A2 | 9/2008 |
| WO | WO2009022139 A1 | 2/2009 |
| WO | WO2010023591 A2 | 3/2010 |
| WO | WO2010023591 A3 | 3/2010 |
| WO | WO2010110682 A1 | 9/2010 |
| WO | WO2010114392 A1 | 10/2010 |
| WO | WO2011003017 A1 | 1/2011 |
| WO | WO2011073806 A1 | 6/2011 |
| WO | WO2011083377 A1 | 7/2011 |
| WO | WO2011089486 A1 | 7/2011 |
| WO | WO2011089489 A1 | 7/2011 |
| WO | WO2011089490 A1 | 7/2011 |
| WO | WO2011130183 A2 | 10/2011 |
| WO | WO2011130583 A2 | 10/2011 |
| WO | WO2011135353 A1 | 11/2011 |
| WO | WO2012038861 A1 | 3/2012 |
| WO | WO2012064540 A2 | 5/2012 |
| WO | WO2012173992 A1 | 12/2012 |
| WO | WO2013028705 A2 | 2/2013 |
| WO | WO2013042002 A1 | 3/2013 |
| WO | WO2013043063 A1 | 3/2013 |
| WO | WO2013061240 A1 | 5/2013 |
| WO | WO2013061248 A1 | 5/2013 |
| WO | WO2013098334 A1 | 7/2013 |
| WO | WO2013124624 A1 | 8/2013 |
| WO | WO2014004437 A1 | 1/2014 |
| WO | WO2014033229 A1 | 3/2014 |
| WO | WO2014147550 A1 | 9/2014 |
| WO | WO2014202923 A1 | 12/2014 |
| WO | WO2014204511 A3 | 12/2014 |
| WO | WO-2015002652 A1 * | 1/2015 ........ A61M 15/0086 |
| WO | WO2015002652 A1 | 1/2015 |
| WO | WO2015004554 A1 | 1/2015 |
| WO | WO2015004559 A2 | 1/2015 |
| WO | WO2015006701 A2 | 1/2015 |
| WO | WO2015008013 A1 | 1/2015 |
| WO | WO2015022595 A1 | 2/2015 |
| WO | WO2015030610 A3 | 3/2015 |
| WO | WO2015031472 A1 | 3/2015 |
| WO | WO2015036010 A3 | 3/2015 |
| WO | WO2015036723 A1 | 3/2015 |
| WO | WO2015052519 A1 | 4/2015 |
| WO | WO2015104522 A1 | 7/2015 |
| WO | WO2015109259 A1 | 7/2015 |
| WO | WO2015114285 A1 | 8/2015 |
| WO | WO2015128173 A1 | 9/2015 |
| WO | WO2015133909 A1 | 9/2015 |
| WO | WO2015138454 A1 | 9/2015 |
| WO | WO2015144442 A1 | 10/2015 |
| WO | WO2015150029 A1 | 10/2015 |
| WO | WO2015154864 A2 | 10/2015 |
| WO | WO2015154865 A2 | 10/2015 |
| WO | WO2015174856 A1 | 11/2015 |
| WO | WO2015178907 A1 | 11/2015 |
| WO | WO2016025553 A1 | 2/2016 |
| WO | WO2016030521 A1 | 3/2016 |
| WO | WO2016033419 A1 | 3/2016 |
| WO | WO2016033421 A1 | 3/2016 |
| WO | WO2016043601 A1 | 3/2016 |
| WO | WO2016048435 A1 | 3/2016 |
| WO | WO2016049066 A1 | 3/2016 |
| WO | WO2016060863 A3 | 4/2016 |
| WO | WO 2016/079461 A1 | 5/2016 |
| WO | WO2016075525 A1 | 5/2016 |
| WO | WO2016081294 A1 | 5/2016 |
| WO | WO2016085988 A2 | 6/2016 |
| WO | WO2016090260 A1 | 6/2016 |
| WO | WO 2016/110804 A1 | 7/2016 |
| WO | WO2016111633 A1 | 7/2016 |
| WO | WO2016116591 A1 | 7/2016 |
| WO | WO2016162699 A1 | 10/2016 |
| WO | WO2016165029 A1 | 10/2016 |
| WO | WO2016181048 A1 | 11/2016 |
| WO | WO 2017/071879 A1 | 5/2017 |
| WO | WO 2017/178776 A1 | 10/2017 |

(56) References Cited

FOREIGN PATENT DOCUMENTS

| WO | WO 2017/187116 A1 | 11/2017 |
| WO | WO 2017/194906 A1 | 11/2017 |
| WO | WO 2021/255202 A1 | 12/2021 |

OTHER PUBLICATIONS

International Search Report in International Application No. PCT/IB2017/052968 dated Sep. 5, 2017, 7 pages.
PCT Notification of the International Search Report and Written Opinion of the International Search Authority dated Jan. 5, 2018, 10 pgs.

\* cited by examiner

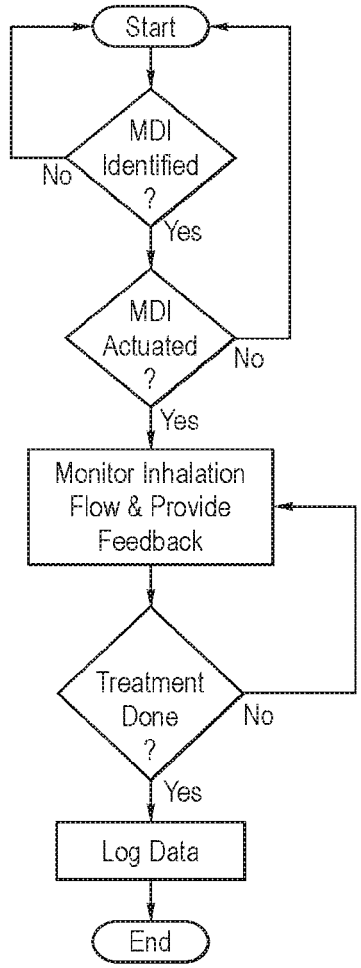
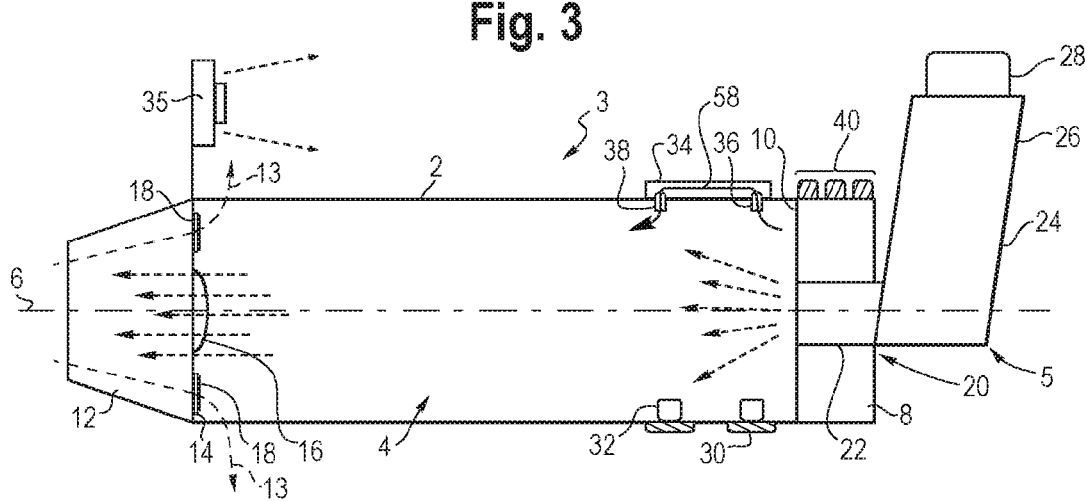

78
Pressure
1   2
60   110

MEDICATION DELIVERY SYSTEM WITH MASK

This application is a continuation of U.S. application Ser. No. 15/600,039, filed May 19, 2017, which application claims the benefit of U.S. Provisional Application No. 62/338,798, filed May 19, 2016, and U.S. Provisional Application No. 62/366,327, filed Jul. 25, 2016, the entire disclosures of which are hereby incorporated herein by reference.

FIELD OF THE INVENTION

This application is directed to devices and systems for use in the field of pulmonary aerosol drug delivery via a metered dose inhaler (MDI) and valved holding chamber (VHC), and in particular devices and systems for improving patient adherence to their medication regimen and providing feedback to the user, prescriber or payer regarding proper inhalation technique and end of treatment.

BACKGROUND

VHC and MDI systems are typically used to treat such conditions as asthma, COPD and cystic fibrosis. Patients being treated for such conditions may exhibit poor adherence to medication or therapy regimes, practice improper device technique and/or fail to receive feedback about dose assurance. These types of problems may create additional cost burdens for the healthcare system with less than optimal patient outcomes.

Medication compliance is often difficult to monitor although this information is invaluable to healthcare and insurance providers. Currently, there is no way to actively monitor a patient's use of a VHC, and despite the recent advent of smart inhalers, most MDI's are not able to monitor and communicate medication use on their own. Therefore, the need exists for a VHC that is capable of monitoring medication usage, as well as providing feedback to the user and healthcare and insurance providers.

BRIEF SUMMARY

Upon insertion of an MDI into a VHC, the system identifies the MDI being inserted in the VHC. As the user performs practice breaths, the system monitors flow rates and provides feedback to the user regarding their technique, including whether the user is breathing too fast, or if their breath-hold is adequate. During this practice phase, the system is capable of notifying the user of the most appropriate time in their breathing cycle to actuate the MDI.

Once the MDI is actuated, the system detects and records the actuation, and the duration between actuation and the first inhalation flow. This information is used to provide coordination feedback following the current treatment and/or at the beginning of subsequent treatments. At the end of an inhalation, a second timer may start that measures the breath-hold duration of the user. This information may be used to provide further feedback before the next breath-hold or before the next treatment.

Following MDI actuation, the system may determine when the user has received their full dose of medication. This may be accomplished by measuring the flow rate and integrating for total volume delivered or by other means. At the end of treatment, the user is notified and the system, by default, waits for a second actuation of the MDI. If too much time has passed without an actuation, the system will turn off. Additionally, if the user removes the MDI, the program will terminate in one embodiment.

Various methods may be used to relay information and provide feedback to the user. LEDs, LED boards, 7-segment displays, LCD and/or OLED screens may be used to provide visual feedback. Audio feedback may also be used with the option of muting the sound at the discretion of the user. Haptic feedback may also be used, with VHC vibrating when an excessive flow rate is pulled, for example. Information may be displayed on a screen, or on a mobile device, remote computer, or other user interface, using, for example, an app or website.

The various systems and devices improve patient adherence, improve device technique and provide dose assurance. These aspect, in turn, help reduce costs for healthcare systems and providers (payers) by ensuring proper adherence. In addition, healthcare providers (prescribers), having reliable information about adherence and usage, may then rely on the patient specific data to make informed decisions about treatment protocol and changes. The patients, in turn, receive maximum benefit from the treatment, while also reducing out of pocket costs.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

The Figures show different embodiments of medication delivery systems, block/flow diagrams and methods for use and assembly thereof.

FIG. 2 is a flow chart illustrating the use and feedback loops for a smart VHC device.

FIG. 3 is a side view of one embodiment of a smart VHC.

FIG. 18 is a side view of another embodiment of a smart VHC.

FIG. 19 is a partial side view of another embodiment of a smart VHC.

FIG. 49 is a side view of one embodiment of a smart MDI.

FIG. 50 is an enlarged partial view of the smart MDI shown in FIG. 49.

DETAILED DESCRIPTION OF THE DRAWINGS
AND THE PRESENTLY PREFERRED
EMBODIMENTS

It should be understood that the term "plurality," as used herein, means two or more. The term "coupled" means connected to or engaged with whether directly or indirectly, for example with an intervening member, and does not require the engagement to be fixed or permanent, although it may be fixed or permanent (or integral), and includes both mechanical and electrical connection. The terms "first," "second," and so on, as used herein are not meant to be assigned to a particular component so designated, but rather are simply referring to such components in the numerical order as addressed, meaning that a component designated as "first" may later be a "second" such component, depending on the order in which it is referred. It should also be understood that designation of "first" and "second" does not necessarily mean that the two components or values so designated are different, meaning for example a first component may be the same as a second component, with each simply being applicable to separate but identical components.

In a traditional patient/prescriber/payer model, the patient is prescribed a therapy and purchases the medications and/or therapy device. If the purchase is covered by a payer, there typically is no feedback to the payer that the therapy is being performed correctly and as prescribed, aside from future requests for additional therapies. The patient typically is trained on the use of the medical device by a prescriber and then asked to use the device in their daily life. At some point, the patient may follow up with the prescriber because of a condition change, a prescription refill, or perhaps at a set frequency. At such a time, the prescriber may evaluate the effectiveness of the treatment and decide to modify or continue therapy. If the prescriber decides to modify the therapy, then a new prescription is given and the cycle repeated. Some of the technical challenges faced in improving adherence to treatment regimens, that in turn may lead to improved cost tracking and diagnosis, include challenges in the ability to effectively monitor the functions of different therapeutic devices and the usage of the device, how to then provide an effective real-time feedback to a user and/or a prescriber, and how to make real-time changes to the performance of the device and/or behavior/technique of the user in certain instances.

Figure 1:
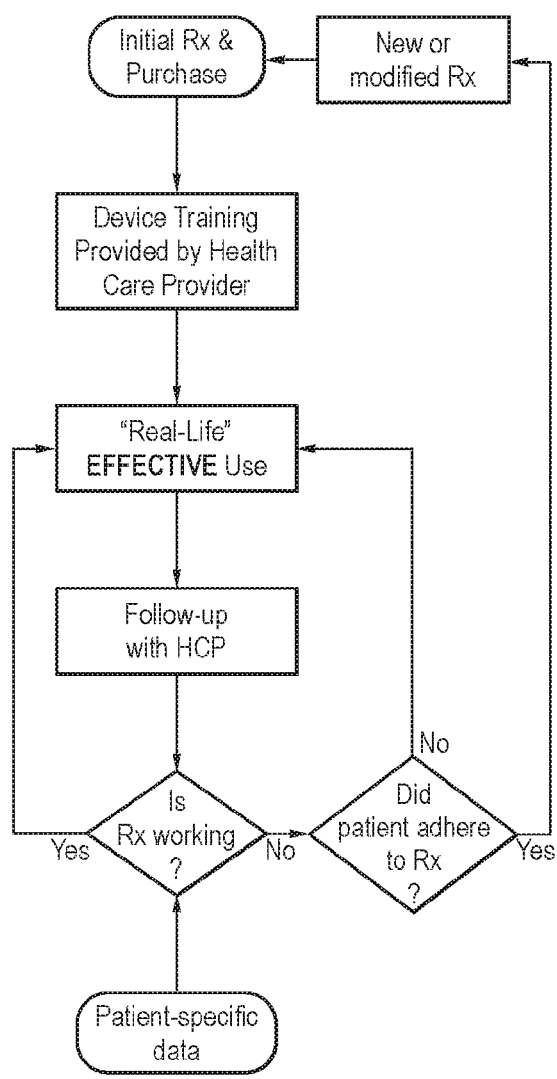
FIG. 1 is a flow chart illustrating a feedback loop for patient adherence, treatment protocol and payer interaction.

Referring to FIGS. 1 and 2, various smart devices, and feedback associated therewith, may be introduced to improve the effectiveness of the therapy. In addition, the prescriber is provided patient-specific data to make informed decisions about treatment, including the modification thereof, and the payer is provided with an assurance that the patient has adhered to the treatment regimen before covering the costs of another prescription.

Referring to FIG. 3, one exemplary embodiment of a smart VHC includes a chamber housing 2 having a wall defining an interior space 4 extending along a longitudinal axis/inhalation flow path 6, a back piece 8 coupled to an input end 10 of the chamber housing and a mouthpiece and/or valve assembly 12 coupled to an output end 14 of the chamber housing. The mouthpiece assembly may be releasably and removably coupled to the chamber housing, for example with tabs received in grooves. The mouthpiece is configured with an inhalation valve 16 and/or an exhalation valve 18, which provides an exhalation flow path 13. The inhalation and exhalation valves may alternatively be disposed on other components of the VHC. In various embodiments, a valve is configured as part of an annular donut valve, having an inner periphery that defines the inhalation valve 16 and an outer periphery defining an exhalation valve 18. In other embodiments, the inhalation valve is configured as a duckbill valve, which may also have an outer annular flange defining the exhalation valve. In other embodiments, the inhalation and exhalation valves may not be integral, but rather are separately formed and disposed within the VHC. The backpiece 8 is configured with an opening 20, which is shaped to receive a mouthpiece portion 22 of a MDI actuation boot 24. The boot further includes a chimney portion 26 defining a cavity shaped to receive a medicament container 28. The boot further includes a support block defining a well shaped to receive a valve stem of the MDI. The well communicates with an orifice, which releases aerosolized medication into the interior space of the chamber housing. Various embodiments of the VHC and MDI, including the mouthpiece assembly, chamber housing and backpiece, are disclosed for example and without limitation in U.S. Pat. Nos. 6,557,549, 7,201,165, 7,360,537 and 8,550,067, all assigned to Trudell Medical International, the Assignee of the present application, with the entire disclosures of the noted patents being hereby incorporated herein by reference.

Figure 12:
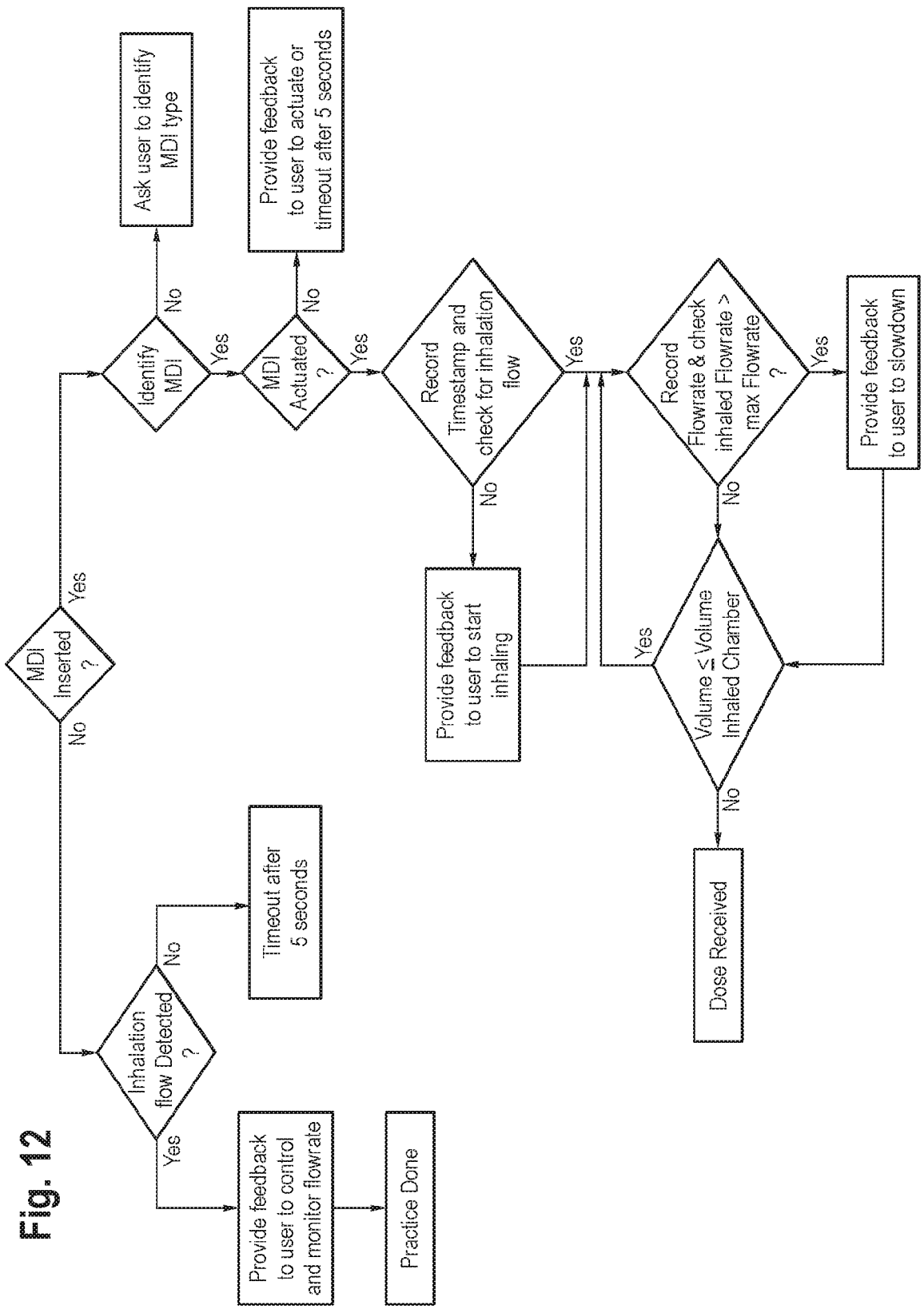
FIG. 12 is a flow chart illustrating MDI usage and feedback loops.

In one embodiment, the VHC 3 is configured to correctly identify the MDI being inserted into the VHC, correctly identify when the MDI 5 has been actuated, and monitor and provide feedback to the user regarding proper technique, as shown for example in FIG. 12. For example, and referring to FIGS. 3 and 7, the VHC may have a Blue LED 30 coupled to the wall of the chamber housing in the interior space 4 and a photodetector 32 also disposed in the interior space 4 at a spaced apart location from the LED 30. The photodetector 32 may be coupled, for example to the wall. A camera 35 may be coupled to the holding chamber 2, for example adjacent the mouthpiece assembly 12, or closer to the backpiece 8. A flow detector, such as a flow sensor 34, is coupled to the wall of the chamber housing, and has an input port 36 and an output port 38 communicating with the interior space. A feedback device, such as a visual feedback indicator 40, for example an LED, or array of LED's, is disposed on the backpiece 8, although it may also be coupled to the chamber housing or mouthpiece assembly.

Figure 22:
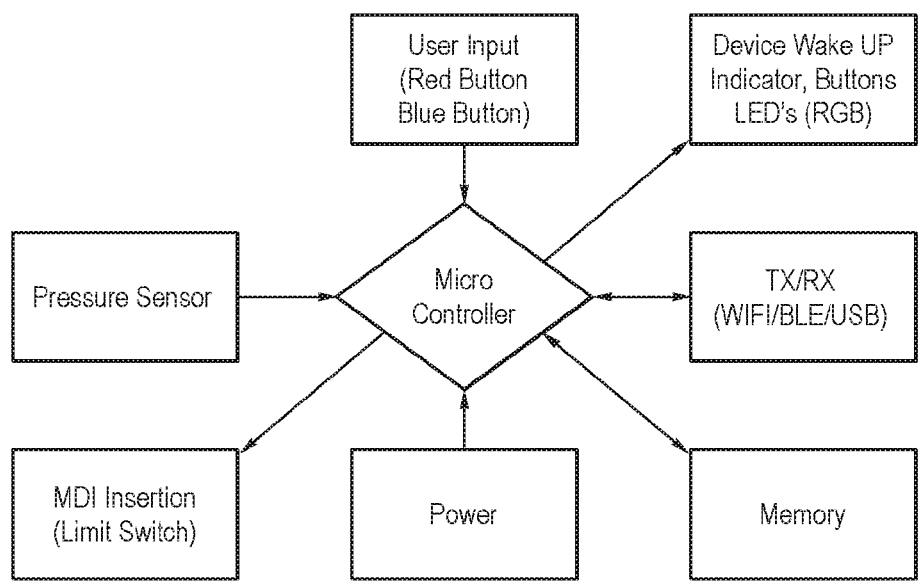
FIG. 22 is a schematic showing various controller inputs.
Figure 23:
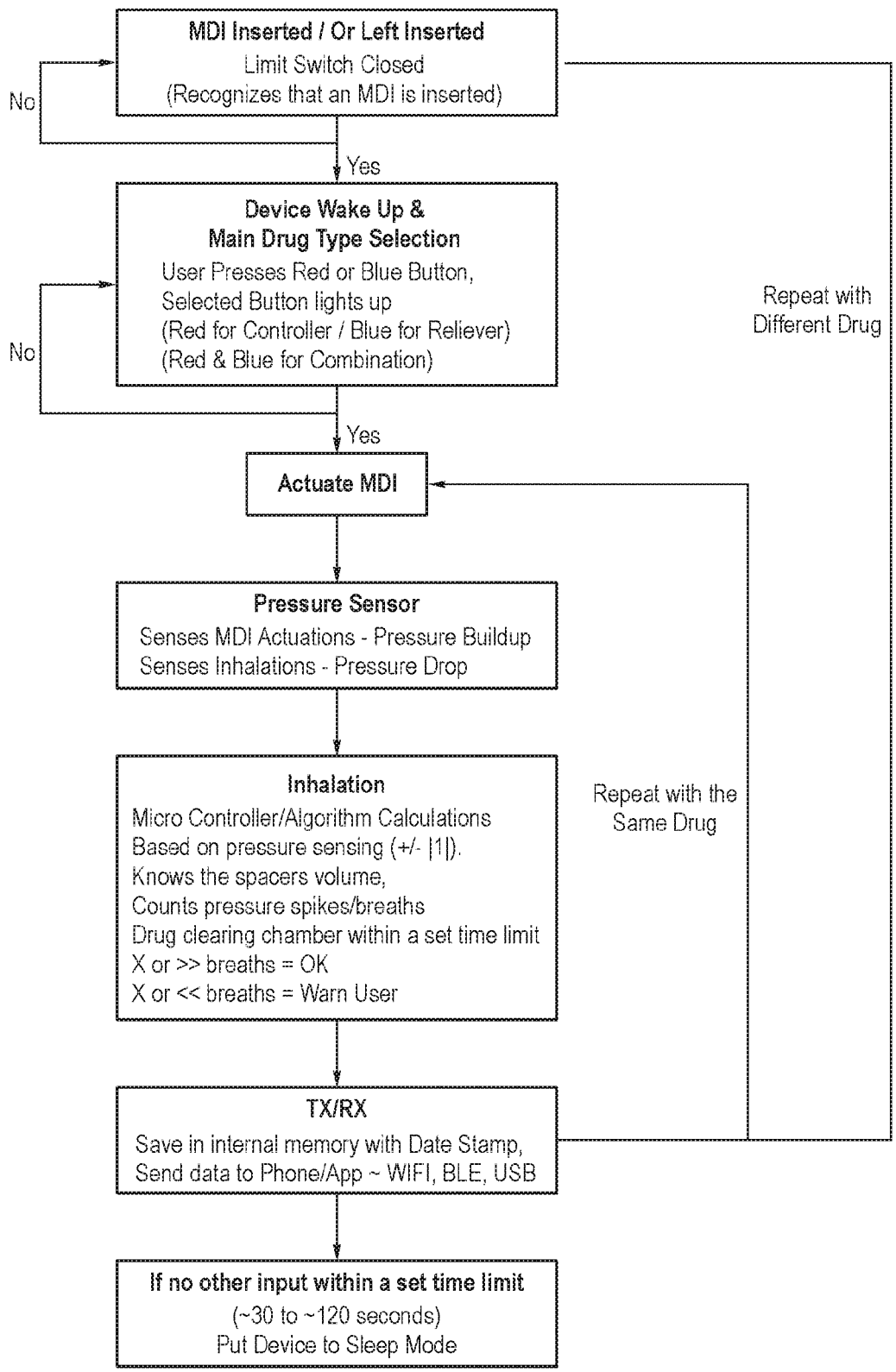
FIG. 23 is a flow chart illustrating MDI usage and feedback loops.
Figure 27:
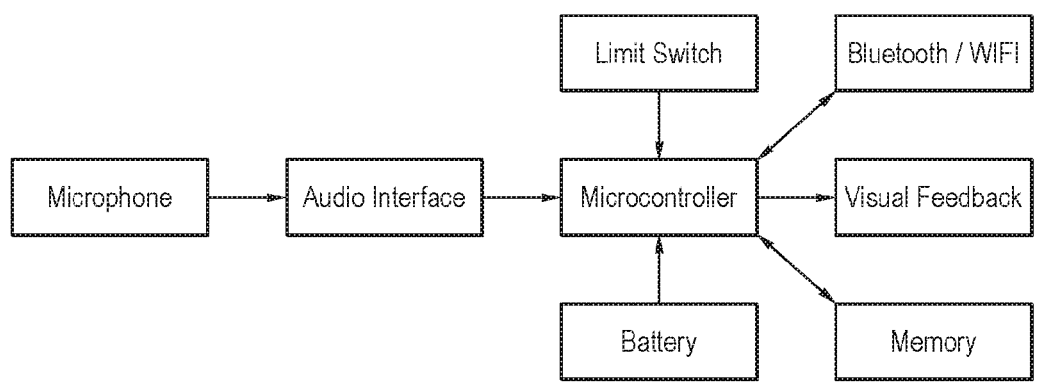
FIG. 27 is a schematic showing various controller inputs.
Figure 28:
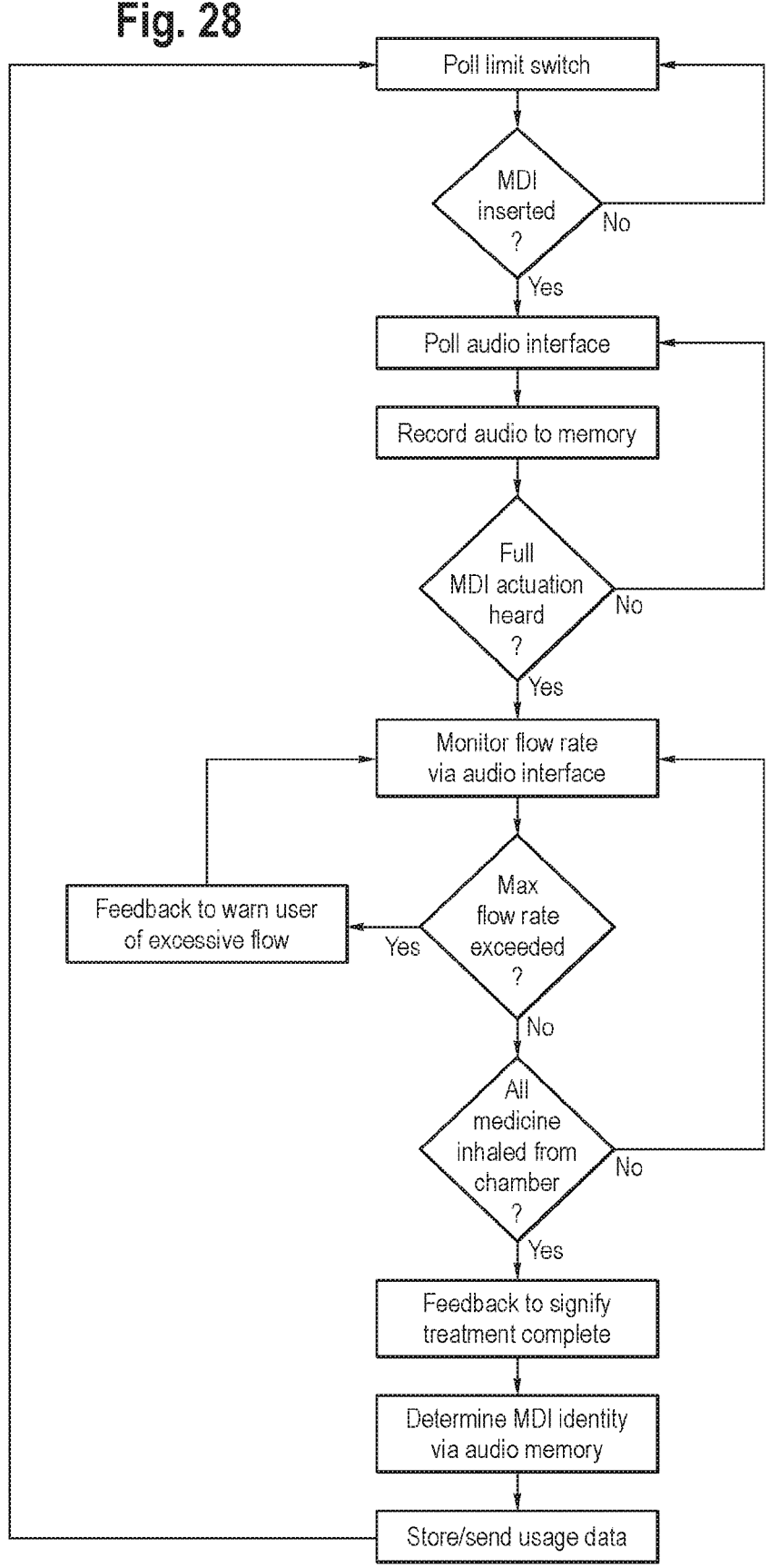
FIG. 28 is a flow chart illustrating MDI usage and feedback loops.
Figure 79:
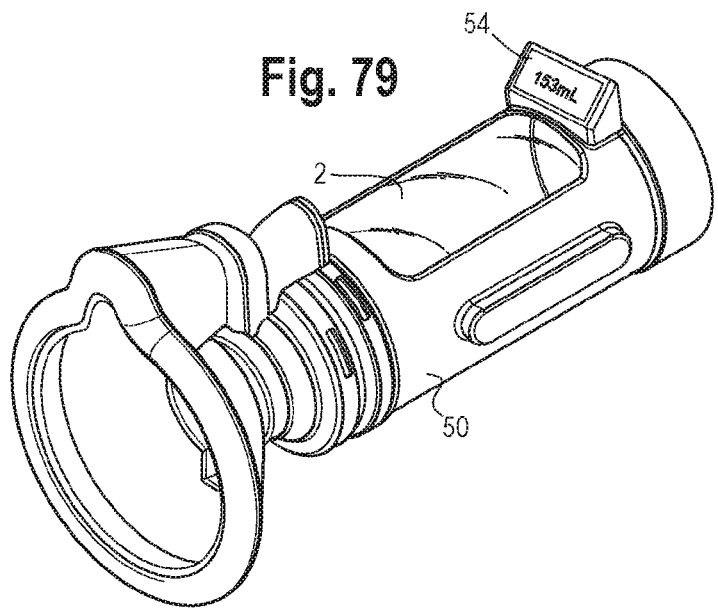
FIG. 79 is a perspective view of a valve holding chamber with an adapter having a display.
Figure 80:
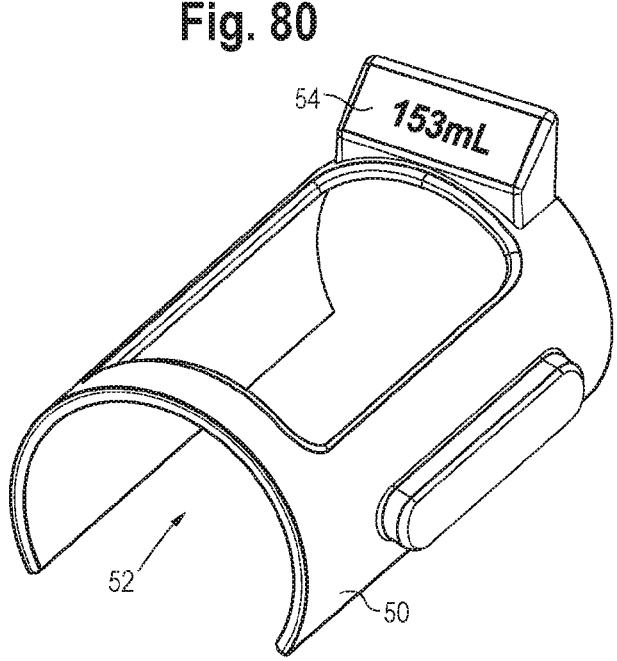
FIG. 80 is a perspective view of the adapter shown in FIG. 79.
Figure 81:
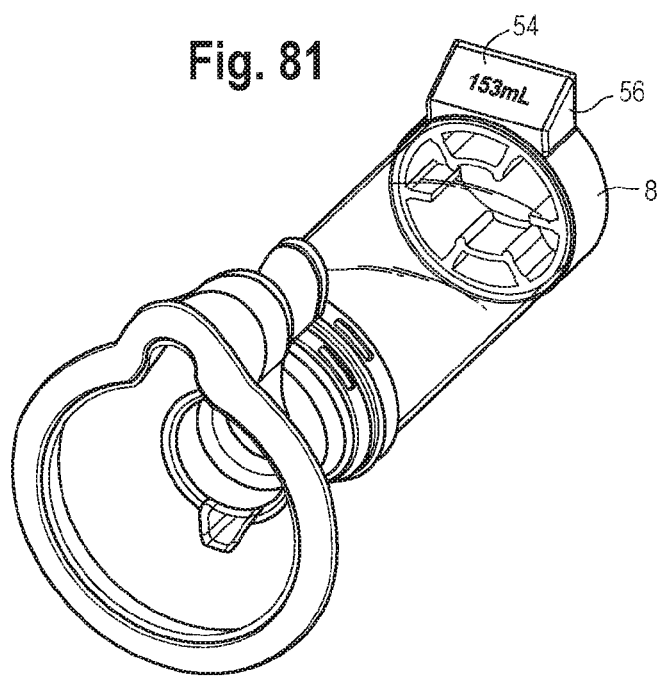
FIG. 81 is a perspective view of a valve holding chamber with a backpiece having a display.
Figure 82:
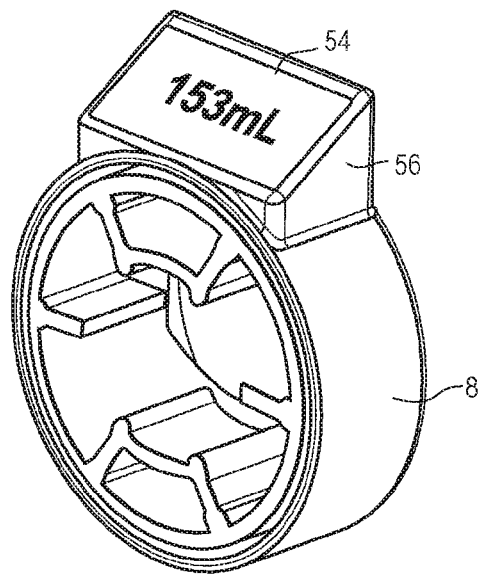
FIG. 82 is a perspective view of the backpiece shown in FIG. 81.
Figure 83:
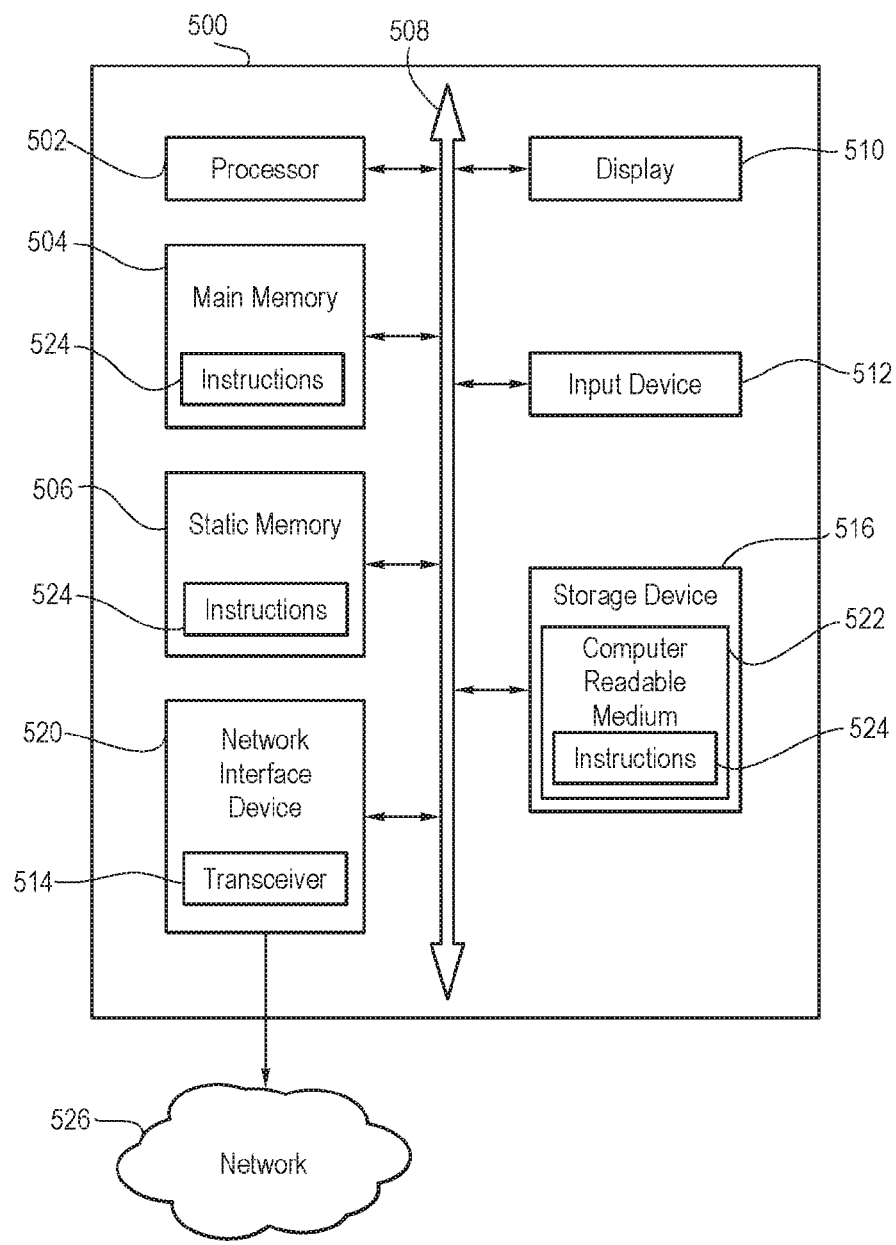
FIG. 83 is a schematic illustrating the computer structure.
Figure 84:
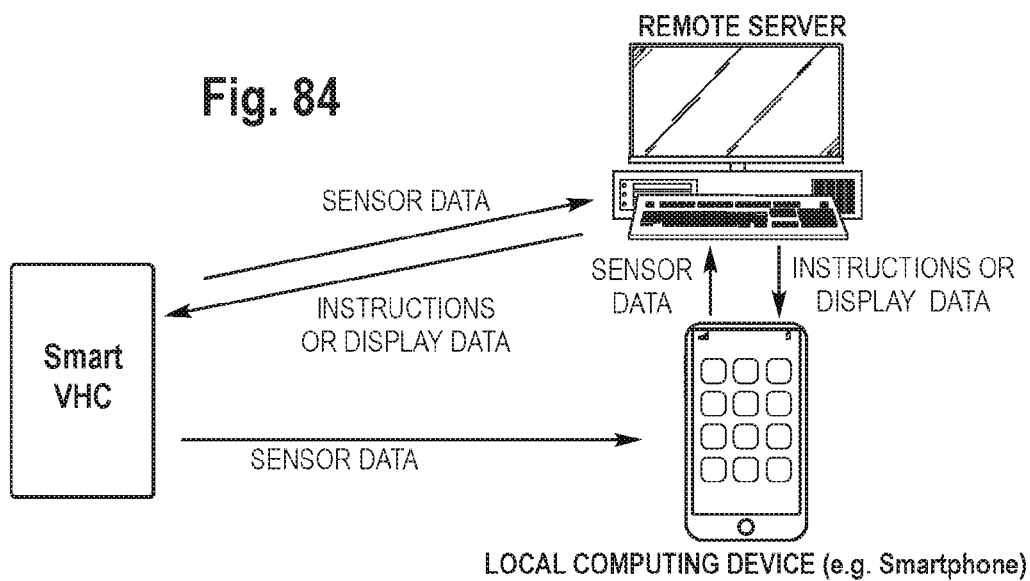
FIG. 84 is a schematic illustration of a communication system.
Figure 85:
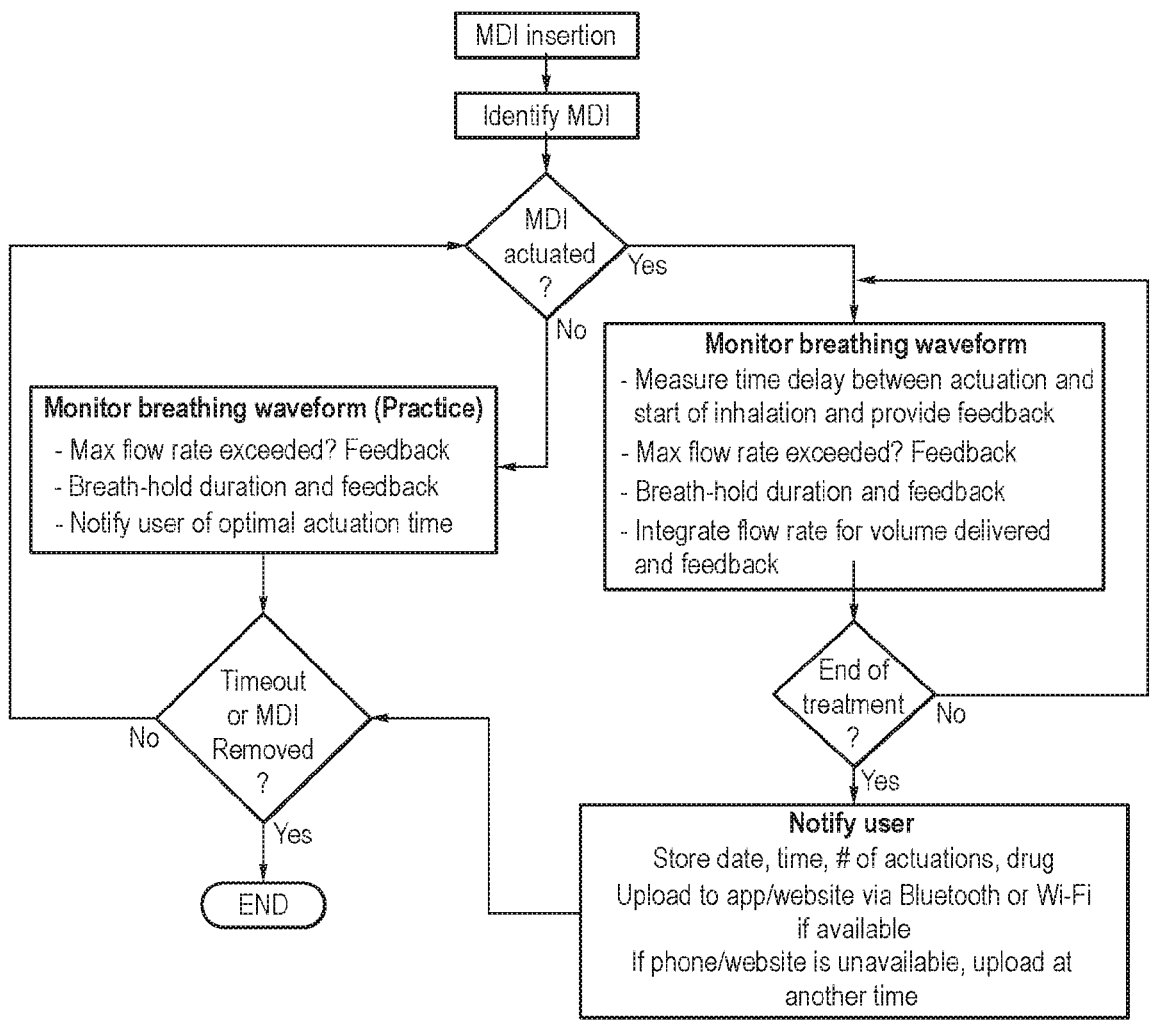
FIG. 85 is a flow chart showing usage protocol of a smart VHC and MDI.

As shown in FIGS. 79 and 80, an adapter 50 includes a shell having a C-shape interior 52 shaped to engage, e.g., with a snap-fit, the chamber housing 2. The adapter includes a feedback device, configured as a display 54 visible to the user, and may include a microcontroller 56 and communication components. As shown in FIGS. 81 and 82, the backpiece includes a display 54 and/or microcontroller 56. The display 54 in each embodiment displays various information, such as various feedback information disclosed herein, to the user and/or caregiver. In different embodiments, the microcontroller 56 may implemented as the controller arrangement illustrated in FIG. 16, microcontroller arrangements of FIG. 22 or 27, or as a processor 502 with one or more components of a more complete computer 500 as shown in FIG. 83.

Communication and Data Processing

In seeking to satisfy these propositions, the device, such as a VHC associated with an MDI, may be configured to perform one or more of the following: (1) correctly identify the MDI being used with the VHC, (2) correctly identify when the MDI has been actuated, (3) monitor and provide feedback to the user regarding proper technique and (4) provide patient specific data to the prescriber and/or provider. Referring to FIGS. 2, 16, 65, 66A-C, 67, 83 and 84, one aspect of the embodiments relates to the handling of data. Data logged by the VHC and/or MDI may be transferred to an external device, such as a smartphone, tablet, personal computer, etc. If such an external device is unavailable, the data may be stored internally in the VHC and/or MDI in a data storage module or other memory and transferred upon the next syncing between the VHC/MDI and external device. Software may accompany the VHC/MDI to implement the data transfer and analysis.

In order to provide faster and more accurate processing of the data, for example from one or more various sensors, generated within the smart VHC and/or MDI, data may be wirelessly communicated to a smart phone, local computing device and/or remote computing device to interpret and act on the raw sensor data.

In one implementation, the smart VHC and/or MDI includes circuitry for transmitting raw sensor data in real-time to a local device, such as a smart phone. The smart phone may display graphics or instructions to the user and implement processing software to interpret and act on the raw data. The smart phone may include software that filters and processes the raw sensor data and outputs the relevant status information contained in the raw sensor data to a display on the smart phone. The smart phone or other local computing device may alternatively use its local resources to contact a remote database or server to retrieve processing instructions or to forward the raw sensor data for remote processing and interpretation, and to receive the processed and interpreted sensor data back from the remote server for display to the user or a caregiver that is with the user of the smart VHC.

In addition to simply presenting data, statistics or instructions on a display of the smart phone or other local computer in proximity of the smart VHC and/or MDI, proactive operations relating to the smart VHC and/or MDI may be actively managed and controlled. For example, if the smart phone or other local computer in proximity to the smart VHC and/or MDI determines that the sensor data indicates the end of treatment has been reached, or that further treatment is needed, the smart phone or other local computing device may communicate such information directly to the patient. Other variations are also contemplated, for example where a remote server in communication with the smart phone, or in direct communication with the smart VHC and/or MDI via a communication network, can supply the information and instructions to the patient/user.

In yet other implementations, real-time data gathered in the smart VHC and/or MDI and relayed via to the smart phone to the remote server may trigger the remote server to track down and notify a physician or supervising caregiver regarding a problem with the particular treatment session or a pattern that has developed over time based on past treatment sessions for the particular user. Based on data from the one or more sensors in the smart VHC and/or MDI, the remote server may generate alerts to send via text, email or other electronic communication medium to the user, the user's physician or other caregiver.

The electronic circuitry in the smart VHC and/or MDI (e.g. the controller arrangement of FIG. 16), the local computing device and/or the remote server discussed above, may include some or all of the capabilities of a computer 500 in communication with a network 526 and/or directly with other computers. As illustrated in FIGS. 65, 6A-C, 67, 76, 77, 83 and 84, the computer 500 may include a processor 502, a storage device 516, a display or other output device 510, an input device 512, and a network interface device 520, all connected via a bus 508. A battery 503 is coupled to and powers the computer. The computer may communicate with the network. The processor 502 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor 502 executes instructions and includes that portion of the computer 500 that controls the operation of the entire computer. Although not depicted in FIGS. 83 and 84, the processor 502 typically includes a control unit that organizes data and program storage in memory and transfers data and other information between the various parts of the computer 500. The processor 502 receives input data from the input device 512 and the network 526 reads and stores instructions (for example processor executable code) 524 and data in the main memory 504, such as random access memory (RAM), static memory 506, such as read only memory (ROM), and the storage device 516. The processor 502 may present data to a user via the output device 510.

Although the computer 500 is shown to contain only a single processor 502 and a single bus 508, the disclosed embodiment applies equally to computers that may have multiple processors and to computers that may have multiple busses with some or all performing different functions in different ways.

The storage device 516 represents one or more mechanisms for storing data. For example, the storage device 516 may include a computer readable medium 522 such as read-only memory (ROM), RAM, non-volatile storage media, optical storage media, flash memory devices, and/or other machine-readable media. In other embodiments, any appropriate type of storage device may be used. Although only one storage device 516 is shown, multiple storage devices and multiple types of storage devices may be present. Further, although the computer 500 is drawn to contain the storage device 516, it may be distributed across other computers, for example on a server.

The storage device 516 may include a controller (not shown) and a computer readable medium 522 having instructions 524 capable of being executed on the processor 502 to carry out the functions described above with reference to processing sensor data, displaying the sensor data or instructions based on the sensor data, controlling aspects of the smart VHC and/or MDI to alter its operation, or contacting third parties or other remotely located resources to provide update information to, or retrieve data from those remotely located resources. In another embodiment, some or all of the functions are carried out via hardware in lieu of a processor-based system. In one embodiment, the controller is a web browser, but in other embodiments the controller may be a database system, a file system, an electronic mail system, a media manager, an image manager, or may include any other functions capable of accessing data items. The storage device 516 may also contain additional software and data (not shown), which is not necessary to understand the invention.

The output device 510 is that part of the computer 500 that displays output to the user. The output device 510 may be a liquid crystal display (LCD) well-known in the art of computer hardware. In other embodiments, the output device 510 may be replaced with a gas or plasma-based flat-panel display or a traditional cathode-ray tube (CRT) display. In still other embodiments, any appropriate display device may be used. Although only one output device 510 is shown, in other embodiments any number of output devices of different types, or of the same type, may be present. In an embodiment, the output device 510 displays a user interface. The input device 512 may be a keyboard, mouse or other pointing device, trackball, touchpad, touch screen, keypad, microphone, voice recognition device, or any other appropriate mechanism for the user to input data to the computer 500 and manipulate the user interface previously discussed. Although only one input device 512 is shown, in another embodiment any number and type of input devices may be present.

The network interface device 520 provides connectivity from the computer 500 to the network 526 through any suitable communications protocol. The network interface device 520 sends and receives data items from the network 526 via a wireless or wired transceiver 514. The transceiver 514 may be a cellular frequency, radio frequency (RF), infrared (IR) or any of a number of known wireless or wired transmission systems capable of communicating with a network 526 or other smart devices 102 having some or all of the features of the example computer of FIGS. 83 and 84. The bus 508 may represent one or more busses, e.g., USB, PCI, ISA (Industry Standard Architecture), X-Bus, EISA (Extended Industry Standard Architecture), or any other appropriate bus and/or bridge (also called a bus controller).

The computer 500 may be implemented using any suitable hardware and/or software, such as a personal computer or other electronic computing device. The computer 500 may be a portable computer, laptop, tablet or notebook computers, smart phones, PDAs, pocket computers, appliances, telephones, and mainframe computers are examples of other possible configurations of the computer 500. The network 526 may be any suitable network and may support any appropriate protocol suitable for communication to the computer 500. In an embodiment, the network 526 may support wireless communications. In another embodiment, the network 526 may support hard-wired communications, such as a telephone line or cable. In another embodiment, the network 526 may support the Ethernet IEEE (Institute of Electrical and Electronics Engineers) 802.3x specification. In another embodiment, the network 526 may be the Internet and may support IP (Internet Protocol). In another embodiment, the network 526 may be a LAN or a WAN. In another embodiment, the network 526 may be a hotspot service provider network. In another embodiment, the network 526 may be an intranet. In another embodiment, the network 526 may be a GPRS (General Packet Radio Service) network. In another embodiment, the network 526 may be any appropriate cellular data network or cell-based radio network technology. In another embodiment, the network 526 may be an IEEE 802.11 wireless network. In still another embodiment, the network 526 may be any suitable network or combination of networks. Although one network 526 is shown, in other embodiments any number of networks (of the same or different types) may be present.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or use the processes described in connection with the presently disclosed subject matter, e.g., through the use of an API, reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations. Although exemplary embodiments may refer to using aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be spread across a plurality of devices. Such devices might include personal computers, network servers, and handheld devices, for example.

Proper Technique

Figure 9:
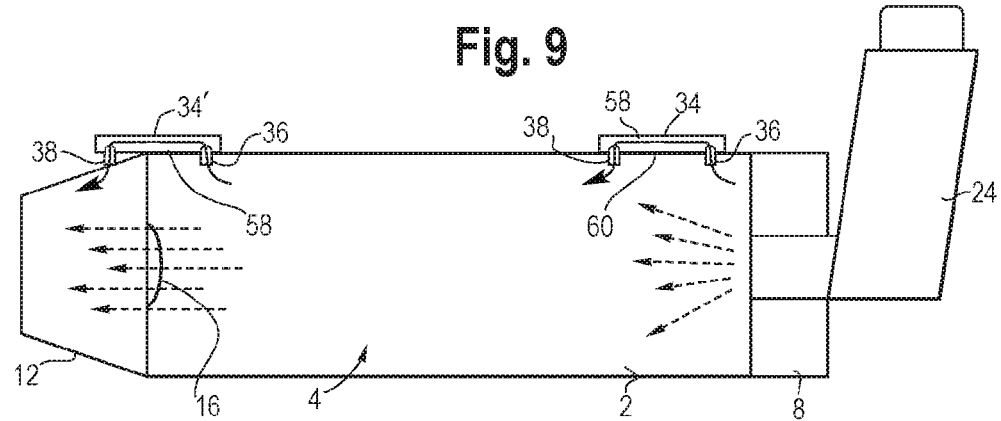
FIG. 9 is a side view of another embodiment of a smart VHC.
Figure 10:
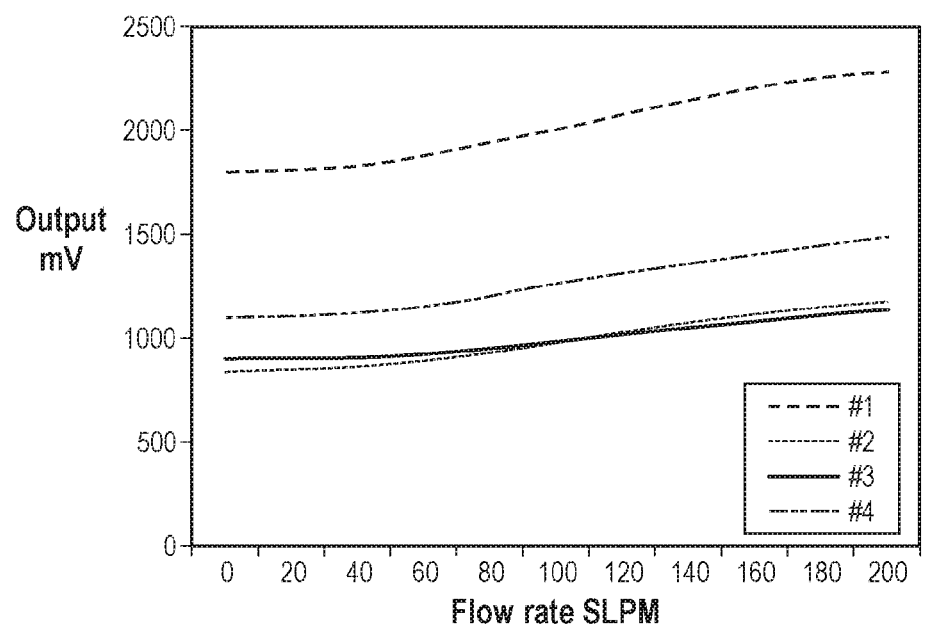
FIG. 10 is an output v. flow rate graph for different MDI formulations.

Providing feedback to users regarding their inhalation technique is one feature of the VHC that will help optimize drug delivery. In one embodiment, shown in FIGS. 3 and 9, a flow detector, configured as a flow sensor 34, is used to collect data and provide feedback about technique. The flow sensor measures the flow rate at which the user is inhaling. Inhaling too fast may deposit most of the drug in the throat rather than in the lungs. Effective drug deposition into the lungs may be achieved with controlled inhalation. In addition, the flow rate may be integrated over time to determine the volume of air inhaled, which may be used to provide the user with an indication of when they have emptied the interior space of the chamber housing and received a complete dose. As shown in FIGS. 3 and 9, the flow sensor 34 includes a 58 bypass channel with input and output ports 36, 38 communicating with the interior space. The pressure differential between the proximal and distal openings defined by the input and output ports creates a small flow rate through the bypass channel. A thermal mass air flow sensor 60 is used to measure the flow through the bypass channel, which is correlated to inhalation flow rates, as shown in FIG. 9. The flow sensor 34, 34' may be placed at either location shown in FIG. 9. The flow sensor measures the flow without being disposed in, or interfering with, the flow path in the interior space 4. As such, the flow sensor does not interfere with the aerosol medication or flow path through the interior space. The flow rate information may be combined with the MDI actuation detection and MDI identification, described in more detail below, to provide reliable insight to patient behavior and use of the device.

Figures 18, 19:
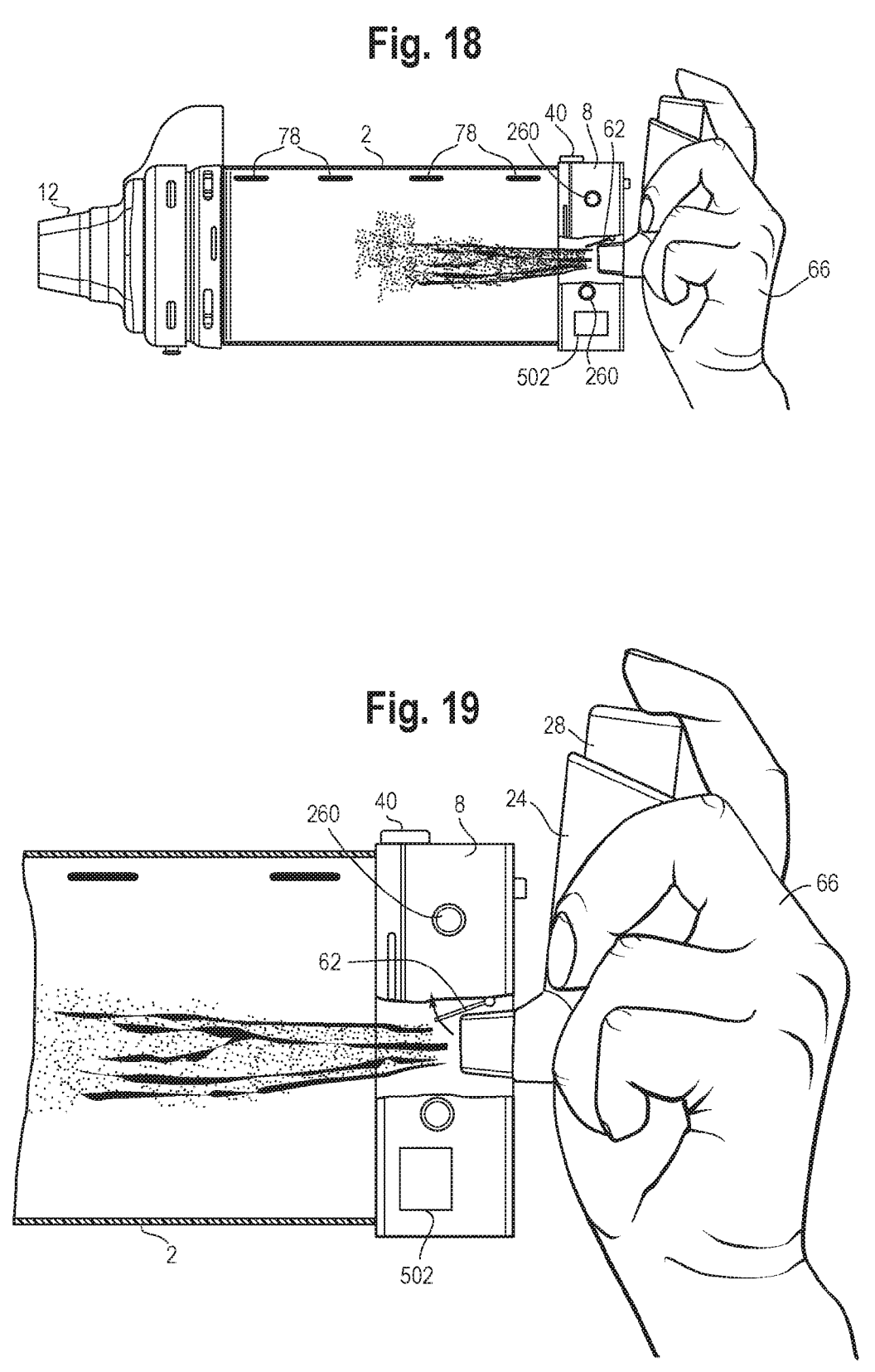

Referring to FIG. 12, the flow rate information may be used in real-time to provide feedback to the user about practice sessions, for example through a feedback device such as an indicator (visual, auditory and/or haptic) or display, and whether they should begin inhalation, and/or whether they need to slow down the flow rate, for example when exceeding a maximum flow rate. MDI actuation may also be used to provide feedback to the user about initiating actuation and/or beginning inhalation. First, the user 66 inserts the MDI into the backpiece as shown in FIG. 19. A contact switch 62, or other MDI insertion detector or sensor, detects the insertion. When the MDI is inserted, the smart VHC actively looks for MDI actuation and/or inhalation flow detection. Depending on the feedback through a feedback device (e.g., indicator or display), the user may actuate the MDI, dispensing an aerosolized medication into the interior space, with an actuation time stamp being recorded. The processor 502 then looks for inhalation flow, as communicated by the flow sensor 34, and records flow rate and a timestamp of active inhalation. The processor 502 also compares the inhalation rate with a stored predetermined rate, e.g., a maximum recommended flow rate, and provides feedback to the user if the inhaled flow rate exceeds the predetermined flow rate. The processor then compares the inhaled volume, as calculated from the flow rate, with the volume of the interior space 4, and notifies the user that the treatment is complete and the dose has been properly administered. Alternatively, the processor may communicate to the user that further inhalation is required to fully empty the interior space. As noted, the user has the option to practice using the device before the treatment begins. In this case, the MDI is not inserted. Rather, only the flow sensor is activated. The processor records the flow rate and provides feedback about the flow rate, and notifies the user that the practice is complete.

Figure 15:
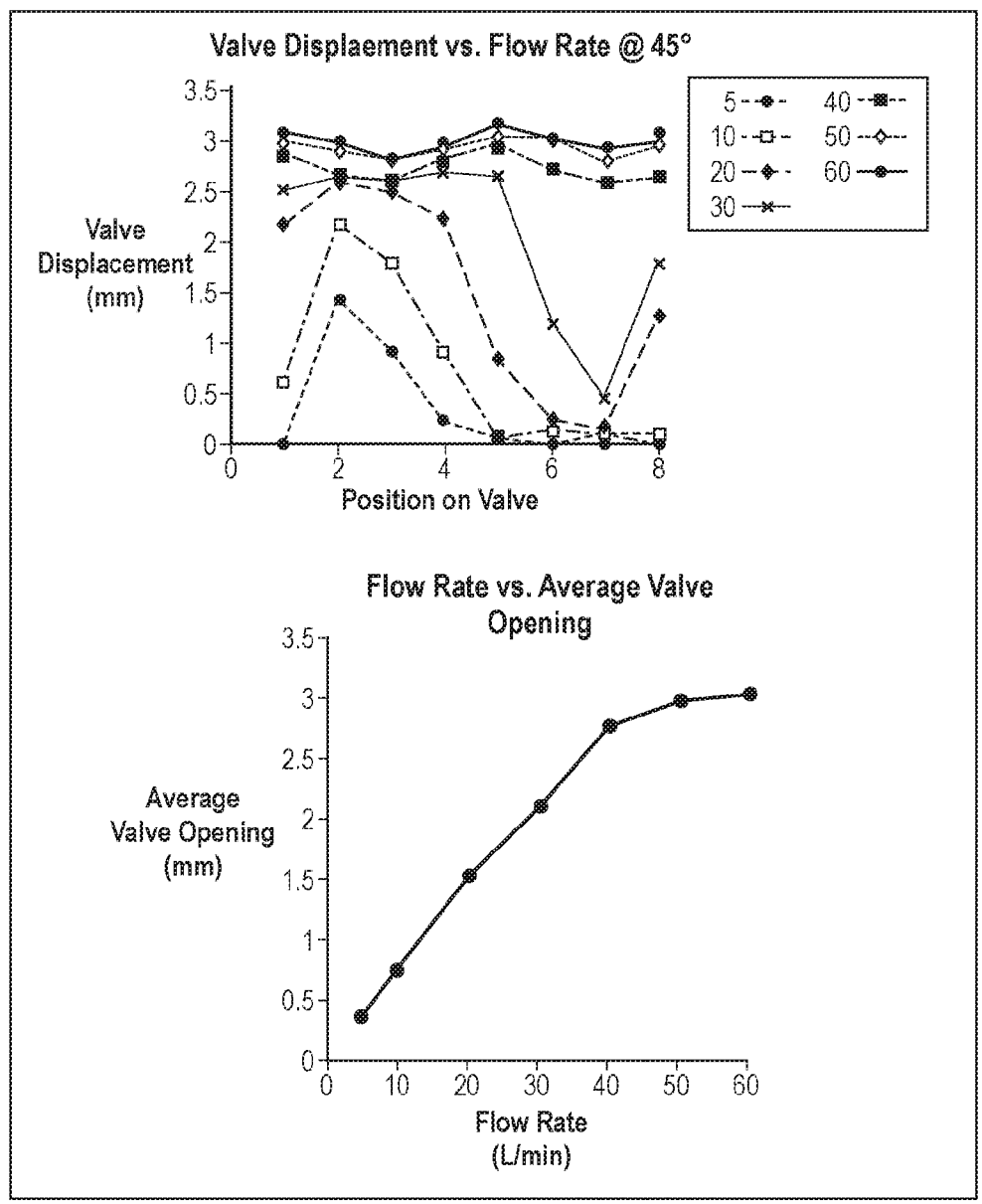
FIG. 15 are graphs showing correlation between the valve opening and flow rate.

Referring to FIGS. 14-17, one embodiment of a smart VHC includes a thin skin-like patch including a resistive strain gauge 68 mounted on the inhalation valve 16 to measure the valve opening 70 geometry during inhalation. The strain gauge may be applied to the valve with adhesive or by insert molding during injection holding of the valve. As shown in FIG. 15, the size and duration of the opening of the valve 16 may be correlated with the inhalation flow rate to confirm completion of inhalation.

Figure 16:
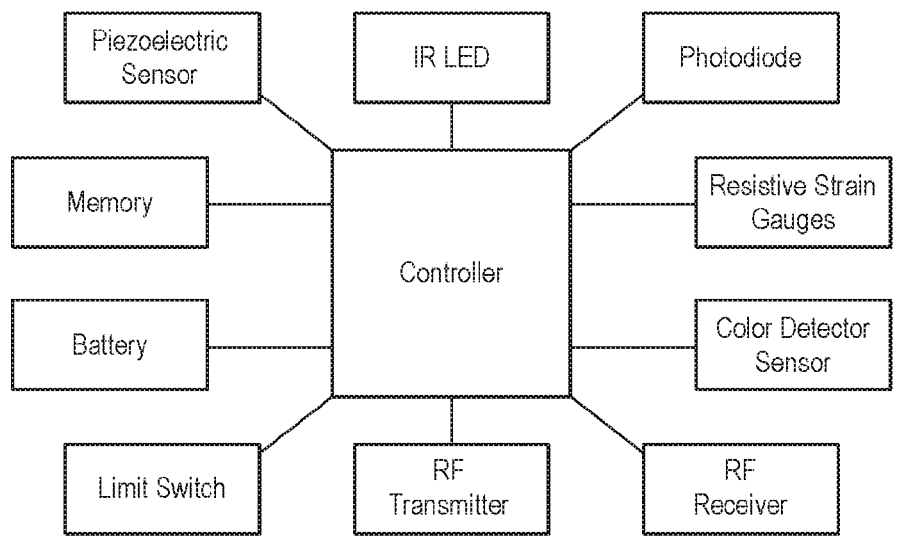
FIG. 16 is a schematic showing various controller inputs.
Figure 17:
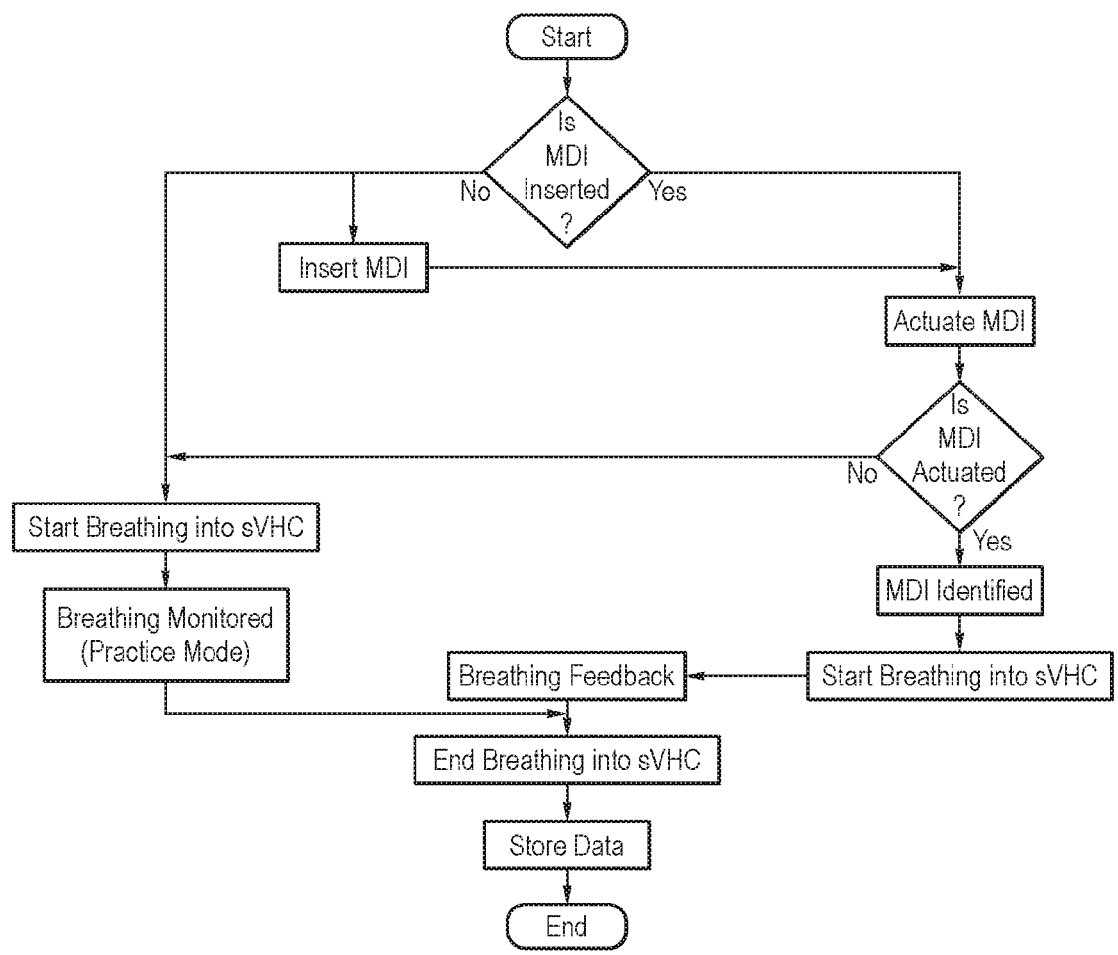
FIG. 17 is a flow chart illustrating MDI usage and feedback loops.

As shown in FIG. 16, a controller, which may be located on or inside the various embodiments of the smart VHC described herein, is in communication with one or more sensors, switches and or gauges that are tracking or controlling operation of the smart VHC. The controller may store data gathered in a memory for later download to a receiving device, or may transmit data to a receiving device in real-time. Additionally, the controller may perform some processing of the gathered data from the sensors, or it may store and transmit raw data. RF transmitter and/or receiver modules may be associated with the controller on the smart VHC to communicate with remote hand-held or fixed computing devices in real-time or at a later time when the smart VHC is in communication range of a communication network to the remote hand-held or fixed location computing devices. The controller may include one or more of the features of the computer system 500 shown in FIG. 83. Additionally, the one or more sensors, switches or gauges may be in wired or wireless communication with the controller.

For clarity in displaying other features of the various Smart VHC embodiments described, the controller circuitry is omitted, however a controller or other processing agent capable of at least managing the routing or storing of data from the smart VHC is contemplated in one version of these embodiments. In other implementations, the smart VHC may not include an onboard processor and the various sensors, gauges and switches of a particular embodiment may wirelessly communicate directly with a remotely located controller or other processing device, such as a handheld device or remote server. Data gathered by a controller or other processing device may be compared to expected or pre-programmed values in the local controller memory or other remote location to provide the basis for feedback on whether desired performance or therapy is taking place. If the controller is a more sophisticated and includes more of the computer 500 elements described in FIG. 83, then this processing may all be local to the smart device (smart VHC, smart MDI, etc.). In more rudimentary controller arrangements, the data may simply be date/time stamped and stored locally or remotely for later processing. In one embodiment, the data may further be locally or remotely stamped with a unique device or patient identifier.

Breath-hold may also be one particular step to facilitate diffusion of the drug and optimize deposition within the lungs. The user's breath-hold may be monitored using methods below or the user may simply be encouraged to hold their breath visually or audibly without monitoring breath-hold directly.

Figure 86:
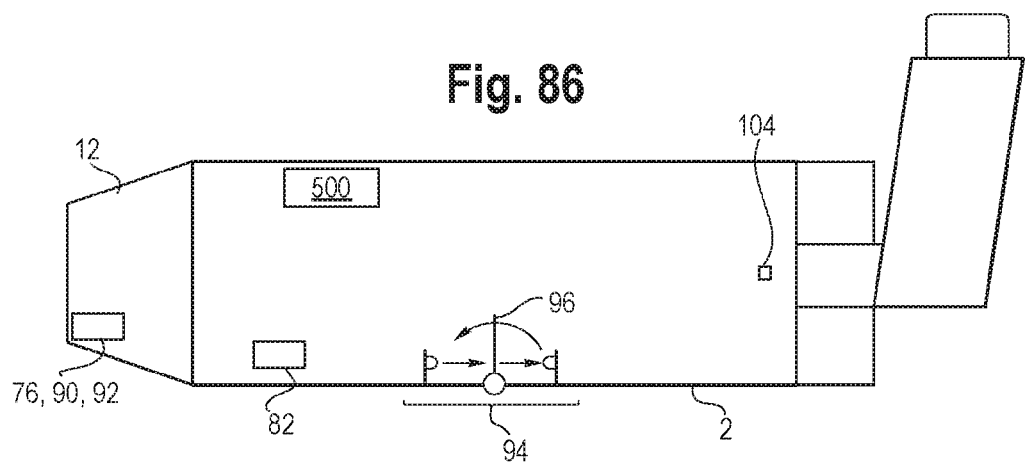
FIG. 86 is a view of a smart VHC and MDI.

1. Carbon Dioxide Detection 1.1. Referring to FIG. 86, carbon dioxide is a byproduct of cellular respiration which is expelled from the body through exhaled breath. As a result, the concentration of carbon dioxide in exhaled breath is significantly higher than the concentration of ambient air. Using a carbon dioxide sensor 76, the carbon dioxide concentration within the mouthpiece and mask adapter portions of the VHC may be monitored with higher concentrations indicating the expiratory phase of the user's breathing cycle. Combining this data with inspiratory flow data or other means of detecting the user's inhalation, breath-hold duration can be determined and used to provide feedback to the user. The end of inhalation may be determined, for example, using a flow or pressure threshold. Once the inspiratory flow or pressure falls below this threshold, the breath-hold timer can start and it will not stop until a spike in carbon dioxide concentration is detected.

Figure 20:
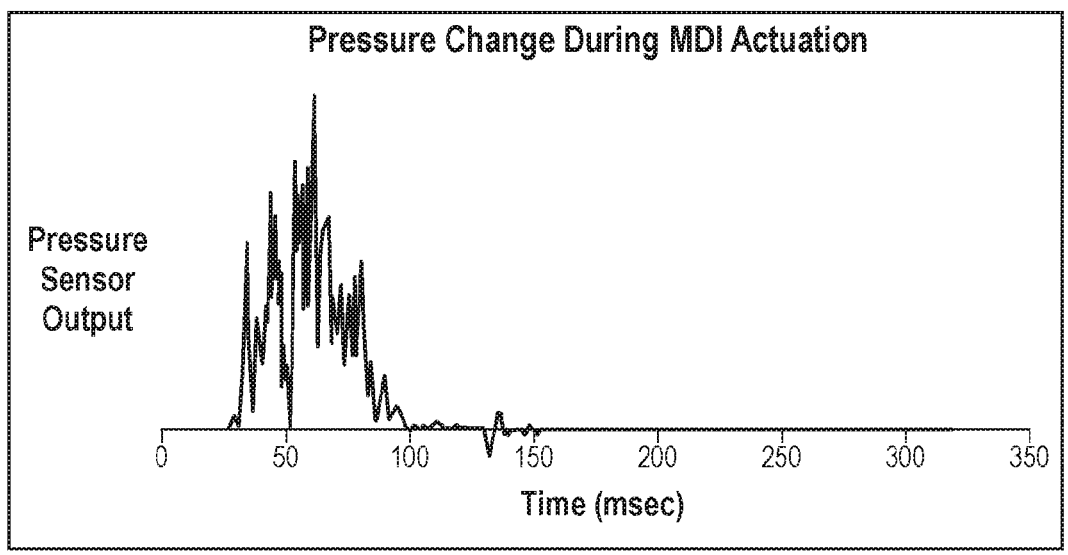
FIG. 20 is a pressure sensor output v. time for a MDI actuation.
Figure 21:
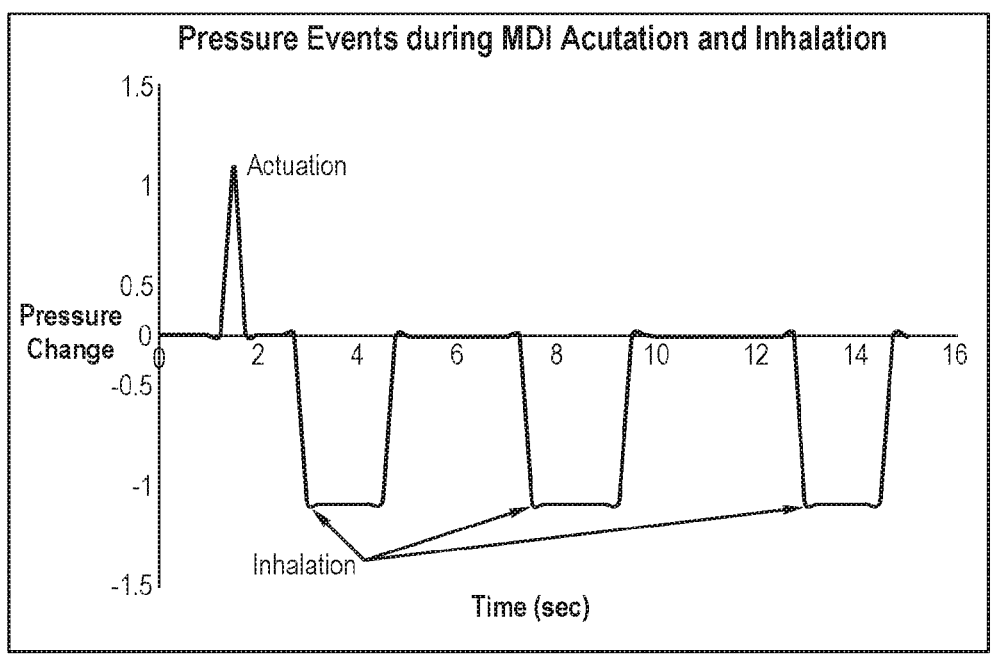
FIG. 21 is a pressure change v. time graph during MDI actuation and inhalation.

2. Pressure Monitoring 2.1. Referring to FIGS. 18-20, a pressure sensor 78 may be positioned within the mouthpiece/mask adapter or chamber housing, such that inhalation and exhalation phases of the user's breathing cycle may be monitored. Inspiratory and expiratory pressure thresholds may be used in order to calculate the duration of the user's breath-hold. When the inspiratory pressure falls below the inspiratory threshold, the breath-hold timer begins and once exhalation begins and the expiratory pressure threshold is exceeded, the breath hold timer stops. The pressure sensor 78 communicates with the computer 500 and processor 502.

In addition, the device provides information about when the chamber is empty by assuming a tidal volume and counting the number of inhalation breaths. The assumed tidal volume may be based on age and sex, and may be selected during setup. Since the volume of the interior space 4 is known, the computer/processor 500, 502 processes positive pressure events to identify when the MDI has been actuated, then counts the number of negative pressure events, which indicate inhalation, until the chamber volume has been reached. Each negative pressure event should be spaced apart a normal breathing cycle, e.g., 2-5 seconds, with the chamber volume being evacuated within a finite total treatment time period. If this is satisfied, a determination is made that the drug was fully delivered. Otherwise, feedback may be provided to the user to continue inhalation and/or the breathing cycle. Feedback may be audible, visual or tactile/haptic (e.g., vibratory), or any combination thereof using the various indicators described herein elsewhere. The information may be logged and stored, and/or feedback provided that additional training is needed.

Figure 24:
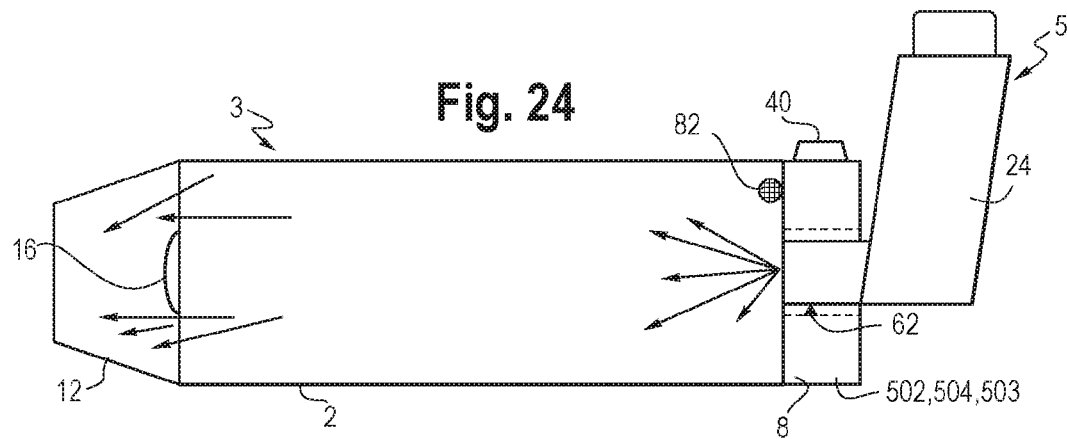
FIG. 24 is a side view of another embodiment of a smart VHC.

3. Microphone 3.1. Inhaled and exhaled air travel different paths through the VHC during use. Since different flow paths are used, it is possible that flow through these paths will sound different from one another. A microphone 82, as shown for example in FIG. 24, may be used to listen for inhalation and exhalation and may be used to calculate breath-hold durations using a threshold method similar to embodiments 1.1 and 2.1.

Figure 26:
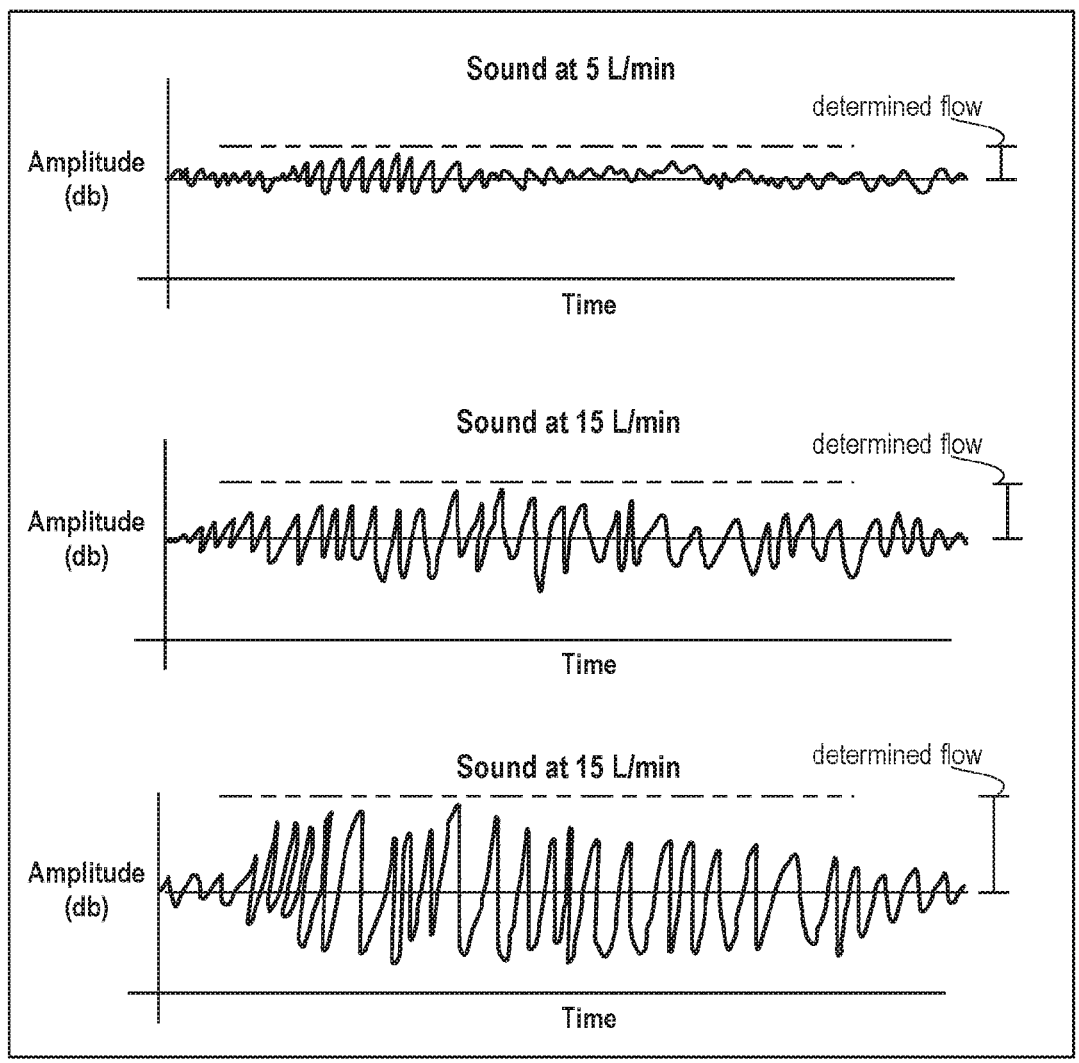
FIG. 26 are graphs showing amplitude v. time at different flow rates.

In addition, during treatment, and once the MDI has been actuated, the microphone(s) record the sound of air flow through the VHC and, based on the amount of turbulence recorded by the microphone, may be monitored and analyzed by the microprocessor. For example, the amplitude of the translated sound over a period of time correlates to a specific flow rate, or range of flow rates, as shown in FIG. 26. The VHC may provide feedback, by way of an indicator (visual, auditory, tactile, etc.) to the user that the inhalation rate is excessive, or exceeding a predetermined maximum flow rate. Other feedback may include information that the treatment is complete or that a data upload is complete. Upon completion of treatment, the system is reset and ready for another MDI actuation.

Figure 58:
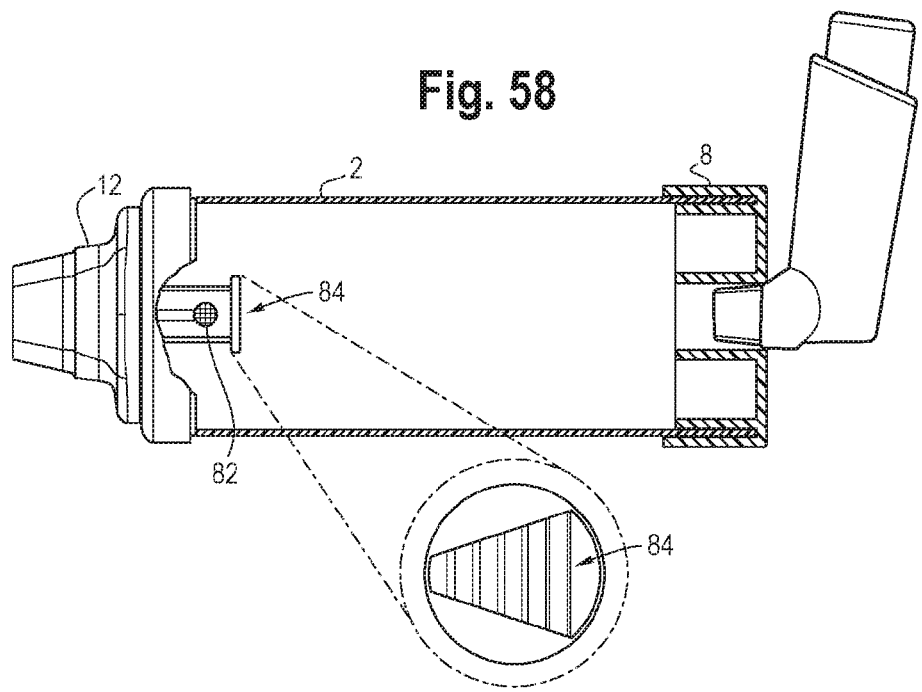
FIG. 58 is a side view of one embodiment of a VHC.
Figure 59A:
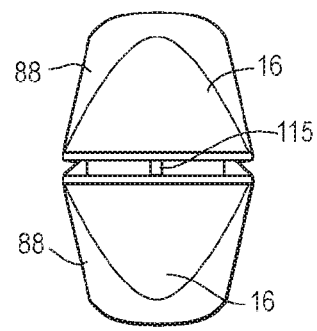
FIGS. 59A-C are various views of a duckbill valve with a vibrating beam.
Figure 59B:
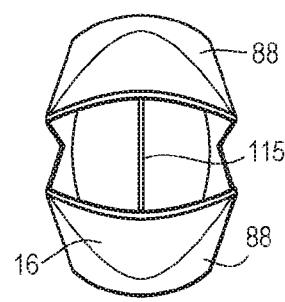
Figure 59C:
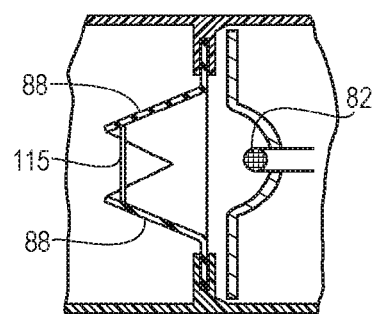

Referring to FIG. 58, a reed, or an array or series of reeds 84, e.g., plastic or silicone, may be disposed adjacent the microphone 82. Differential flow activates or creates different acoustical outputs from the reed(s), which may be picked up and recorded by the microphone 82. As shown in FIGS. 59A-C, a single reed 115, or beam, may be disposed across the mouth of a valve, shown as a duckbill valve. As the flaps 88 of the valve are opened or closed different amounts, e.g., in response to the flow rate, the reed 115, which acts as a vibrating string, is made thinner or thicker, such that it produces different acoustical signals that may be picked up by the microphone 82. The microphone communicates with the computer 500 and processor 502.

4. Humidity Sensor 4.1. Air from the ambient environment becomes saturated with water vapor when it enters the lungs. When this air is exhaled, it passes through the mouthpiece and mask adapter where the humidity of the air can be analyzed. By continuously monitoring humidity levels with a sensor 90 as shown in FIG. 86, in the mouthpiece and mask adapter, the exhalation phase of the breathing cycle may be detected and used to determine breath-hold duration in a similar manner as embodiments 1.1 and 2.1. The humidity sensor 90 communicates with the computer 500 and processor 502.

5. Temperature Sensors 5.1. As ambient air enters the body, it is warmed to body temperature. Using a temperature sensor 92 (see, e.g., FIG. 86), air temperature may be monitored in the mouthpiece and mask adapter. When an abrupt rise in temperature is seen, it may be interpreted as an exhalation from the user. Similar to previous breath-hold detection embodiments, combining this detection of the beginning of exhalation with inspiratory measurements (i.e. flow or pressure), breath-hold duration may be calculated and fed back to the user for technique improvement. The temperature sensor 92 communicates with the computer 500 and processor 502.

Figure 63:
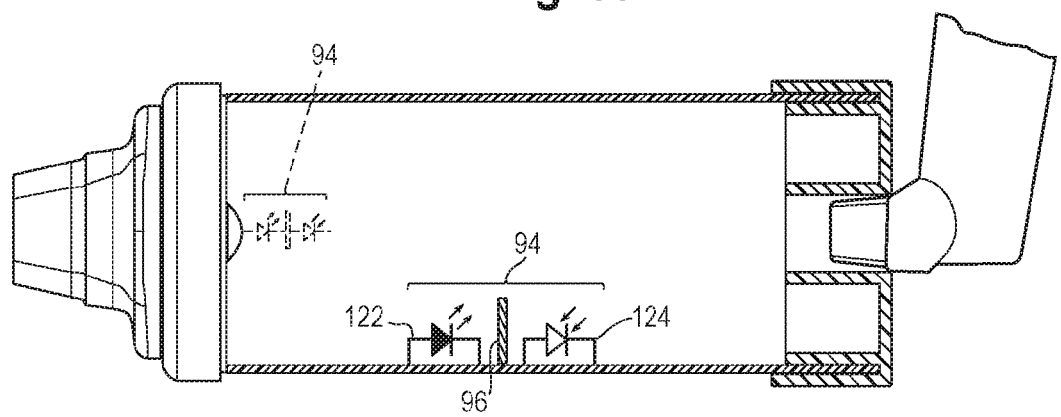
FIG. 63 is a side view of one embodiment of a VHC.

6. Light Curtain 6.1. Referring to FIGS. 63 and 86, a light curtain 94 or plurality of light curtains may be used in conjunction with a flexible member 96 which responds to negative and positive pressures. During inhalation, the flexible member may be drawn in a direction such that one of the pair of light curtains has its light beam broken (or restored) and this may be interpreted as an inhalation by the user. In contrast, the flexible member may be forced in an opposite direction during exhalation where the second of the light curtains has its beam broken (or restored). This is interpreted as the user's exhalation. Using these measurements, the time in which both light curtains are unbroken indicates the breath-hold duration. Alternatively, a single light curtain may be used to detect exhalation by the user and another method (e.g. inspiratory pressure or flow threshold) may be used to determine the end of inhalation.

6.2. In another embodiment, the moisture in the user's exhaled breath may be sufficient to break the light curtain responsible for detecting exhalation in which case, no flexible member is needed.

End of Treatment

When receiving aerosol from a valved holding chamber, particularly for mask products in the infant and baby populations, one uncertainty is knowing at what point the user has received all of the medication from the chamber. Premature chamber removal may lead to under-dosing as will excess mask leakage during aerosol administration. By monitoring the aerosol within the chamber or the volume of air inhaled through the chamber, feedback may be given to the user regarding end of treatment. This provides dose assurance to all parties involved in the patient's health.

1. Capacitance Change 1.1. Assuming the aerosol has a different dielectric compared to that of air, a change in capacitance of the capacitor 106 shown in FIGS. 43 and 44 may be used to detect when all aerosol has vacated the chamber. A baseline capacitance would be measured prior to aerosol actuation and treatment would not end until the capacitance returned to this baseline value or some similar value.

Figure 7:
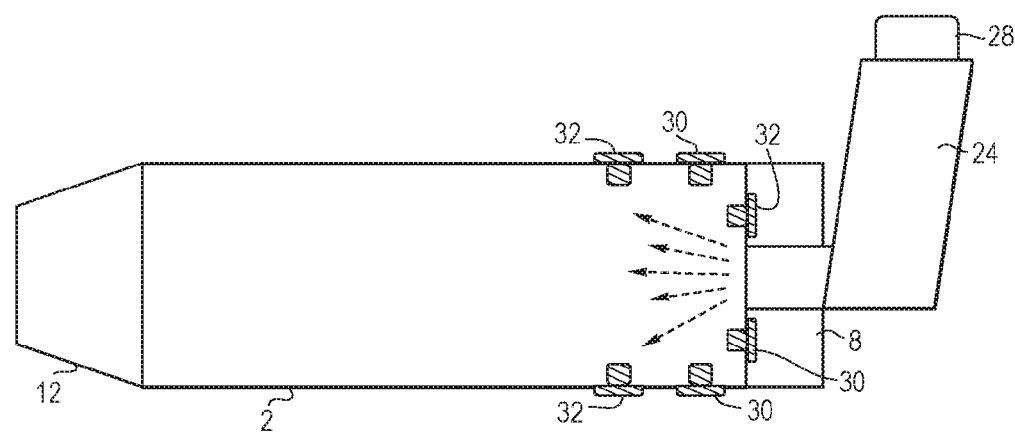
FIG. 7 is a side view of various alternative embodiments of a smart VHC.

2. Light Transmission/Reflection 2.1. As shown in FIGS. 3 and 7, a light source 30 and photodetector 32 may be set up in any orientation relative to the flow with the light source aimed directly at the photodetector or reflected off of a surface towards the photodetector. When aerosol is present, this light is scattered, diffused, refracted, absorbed and reflected so that the amount of light returning to the photodetector is reduced. End of treatment occurs when the baseline readings are approached.

Flow Detection

Aerosol deposition in the throat and upper airway may occur when flow rates get too high leading to side effects as well as depriving the lung of medication. The smart VHC should have a feedback device or feature informing the user if the predetermined, maximum recommended flow rate has been exceeded, using a flow detector, and allowing the user to slow their inhalation to an effective rate. All embodiments of the flow detectors, alone or in combination, as described below may be used for this purpose, in addition to helping determine end of treatment. End of treatment is determined by integrating these flow rates overtime until a threshold volume has been reached, as shown in FIG. 12. The threshold volume is chosen such that all aerosol is inhaled from the chamber.

3. Pressure Sensors 3.1. Differential Pressure Across A Valve

Figure 46:
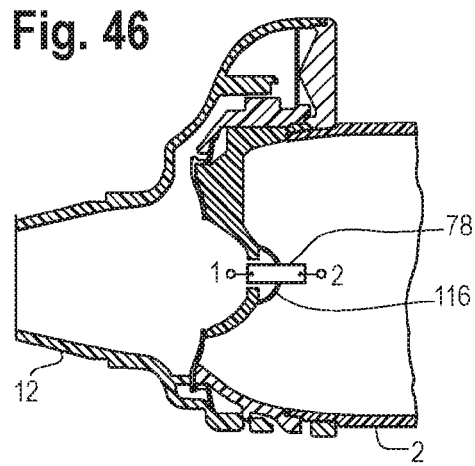
FIG. 46 is a partial, cross-sectional view of one embodiment of a smart MDI.

A valve is chosen such that its resistance is consistent, has low hysteresis and is preferably linear, as shown in FIG. 46. The flow through the valve can then be inferred based on the differential pressure reading across the valve.

3.2. Differential Pressure Across MDI 3.2.1. MDI Boot

Figure 47:
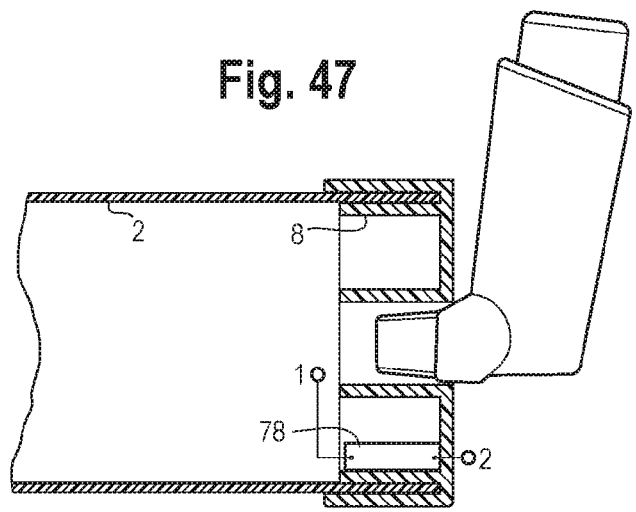
FIG. 47 is a partial, cross-sectional view of one embodiment of a smart MDI.

An MDI identifier is used to identify the MDI being used with the chamber. Assuming this information is known, the MDI's resistance profile (pressure vs. flow curve) can be accessed from a predefined database and using a differential pressure measurement comparing the pressure at the mouthpiece of the MDI as detected by a pressure sensor 78 to atmospheric pressure, as shown in FIG. 47, the flow through the MDI itself can be calculated.

3.2.2. Molded MDI Adapter Boot (Canister Inserted)

Since most MDI will have different resistance profiles from one another, the canister may be removed from the boot and placed into a built in receptacle molded into the MDI adapter, or backpiece. This adapter would allow all MDI canisters to be inserted and for aerosol to enter the chamber. The resistance to flow of the MDI adapter can then be designed specifically to the system's needs, that is, linear P0 curve, low hysteresis and consistent from part to part.

3.3. Differential Across an Orifice in a Bypass 3.3.1. As shown in FIGS. 3, 9, 49 and 50, a bypass channel 60 exists on the inside of the chamber wall or mouthpiece/mask adapter and this channel is in fluid communication with the aerosol chamber. During inhalation, some flow is drawn through this bypass channel and through an orifice 110 of precisely controlled size. The resistance to flow of this orifice can be thoroughly characterized and measurements of differential pressure using a pressure sensor 78 across the orifice 110 may be used to calculate flow though the orifice and bypass channel. Flow rates through the chamber will be calibrated to the flow through the bypass channel such that bypass flow measurements during use can indicate total flow through the VHC. The pressure sensor 78 communicates with the computer 500 and processor 502.

3.4. Venturi 3.4.1. A venturi 112 uses a local constriction of the flow path to accelerate the fluid as it passes through. As the fluid velocity increases, its pressure decreases relative to that of the slower moving fluid upstream of the constriction. A differential pressure sensor can detect this difference and with knowledge of the venturi geometry, flow rate can be calculated.

Figure 51A:
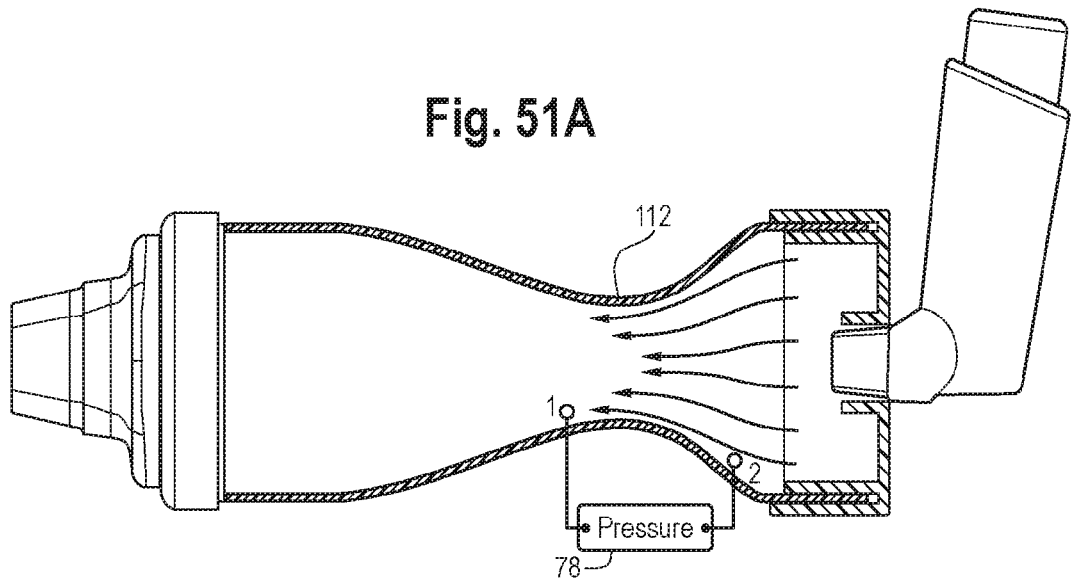
FIGS. 51A-C are various side views of alternative VHC embodiments.
Figure 51B:
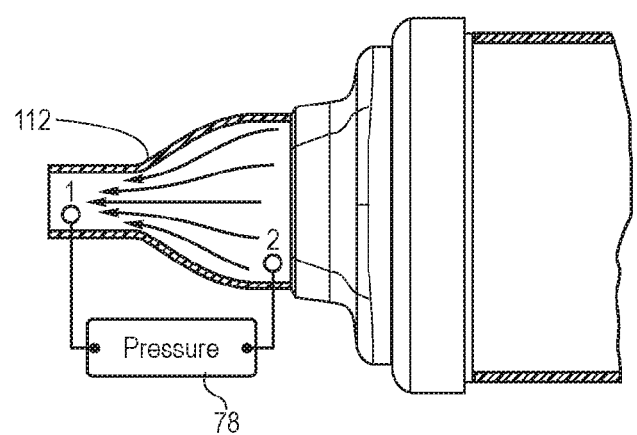
Figure 51C:
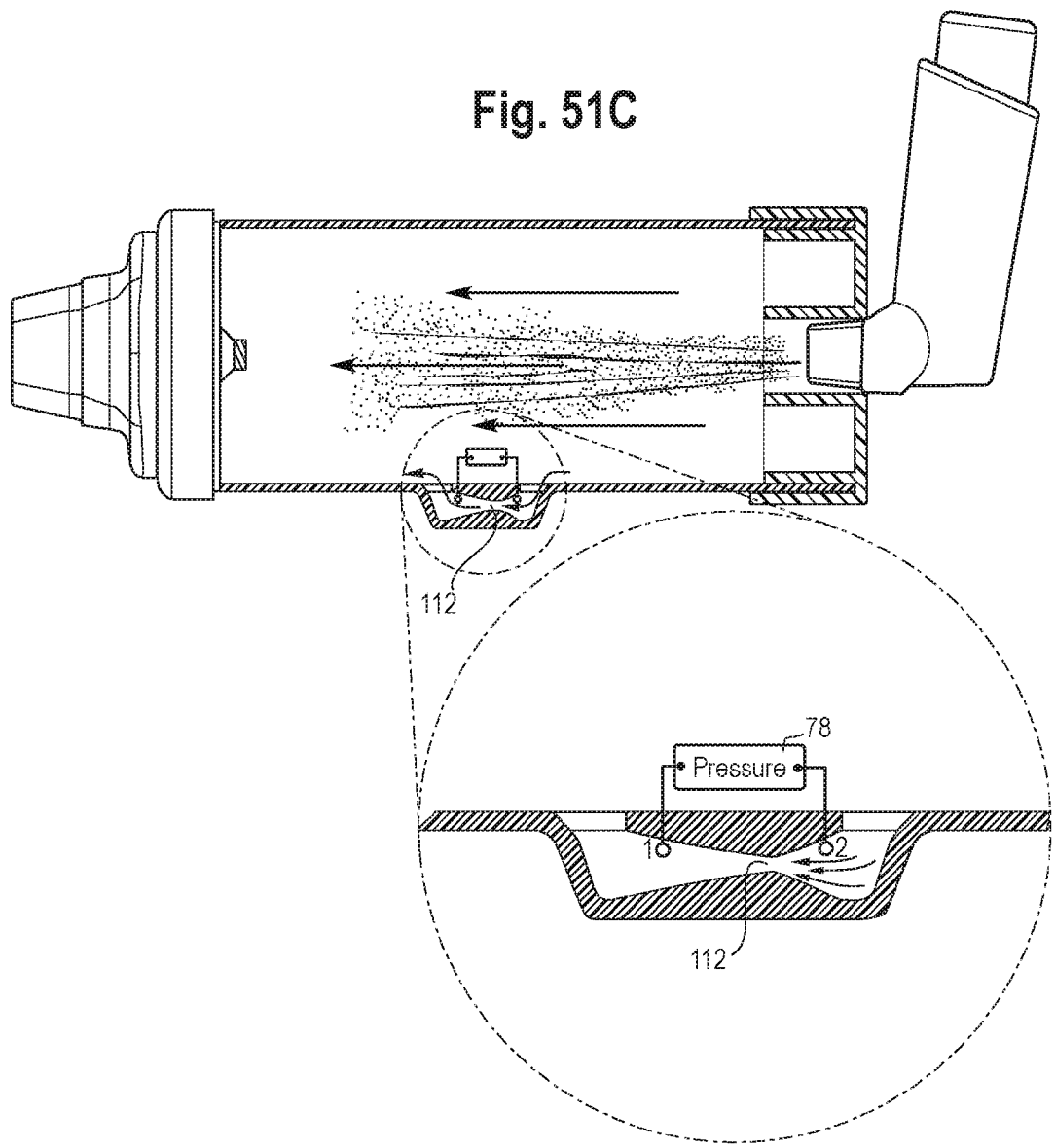

The venturi 112 can be molded as part of the chamber housing 2, as a part of the mouthpiece 12 or as part of a bypass flow path 60 as shown in FIGS. 51A-C respectively. The pressure sensor 78 communicates with the computer 500 and processor 502.

3.5. Pitot Static Tube 3.5.1. Pitot static tubes 114 consist of a tube with one closed end and means of comparing the pressure within the tube to the surrounding fluid pressure. As the fast moving air enters the Pitot tube 114, it stagnates and builds a pressure within the tube that is proportional to the initial speed of the fluid flow.

Figure 52:
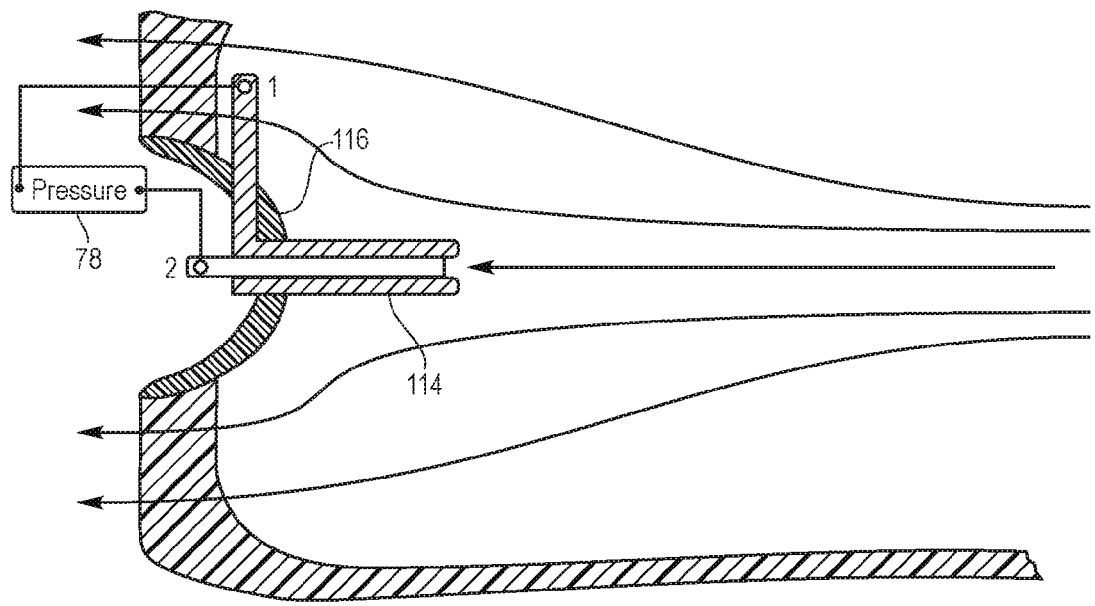
FIG. 52 is a partial, cross-sectional side view of one embodiment of a VHC.

A pitot tube may be molded in or assembled onto a baffle 116 of the valved holding chamber so as to sample the fastest moving air during inhalation as shown in FIG. 52. This velocity can be turned into a flow rate estimation with knowledge of the chamber geometry. A pressure sensor 78 detects the pressure differential and communicates with the computer 500 and processor 502.

4. Sound-Based Methods

For all sound-based methods, a second microphone may be used to detect ambient noise. This information can then be used for noise reduction in the signal being processed by the microcontroller or other processor 502.

4.1. Volume Based 4.1.1. Intrinsic Sounds

As air rushes through the MDI and valved holding chamber, turbulence is generated which produces sound. At higher flow rates, more turbulence is generated and louder sounds are present. Monitoring the volume of sound within the chamber can provide a means of estimating flow rate although non-filtered volume-based methods would be highly vulnerable to environmental noise.

A microphone 82 is placed in the interior space of the chamber housing, for example as coupled to an adapter or the backpiece (see, e.g., FIG. 24), or along the chamber or at the baffle (see e.g., FIG. 59C). This same microphone may be used for MDI actuation detection.

4.1.2. Sound Generation

A microphone is placed in a similar spot as in embodiment 4.1.1. As shown in FIGS. 58 and 59A-B, a vibrating reed 115 or reeds 84, edge tones or flow over an open or closed tube may be used to generate sound as flow passes over and this volume should be substantially larger than those present in the chamber itself. The microphone 82 communicates with the computer 500 and processor 502.

4.2. Low Pass, High Pass and Band Pass Filter Volume Based

As mentioned in embodiment 4.1.1., volume based methods may be vulnerable to false readings due to ambient noise. To reduce this risk, digital and/or analog filtering may be implemented so that the system is only effectively "listening" to particular frequency bands. These filters would be selected such that the sounds intrinsic to the chamber are listened to or in the case of the sound generation, these frequencies are monitored.

4.3. Algorithm Based

The sounds coming from the chamber at different flow rates, whether these sounds are intrinsic to the product or produced by means of a reed or other sound generating source, will be fairly unique to the system. Various algorithms may be used to quantitatively compare the incoming microphone signal to a range of signals that have been pre-recorded at defined flow rates from within the device.

4.4. Acoustic Time Of Flight (TOF)

Figure 64:
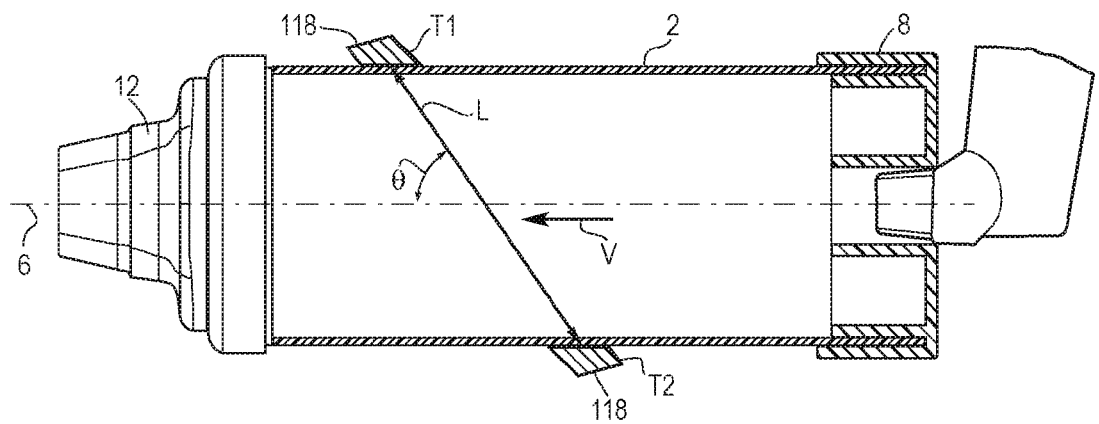
FIG. 64 is a side view of another embodiment of a VHC.
Figure 65:
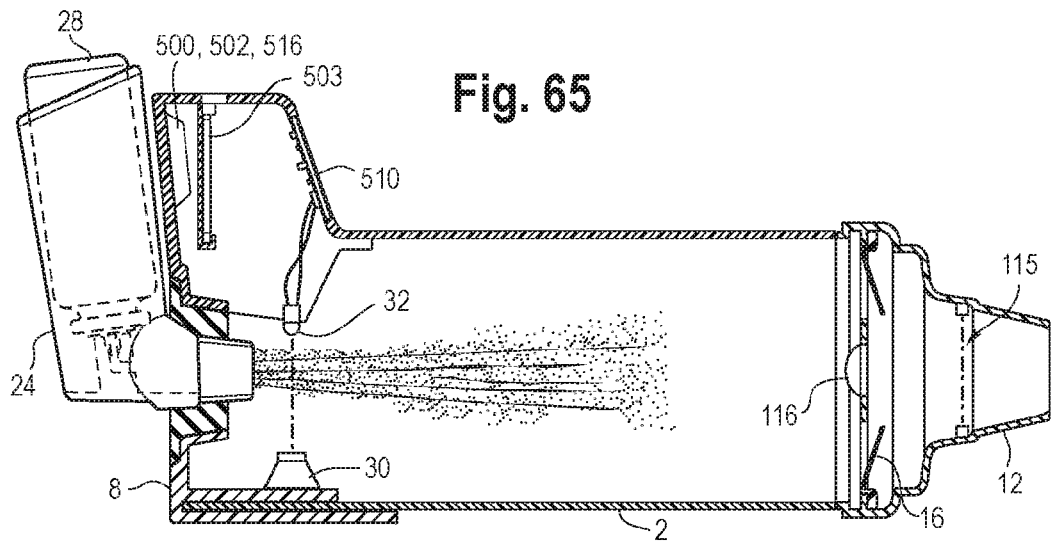
FIG. 65 is a side view of another embodiment of a VHC.
Figure 66A:
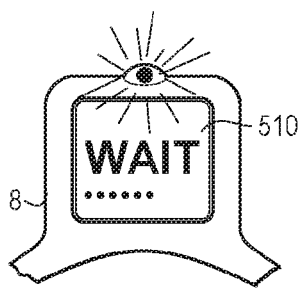
FIGS. 66A-C are various graphical displays with user indicia.
Figure 66B:
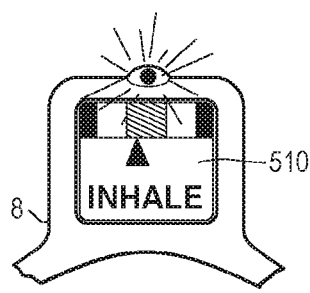
Figure 66C:
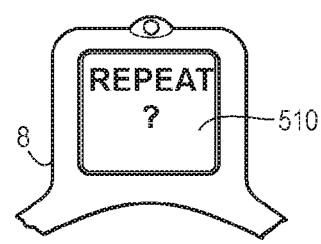
Figure 67:
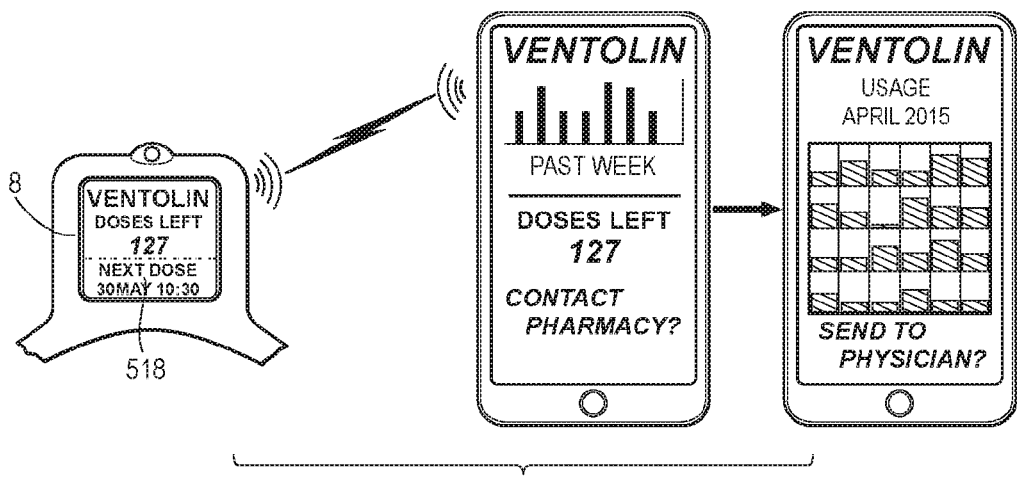
FIG. 67 is a pictorial showing communication between a smart VHC and user interface.
Figure 68:
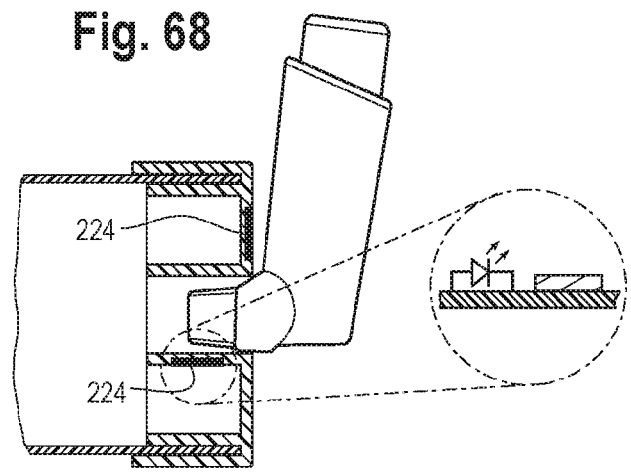
FIG. 68 is a partial, cross-sectional side view of a MDI inserted into a VHC.

Referring to FIG. 64, acoustic TOF, in this case, refers to the time it takes for sound to travel from one sound transceiver 118 to another. Transceiver one (T1) is located downstream of transceiver two (T2) which may both be situated inside or outside of the chamber. As sound travels from T1 to T2, it is effectively slowed down as a result of travelling against the air flow through the chamber. Conversely, as sounds travels from 12 to Ii, it does so faster than normal as it is moving with the flow. Knowing the angle θ of the transceivers 118, or ultrasonic transducers, relative to the direction of flow as well as the TOF from 11 to 12 and 12 to T1, the average flow velocity and therefore flow rate can be estimated with knowledge of the chamber geometry. Sound of any frequency can work although it would be desirable to be outside of the human audible range (>20 kHz). The transceivers 118 communicate with the computer 500 and processor 502.

4.5. Doppler

Doppler ultrasound uses the shift in frequency of a reflected wave relative to the transmitted wave to infer the speed at which the reflecting body is moving. Using the suspended aerosol particles as reflecting bodies, the Doppler principle may be used to determine average particle velocity and estimate flow rate. This method would only detect flow when aerosol is present so it may also be used as a further dose assurance tool.

Figure 53:
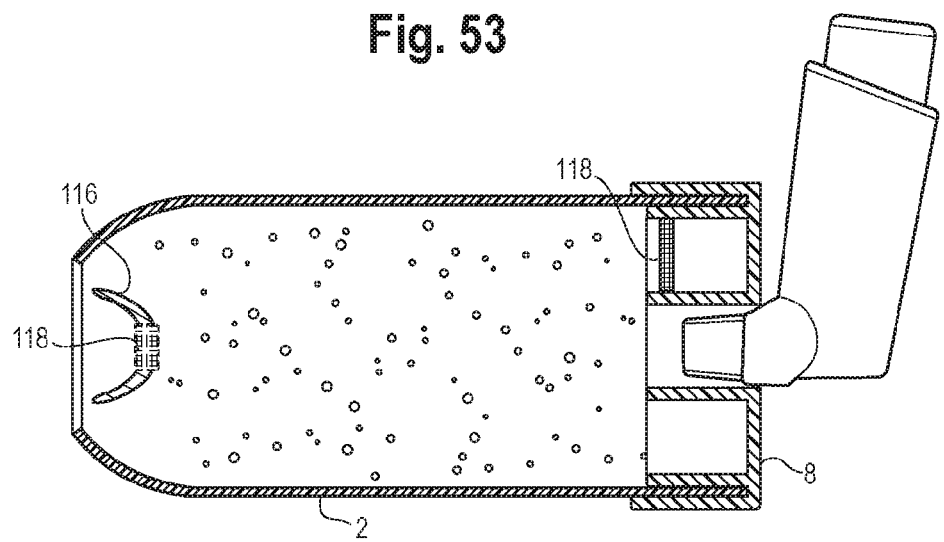
FIG. 53 is a partial, cross-sectional side view of one embodiment of a VHC.
Figure 54:
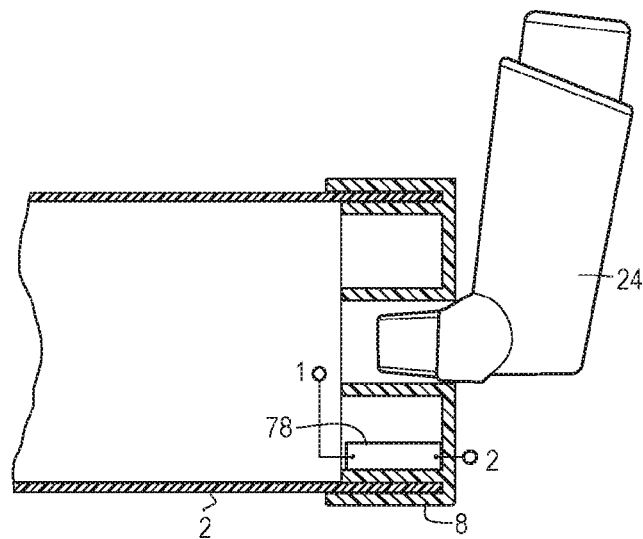
FIG. 54 is a partial, cross-sectional side view of one embodiment of a VHC.
Figure 55:
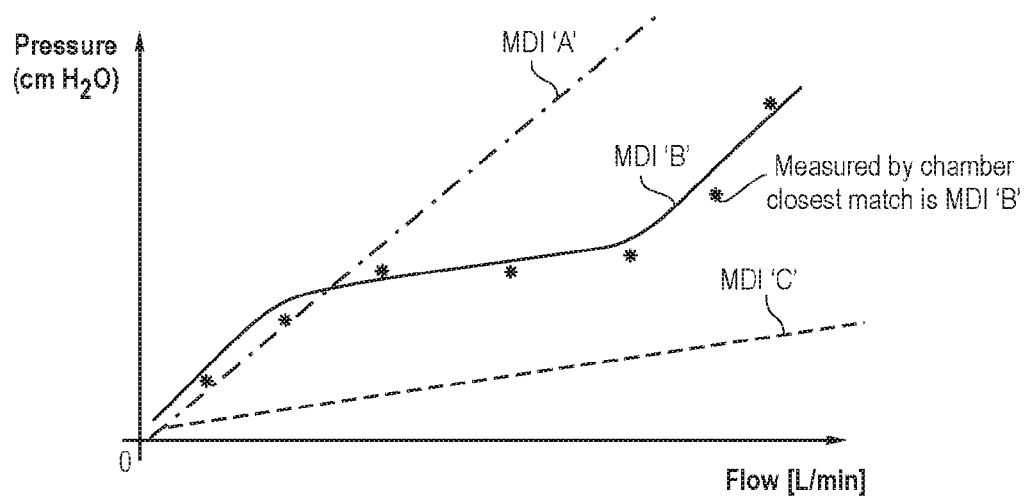
FIG. 55 is a pressure v. flow graph of various MDI devices.

As shown in FIG. 53, an ultrasonic transducer 118 may be placed in the baffle 116 with sound directed towards the MDI adapter or backpiece 8, in the MDI adapter with sound directed towards the baffle or anywhere in between as long as the sound production is not perpendicular to the direction of airflow. The transceiver/transducer 118 communicates with the computer 500 and processor 502.

5. Light-Based Methods 5.1. Internal Reflection in a Valve with a Slit

Figure 56:
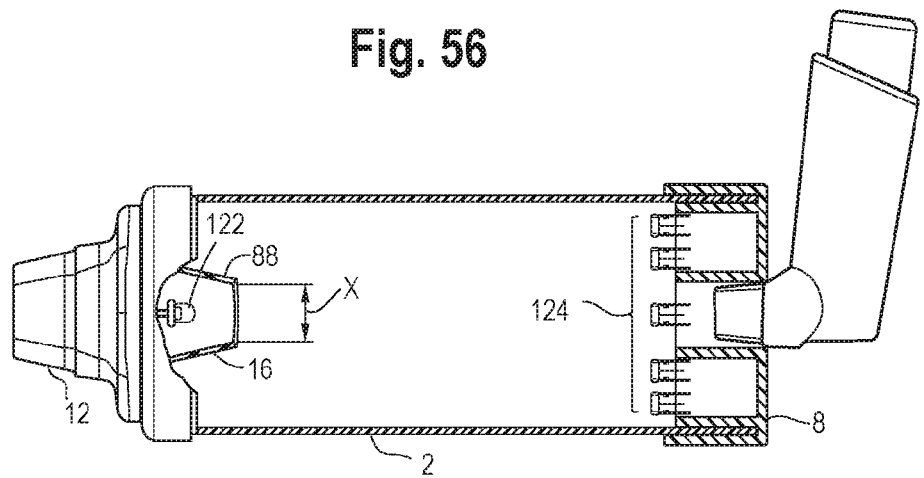
FIG. 56 is a side view of one embodiment of a VHC.
Figure 57:
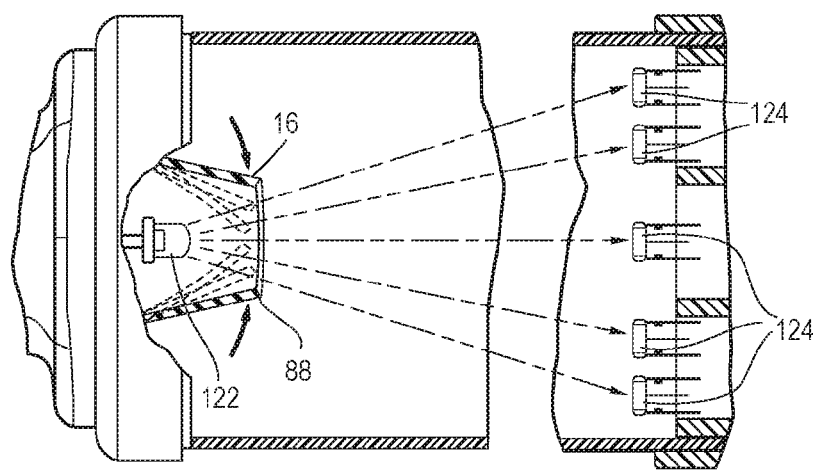
FIG. 57 is an enlarged partial side view of the VHC shown in FIG. 56.
Figure 60:
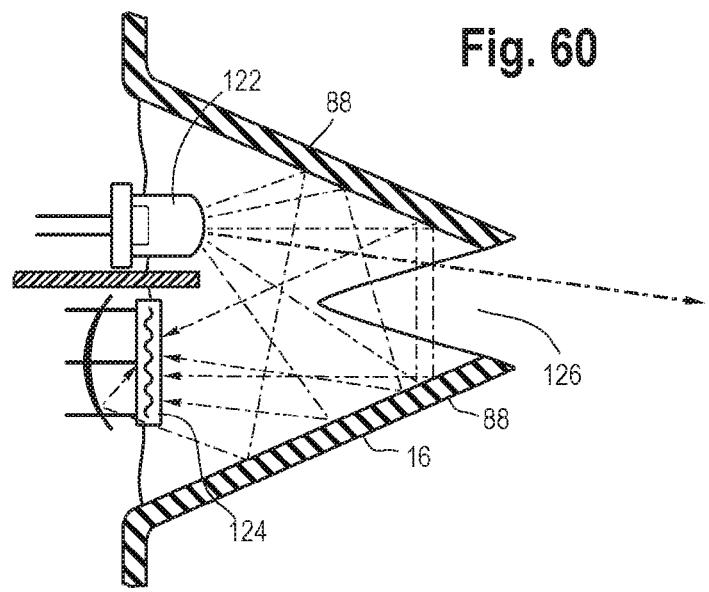
FIG. 60 is a partial, cross-sectional side view of one embodiment of a flow rate sensor assembly.

Referring to FIG. 60, a light-emitting diode (LED) 122 or other light source and/or a photodetector 124 sensitive to the wavelength of light coming from the LED are positioned within a valve 16 with both directed towards the valve opening 126. The valve is of the type with a variable sized opening whose opening size is dependent on the flow rate passing through the valve. Duckbill, cross valves and any die cut valves are good examples however this list is not exclusive. Referring to FIGS. 56 and 57, the photodetectors 124 may be positioned externally of the valve.

During operation, the light source illuminates the inside/backside of the valve 26 which in turn reflects some of the light back to the photodetector as shown in FIG. 60, or lets light through to be received by the photodetectors as disclosed in FIGS. 56 and 57. When the valve is closed, most of the light coming from the source is reflected back to the photodetector (internal) or is not received by the photodetector (external). As the valve opens, more of this light is able to escape and as a result, less light is reflected back to the photodetector (internal), or conversely is received by the photodetectors (external). Through monitoring the signal coming from the photodetector, the degree to which the valve is open can be estimated along with the flow passing through the valve. The valve may be designed in such a way using shape and color as to focus the reflected light on the photodetector to certain degrees of its opening. The photodector 124 communicates with the computer 500 and processor 502.

A physical shielding may be positioned within the valve. The LED can have an adjustable brightness so that during an initial calibration phase, the same baseline signal is achieved through increasing the brightness of the LED iteratively with feedback from the photodetector or choosing a wavelength of light that is not readily absorbed by the drugs used. Any wavelength may be used in this method although a wavelength that is minimally absorbed or reflected by the aerosol is preferred. A high pass filter may also be implemented to remove any signal contribution coming from DC power sources (flash lights, sunlight) as well as low frequency electrical lighting such as the 60 Hz (120 Hz) lights in North America and the equivalent frequencies around the world.

Alternatively or in addition to high pass filtering, the light source's brightness may be varied at a particular frequency and using frequency detection algorithms, this signal could be analyzed for flow. In this case, the amplitude of the frequency component of the signal that matches the frequency of the light source will decrease and increase as the valve opens and closes, respectively.

5.2. Shine Through in a Valve with a Slit 5.2.1. External Light Source

Figure 61:
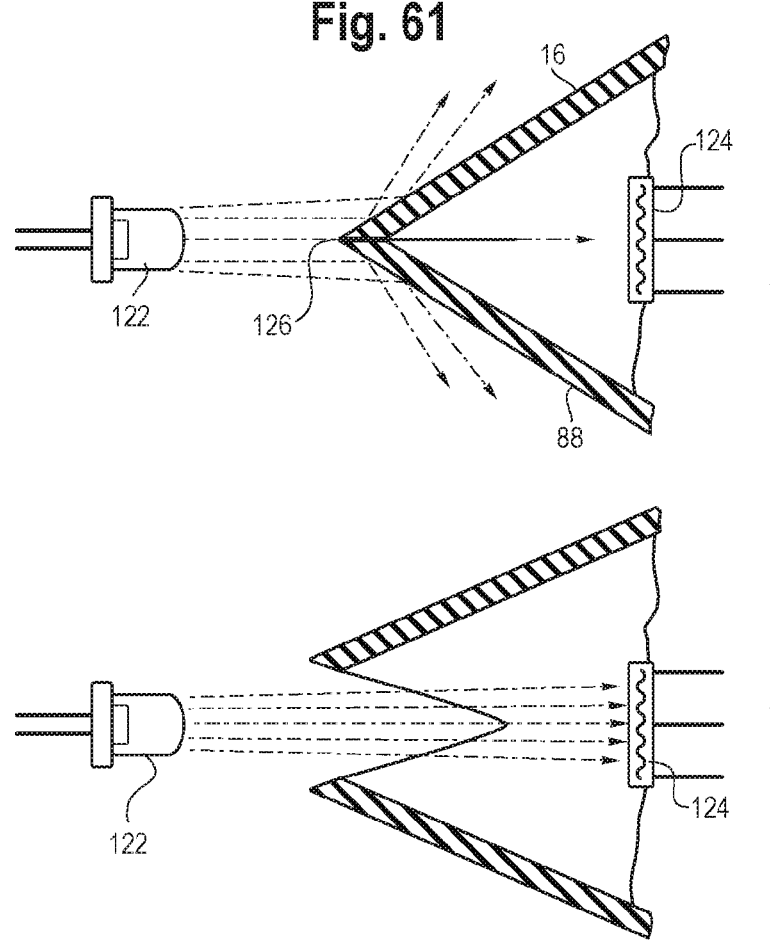
FIG. 61 is a partial, cross-sectional side view of one embodiment of a flow rate sensor assembly.

Referring to FIG. 61, a light source 122 is situated outside of and directed towards the valve 16 of the type in embodiment disclosed in Section 5.1, with the photodetector 124 remaining inside the valve pointed towards the light source. In this embodiment, the more the valve opens the opening 126, the more light reaches the photodetector. Similar methods are applicable to this embodiment as they are in 5.1, including filtering and frequency encoding as well as some of 5.1.s vulnerabilities to drug interference. The photodector 124 communicates with the computer 500 and processor 502.

5.2.2. Body Heat (Infrared)

Figure 62:
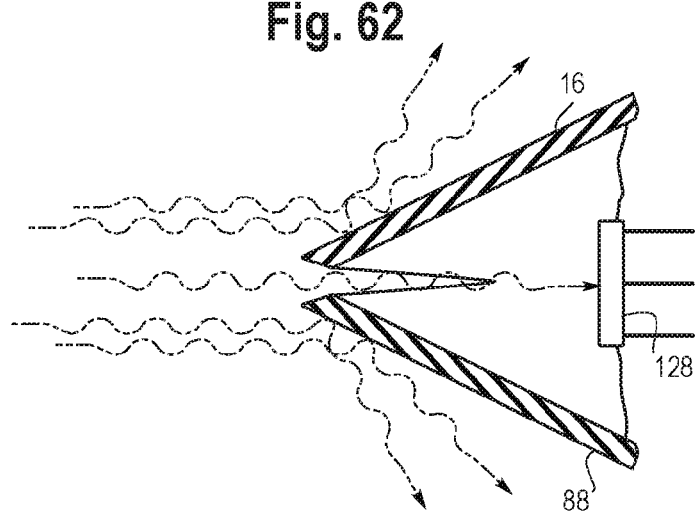
FIG. 62 is a partial, cross-sectional side view of one embodiment of a flow rate sensor assembly.

Similar to the embodiments disclosed in Sections 5.1. and 5.2., and referring to FIG. 62, an infrared photodetector 128 is situated on the inside of a valve 16 of the type described in 5.1 and 5.2. Similar to 5.2, as the valve 16 opens, more light is allowed to reach the photodetector 128. In this embodiment, the photodetector is selected such that it is most sensitive to infrared wavelengths emitted by the human body. As the infrared-opaque valve opens, more infrared light emanating from the user's mouth (mouthpiece device) or face (mask device) enters and is absorbed by the photodetector, or photodiode. The photodector 128 communicates with the computer 500 and processor 502. This signal is analyzed by the microcontroller.

5.3. Oscillating Body

Referring to FIG. 63, a light source 122 and photodetector 124 are facing each other with an opaque body 96 in between.

The opaque body is free to move such that it may block the light from the source from reaching the detector in position 1 and allow the light to reach the detector in position 2.

This opaque body is designed in such a way that it oscillates when flow is present and its oscillations are unique to different flow rates. The amplitudes of these oscillations are such that position 1 and position 2 are reached. The oscillating body may be a reed made of silicone or plastic, a moving vane, a rotating vane or a flapping piece of loose or stiff material, similar to that of a flag. This is not exclusive as any oscillating body may work. The signal coming from the photodetector is then continuously analyzed and the corresponding flow rate is inferred. The photodetector 124 communicates with the computer 500 and processor 502.

6. Spring Displacement

The following embodiments rely on the movement of a spring (linear or non-linear, tension or compression) in response to either inhalation pressure or inhalation flow rate. As the spring moves from one position to another, it brings with it or activates a range of sensing hardware as follows:

6.1. Hall Effect

A magnet is positioned on the moveable end of the spring with a Hall Effect sensor at a fixed position. The Hall Effect sensor detects changes in the magnetic field as the magnet moves from one position to another, and this can be analyzed using various algorithms to determine flow.

6.2. Capacitance

A charged plate is positioned on the moveable end of the spring with an oppositely charged plate at a fixed position, separated by air (the dielectric). The capacitance changes as the charged plate on the spring moves and this can be detected using various hardware and software methods.

6.3. Reed Switches

A magnet is positioned on the moving end of the spring and a collection or magnetic reed switches are positioned along the length of the spring. As the spring deflects and brings the magnet with it, different reed switches are closed and by determining which switches are open vs. closed, the position of the spring and therefore the flow rate can be approximated.

6.4. Inductive Sensor

A conductive plate is positioned on the moveable end of the spring with an inductive coil producing and electromagnetic field in close proximity. As the distance between the coil and the plate changes, the inductance of the system changes which may be analyzed by software. This in turn can be used to approximate the position of the spring and therefore, flow rate.

7. Pinwheel Anemometer 7.1. A pinwheel is placed within the chamber such that its rotational speed changes with changing flow rate. The rotational speed of the pinwheel can be monitored by a rotating contact switch, periodic breaking of a light curtain or magnet and Hall Effect sensor combination and this speed can be used to approximate the flow rate through the chamber.

8. Heated Surface
8.1. Hotwire Anemometer

A wire or mesh is heated by applying a constant voltage across it. As air moves across this wire, it cools and its resistance drops. Since voltage remains constant, the current through the wire increases which can be monitored by electronics. The amount of current flowing through the wire is then used to infer flow rate.

8.2. Thin-film Flow Sensor

This is the same principle as the hotwire anemometer except that it is less intrusive. A thin film, heated sensor is placed on a surface within the chamber and the amount of current that flows through the sensor is used to determine flow rate.

9. Piezo Flex Sensor
9.1. Deflection Based

When airflow comes into contact with a body, the body exerts a force on the air to change its direction around the body. At the same time, the air imparts that same magnitude of force but in the opposite direction. Using this principle, a piezo flex sensor may be used such that as air impacts its surface, it is forced to deflect and the amount of deflection will be proportional to the amount of flow hitting the sensor. Piezo material generate a voltage under strain so strain can be detected and analyzed with various algorithms. Greater strain is a sign of greater flow rates.

9.2. Oscillation Based

Air flowing around a blunt object may generate vortices at a particular frequency as boundary layer separation occurs. This vortex shedding may induce vibrations in the object itself and if this object is made of a piezo-electric material, a voltage may be produced at a frequency matching that of the oscillating body. This signal may be analyzed and flow rates inferred using various algorithms. Alternatively, to amplify the signal, various objects may be used which cause vortex shedding at different frequencies at the same flow rate. When the shedding frequency matches the resonant frequency of the object, large amplitude oscillations will be induced which may be easier to detect and analyze.

10. Multistage Contact Switch 10.1. Different switches may be closed at discrete steps. Multiple printed conducting pathways could be printed onto a flexible surface and different switches will be closed at different positions of the flexible member. Based on which paths are closed vs open, the position of the member can be estimated and therefore the flow rate as well.

11. Potentiometer Vane 11.1. Using the forces generated by flow as described in embodiment 9.1., a vane may be designed such that it adjusts a potentiometer when flow is present. A biasing spring will make the position of the vane dependent on the flow present. The resistance of the potentiometer may be monitored continuously and the flow inferred based on this measurement.

MDI Actuation Detection

Detection of MDI actuation is an important piece of information that can be used for dose assurance and for providing feedback to the user about optimizing their breathing technique. Several characteristics of the MDI can be used and detected by an actuation detector, as described in various embodiments below, to detect the MDI actuation including the visual appearance of the aerosol plume, its sound, the temperature drop associated with rapid HEA propellant evaporation, its force to fire, the dielectric constant of the aerosol, displacement to fire, its pressure at actuation or communications with smart features on the MDI itself.

1. Light-Based Methods
1.1. Light Transmission (AKA Light Curtain)

Figure 8:
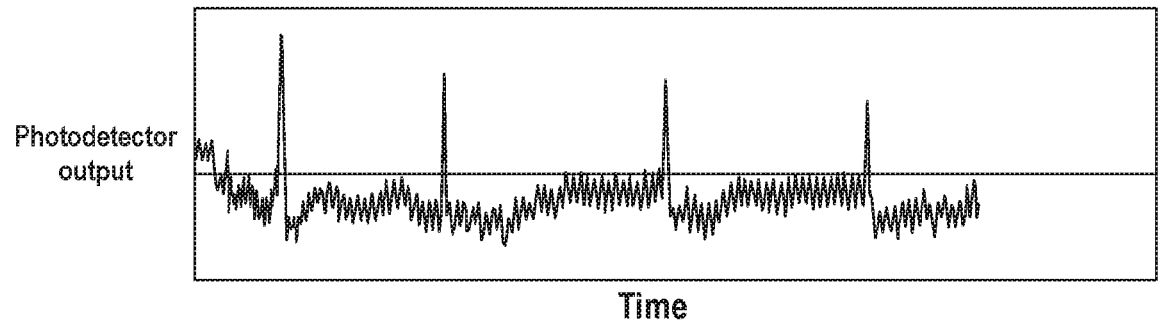
FIG. 8 is a photodetector output v. time graph for an MDI actuation.

Referring to FIGS. 7 and 8, in one embodiment, a light source (e.g., blue LED) 39 and a light detector (photodetector) 32 are spaced apart and oriented such that the source is directed towards the detector with an air gap in between, or such that light from the source may be detected by the actuation detector. Any wavelength in the visible spectrum and/or infrared spectrum may be used to detect MDI actuation. This air gap is large enough so that when an MDI is actuated, the aerosol plume is minimally impeded by the presence of the source and detector. As the aerosol plume travels between the source and detector, the amount of light originating from the source that reaches the detector will be reduced as the aerosol scatters and reflects light away. The result is an abrupt change in the output from the detector whose signal can be analyzed by various software algorithms. In particular, the aerosol drug particles scatter, reflect and/or absorb blue light to varying degrees within the interior space of the chamber. The change in light is detected by the photodetector, which communicates a signal to the processor. When no aerosol is present in the interior space, the photodetector records a baseline reading of receive light. When there is actuation, because of light scattering/reflection/absorption, the photodetector receives less or more light. Based on these parameters, the smart VHC may accurately determine the MDI actuation. This event may further be used to record a timestamp, which information may be useful for adherence tracking and monitoring. As shown in FIG. 8, the photodetector output over time shows a reliable indicator of actuations as evidenced by the periodic spikes on the timeline.

The wavelength of the light source can be any wavelength and ideally from the infrared bandwidth so that the light is not visible and distracting to the user. The sensitivity of the light detector should be such that it is most sensitive to light emanating from the light source. Ideal light sources have wavelengths in the infrared (wavelengths of 700 nm to 1 mm) or visible light (wavelengths 400 nm to 700 nm) spectra and are in the form of efficient Light Emitting Diodes (LEDs).

Ideal light detectors have highest sensitivity to the wavelength of the source light and can include photodiodes, phototransistors or light-sensitive-resistors (LSR).

1.2. Light Reflection

A light source and a light detector are oriented such that the detector will only receive light from the source when a reflecting body or media is present. When the aerosol plume is present, light from the source is reflected and at least a portion of this reflected light is absorbed by the detector. This spike in light absorption at the detector results in a change in voltage that can be analyzed by various software algorithms. Light source and detector should have the same properties as described in the Light Transmission embodiment.

1.3. Color Reflection

A white light source and a color sensor are oriented such that the color sensor will only receive light after the white light is reflected off of a body or media. When the aerosol plume is present, it reflects some wavelengths of light while absorbing others. The combination of all of the reflected wavelengths will dictate the aerosol plume's color which can be detected by the color sensor. The sensor can detect abrupt changes in light levels as well as abrupt changes in color which may be analyzed with various software algorithms to detect MDI actuation.

1.4. Camera and Image Processing

Cameras and image processing tools are used in a wide range of applications, identification of an aerosol plume can be one application. Various software algorithms may be used.

2. Sound-Based Methods

Referring to FIGS. 24-28, a VHC, or backpiece 8 coupled thereto, is configured with a microphone 82 (actuation detector), audio interface, visual feedback indicator 40, microcontroller (which may be a processor 502), memory storage 504, limit switch, Bluetooth/Wi-Fi connectivity and battery 503, all of which may be housed in the backpiece 8. The limit switch 62 detects the presence of an MDI, which triggers the electronic system to power up. The microphone and audio interface being recording sounds inside the interior cavity. When the MDI is actuated, the full soundwave of the actuation is captured by the microphone 82, and stored into memory for analysis.

For all sound embodiments, a second microphone may be used to pick up ambient noise. The signal from this microphone may then be used for noise reduction purposes in the signal being analyzed.

2.1. Microphone—Simple Volume Threshold

A microphone is situated near the mouthpiece of the MDI and is at least partially insulated from sound from the outside environment. During MDI actuation, a relatively loud sound is produced as the drug is force out of the MDI orifice and this spike in volume can be detected using various software algorithms.

2.2. Microphone—Volume Threshold with Pre-filtering

A simple volume threshold method is subject to false triggers as a result of any loud sound from the environment that is not adequately dampened by the sound insulation. To further reduce the risk of a false trigger, a volume threshold can be combined with pre-filtering the incoming microphone signal.

The sound produced during a MDI actuation is comprised of various sound frequencies. Using low pass, high pass or band pass filters, the microphone signal can be tuned such that only frequencies associated with a MDI actuation are listened too. This limits the possibility of false triggers to loud sounds that are within the sound bandwidth of the MDI actuation.

A microphone is situated near the mouthpiece of the MDI and is at least partially insulated from sounds from the outside environment. The output signal of the microphone passes through a series of carefully selected resistors, capacitors and/or inductors arranged in such a way as to construct low and/or high pass filters. After passing through these filters, the signal is analyzed by the microcontroller (FIG. 28) or other processor 502 for spikes in volume which can be detected using various algorithms. Frequency filtering may also be accomplished digitally.

2.3. Microphone—Target Signal Comparison (Filtered and Non-Filtered)

Both methods (2.1. and 2.2.) are subject to false triggers as a result of loud ambient sounds. Instead of, or in conjunction with, simple volume thresholds, quantitative comparison between the incoming sounds with a pre-defined target can nearly eliminate the risk of false triggers. Autocorrelation and minimizing root-mean squares are a few algorithms based in the time domain that can be used for signal comparison and both of these may be combined with analog or digital filters as described in 2.2, or with no filtering at all. Frequency domain algorithms can also be used for comparing a source to a target.

3. Temperature Change Methods

3.1. Temperature Sensor and Direct Contact Evaporation

MDI's typically contain a propellant, for example Hydrofluoroalkane (HFA), which has a low boiling point. During MDI actuation, some of this propellant is able to escape the MDI in its liquid phase. When this liquid propellant is exposed to the outside environment, it rapidly evaporates as a result of its low boiling point and minimal vapor pressure of the propellant in the surrounding atmosphere. Through evaporative cooling, a rapid drop in temperature arises in all material in which the liquid propellant is in contact with.

Figure 38:
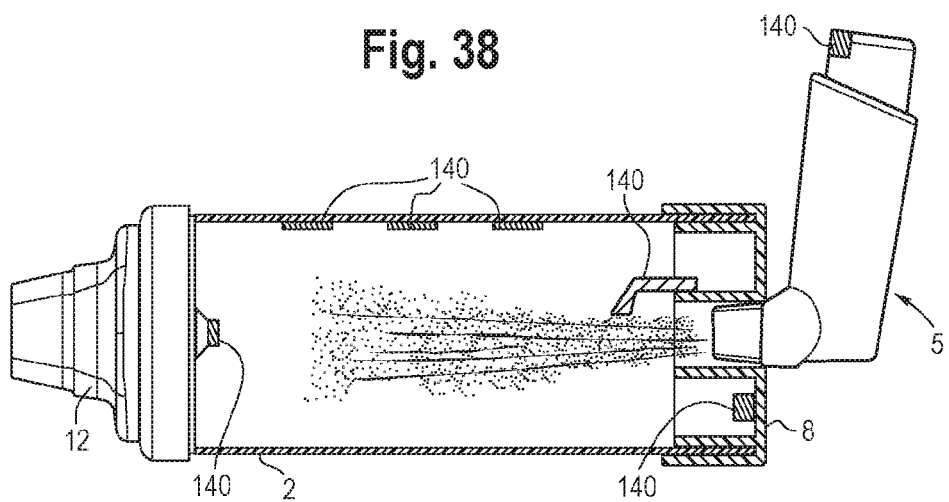
FIG. 38 is a side view of an alternative embodiment of a smart VHC.
Figure 39:
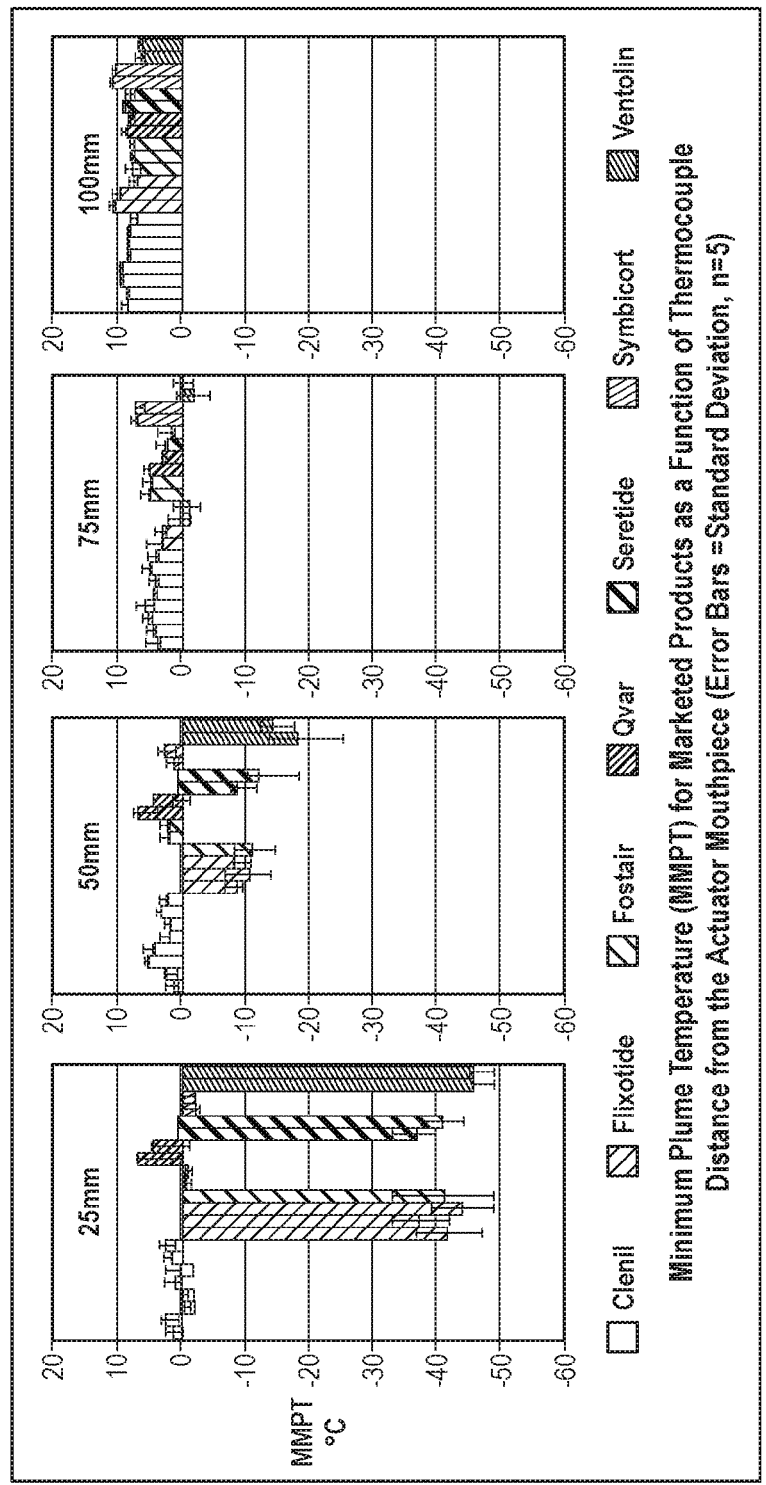
FIG. 39 are minimum plume temperature as a function of distance from thermocouple for various MDI products.

Referring to FIGS. 38 and 39, one embodiment of a VHC and/or MDI is configured with one or more temperature sensors 140 (actuation detector), for example coupled to, or embedded in, the wall of the holding chamber, or disposed in the interior space thereof, for example on the inhalation valve or baffle at the output end of the chamber housing. The temperature sensors may be a temperature sensitive resistor, thermocouple, thermistor or infrared temperature sensor to detect rapid drops in temperature and subsequent warming. Alternatively, a rapid drop in temperature alone could be sufficient. This rapid temperature drop and/or rewarming can be detected using various software algorithms. In this embodiment, the temperature sensor is placed in the path of the aerosol plume such that a certain amount of the liquid propellant is deposited onto its surface. Care is taken to avoid any substantial drug loss from the sensor being in the aerosol path. A sensor with minimal thermal mass is ideal to promote rapid detection of temperature changes. As shown in FIG. 39, various minimum plume temperatures may be associated with various MDI formulations. The temperature data may then be input to the microcontroller or other processor 502 (not shown) to indicate and record MDI actuation.

3.2. Temperature Sensor and Air Temperature

The embodiment of 3.1. requires the temperature sensor to be in the aerosol path during MDI actuation. Alternatively, rapid drops in air temperature may be monitored since the evaporation of the propellant would cause a decrease in the surrounding air temperature as well. For example, as shown in FIG. 38, the sensor 140 may be located outside the interior space of the holding chamber, for example on the MDI. This would allow for a non-invasive method of MDI actuation using temperature. The position of the temperature sensor should be proximal to the MDI since the magnitude of the temperature drop decreases as distance from the MDI increases. This is a result of most of the propellant evaporating prior to travelling large distances. A ratio of temperatures at different distances from the MDI or a profile of temperatures vs. distance may also be evaluated using multiple temperature sensors positioned along the chamber for more confidence in detecting MDI actuation.

3.3. Temperature Sensor on the MDI

As shown in FIG. 38, immediately following actuation, the propellant is not in phase equilibrium. This causes some of the liquid propellant to evaporate until saturation occurs and equilibrium is restored. The evaporation causes the temperature of the canister to drop which can be detected using a contact temperature sensor or any other sensor mentioned in embodiment 3.1. This could be integrated into the MDI adapter or an over-the-counter add on to the MDI canister with wireless communications capability to communicate with the MDI adapter. The temperature data may then be input to the microcontroller or other processor 502 (not shown) to indicate and record MDI actuation.

4. Force to Fire
4.1. Local Force Peak Detection

Figure 40:
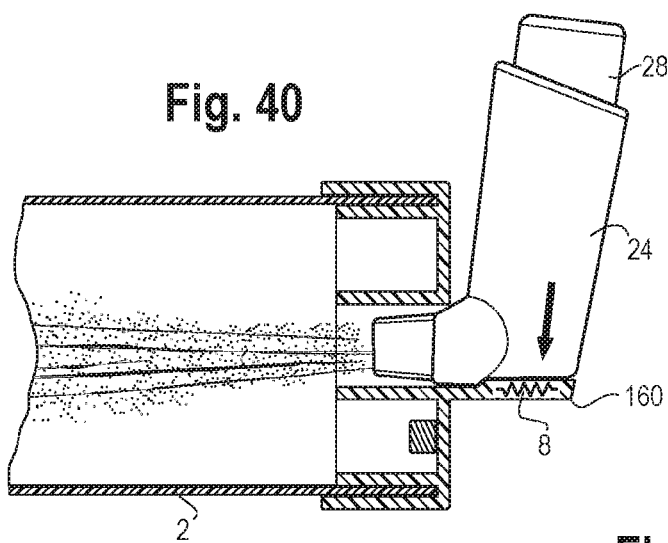
FIG. 40 is a partial, cross-sectional side view of an MDI applied to one embodiment of a VHC.
Figure 41:
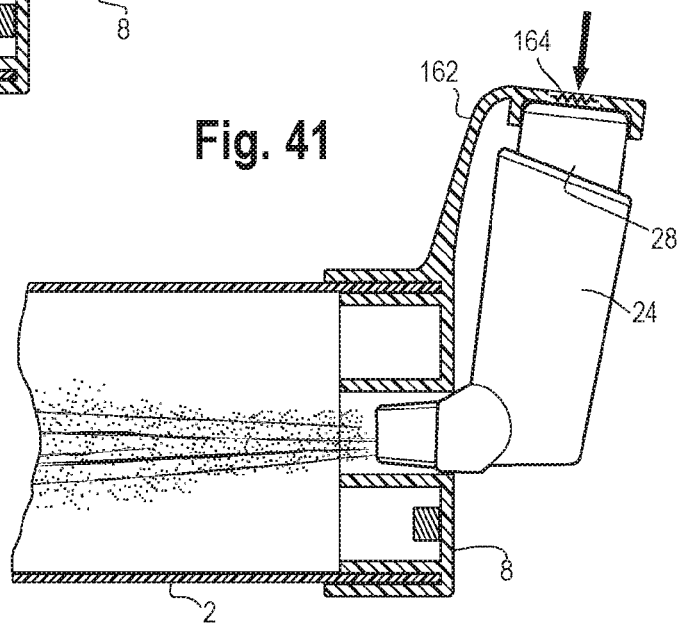
FIG. 41 is a partial, cross-sectional side view of an MDI applied to another embodiment of a VHC.
Figure 42:
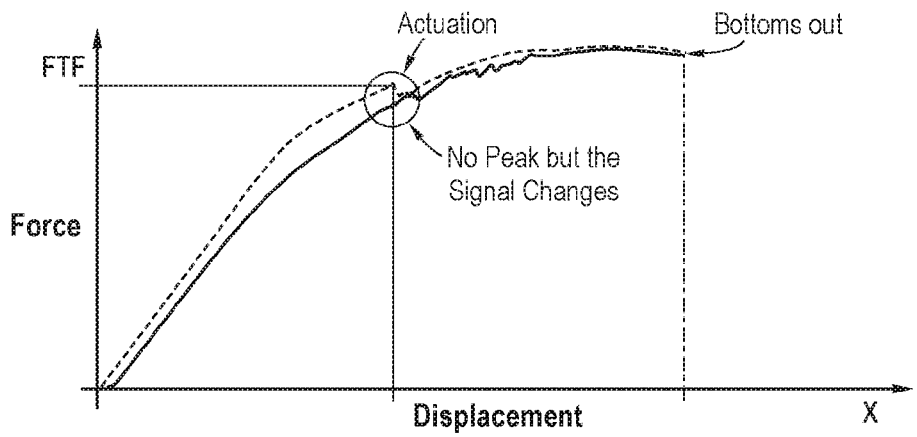
FIG. 42 is a force v. displacement for an exemplary MDI actuation.

Referring to FIGS. 40-42, a force sensitive resistor (FSR), or actuation detector, situated at the top or base of the MDI boot may be used to determine a force measurement and to detect the actuation of the MDI. When looking at a force vs. displacement curve for a canister in a boot as shown in FIG. 42, there can be a peak or other signal change at the point of actuation that may be detected using the FSR and various algorithms. Several types of force sensors can be used in addition to FSR including strain gauges, spring-displacement, piezo-flex sensors and others. As shown in FIG. 40, a force sensor 160 is located on a support flange of the backpiece 8. In FIG. 41, the force sensor 160 is located on a cap 164 coupled to the backpiece with a tether 162 and secured to the top of the container 28, where it is engaged by the user during actuation of the MDI. The force sensor 160 communicates a signal to the computer 500 and processor 502.

4.2. Force Threshold

A simple force threshold may also be used instead of a peak finder although there would be less certainty with this method.

Figure 43:
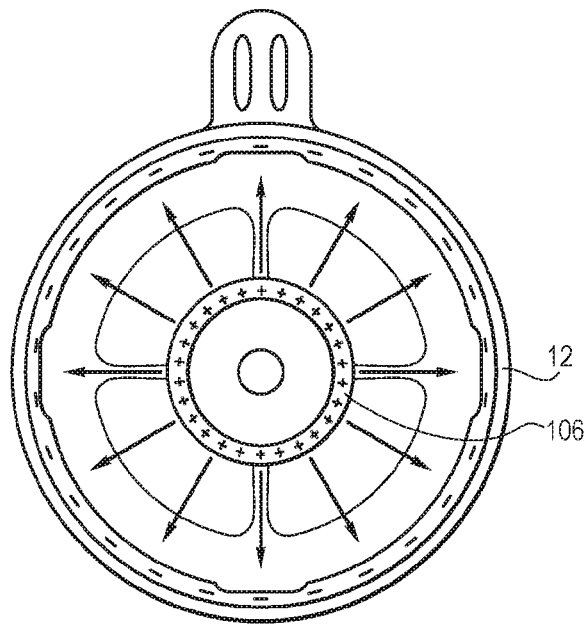
FIG. 43 is an end view of one embodiment of a backpiece of a VHC.
Figure 44:
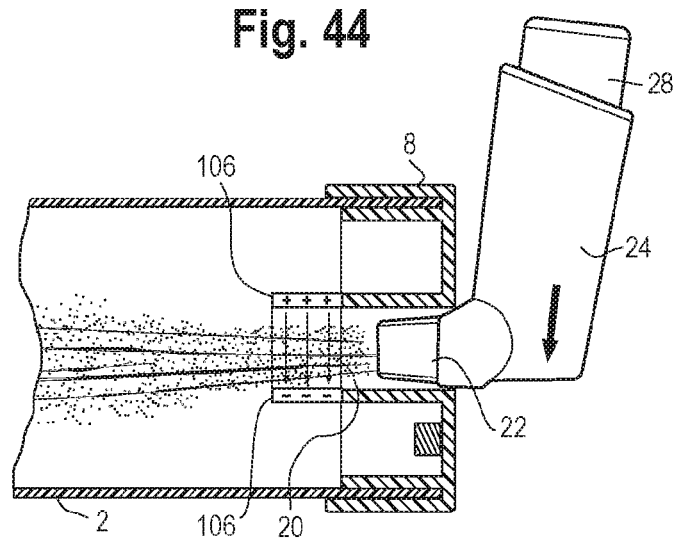
FIG. 44 is a side view of the backpiece shown in FIG. 43.

5. Capacitance Change 5.1. One factor that affects the capacitance of a capacitor 106 is the dielectric constant of the material between the two charged surfaces. Assuming the dielectric constant of medical aerosols is different from that of air, a change in capacitance of an integrated capacitor may be used to detect MDI actuation. Referring to FIGS. 43 and 44, the capacitor would have an open air gap that is easily infiltrated by the aerosol from the MDI. The capacitor may be located at the output end, as shown in FIG. 43, or the input end, as shown in FIG. 44. The capacitance would then be monitored for changes using an oscillating or charge/discharge circuit whose abrupt change in frequency would signal the MDI actuation. This could be detected using various software algorithms. The capacitor communicates with the computer 500 and processor 502.

6. Displacement to Fire
6.1. Magnetic Cap and Reed Switch

Figure 45A:
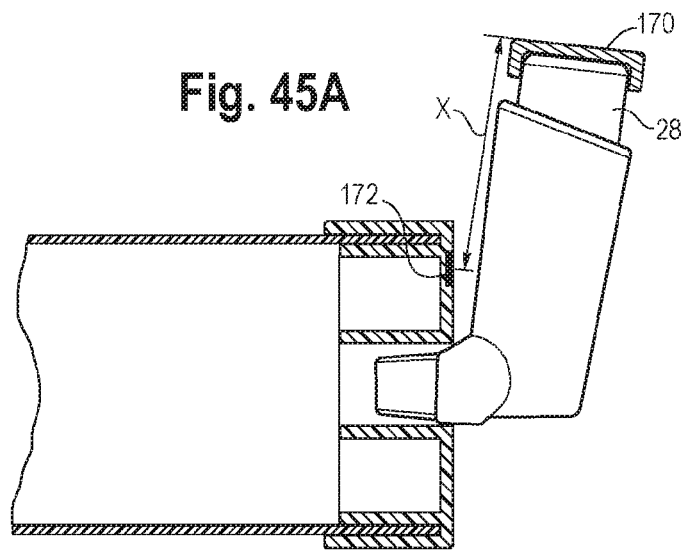
FIGS. 45A and B are partial, cross-sectional side views of an MDI in an actuated and non-actuated positions relative to a smart VHC.
Figure 45B:
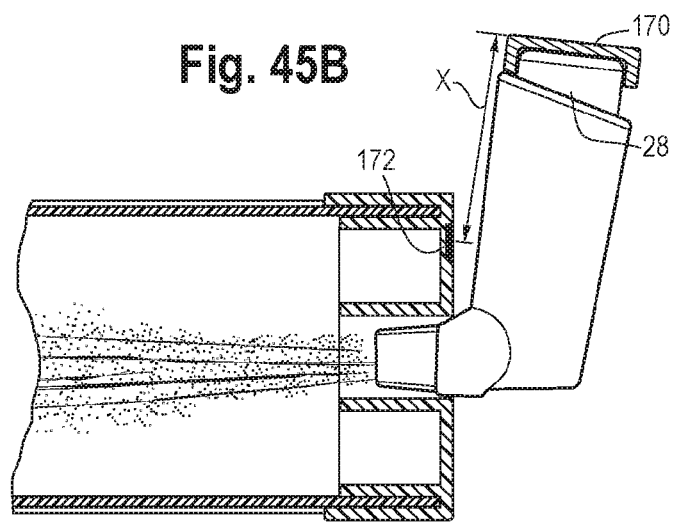

Referring to FIGS. 45A and B, a canister cap 170 is fitted securely over the MDI canister, in a similar position to a dose counter, and travels with the canister during actuation. The cap has magnetic properties by means of embedding a permanent magnet within its structure, having magnetic ink printed on it or being produced from a magnetic material. Within the MDI adapter is a Hall affect sensor or reed switch 172. When the MDI canister is depressed to its actuation position, the reed switch closes and this is detected by software. Using a Hall Effect sensor, the signal can be analyzed for a plateau which would signify the bottoming out of the MDI canister, or change in X, and the point of actuation. The sensor communicates with the computer 500 and processor 502.

6.2. Conducting Cap and Inductor

Similar to embodiment 6.1., a cap is sold with the VHC. In this embodiment, the cap has conductive properties and is not necessarily magnetic. An oscillating electromagnetic field is produced by an inductor within the chamber which induces a current in the MDI canister cap. As the cap moves closer to the inductor during actuation, the inductance of the system changes which can be detected and analyzed. Once a plateau in the signal is reached signifying the canister bottoming out, an actuation can be registered by the software.

7. Pressure Detection

When the MDI is actuated, its pressurized contents are forced out of the nozzle and into the VHC. The pressure wave that accompanies this may be detected with a pressure transducer 78 placed within the chamber or near the mouthpiece of the MDI itself as shown in FIG. 18. In particular, one or more pressure sensors 78 are disposed on or along an interior surface of the wall in the interior space of the chamber. Referring to FIG. 20, pressure sensor output v. time illustrates when actuation occurs as evidenced by the spike.

Referring to FIGS. 46 and 47, a pressure sensor 78 may be disposed at the input or output ends of the holding chamber in the interior space. The sensor detects and records the pressure differential.

Figure 48:
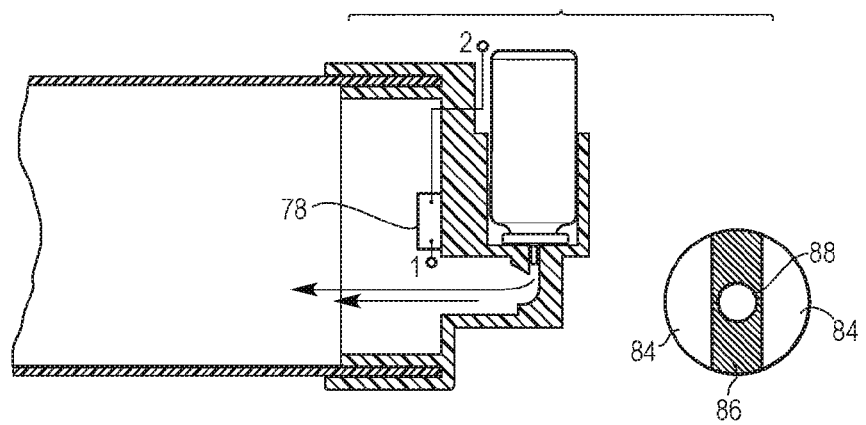
FIG. 48 is a partial, cross-sectional view of one embodiment of a smart MDI.

Referring to FIG. 48, one or more flow channels 84 are positioned adjacent the support block 86, with its discharge orifice 88. Ambient air is entrained through the flow channels, which provide a flow path of known resistance. A pressure sensor 78 records the pressure difference.

Figures 49, 50:
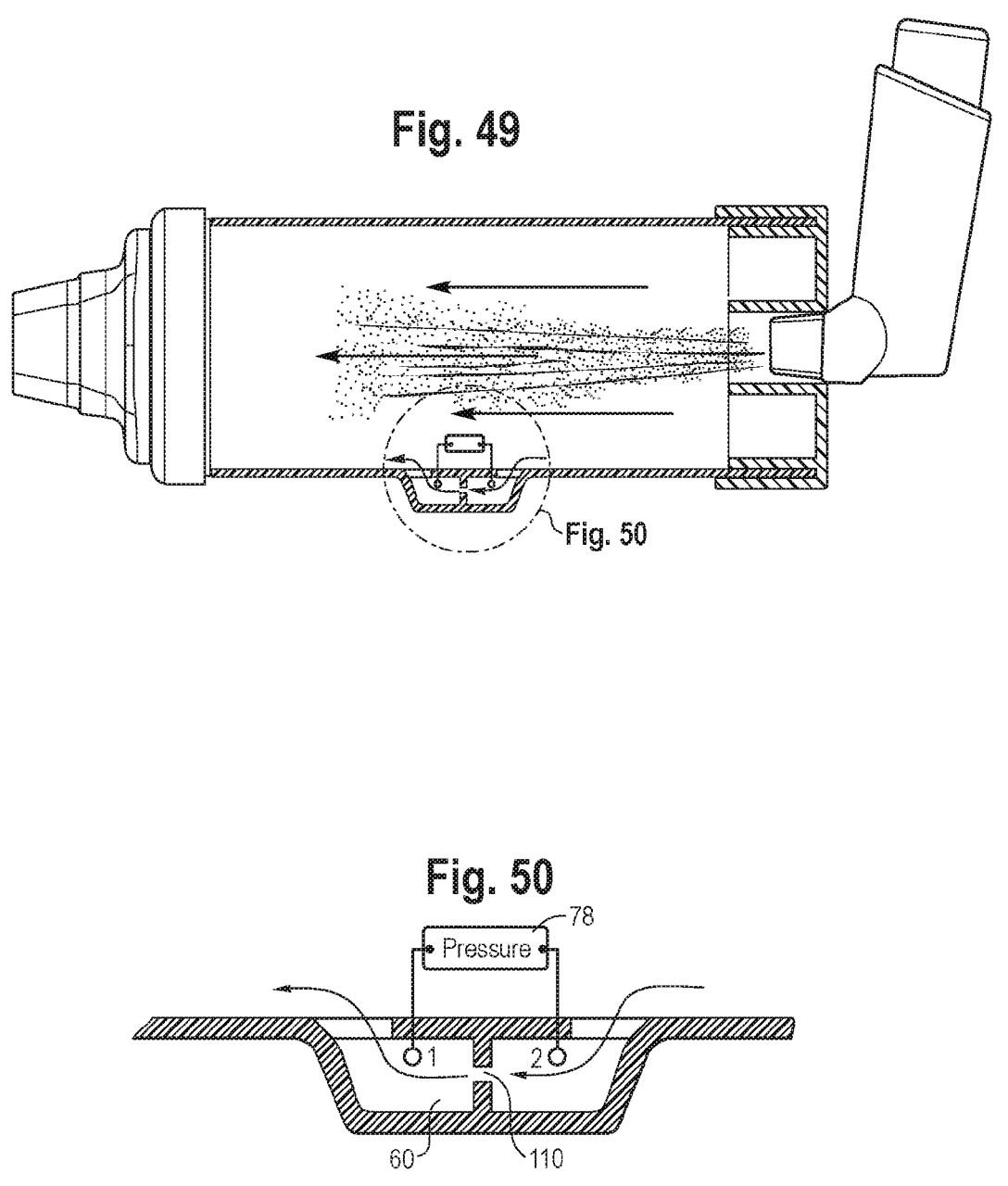

Referring to FIGS. 49 and 50, a restrictive orifice is created in a bypass channel. The pressure drop across the restrictive orifice may be detected and recorded by a pressure sensor, and then correlated with the flow rate. The various pressure sensors communicate with the computer 500 and processor 502.

Figure 78:
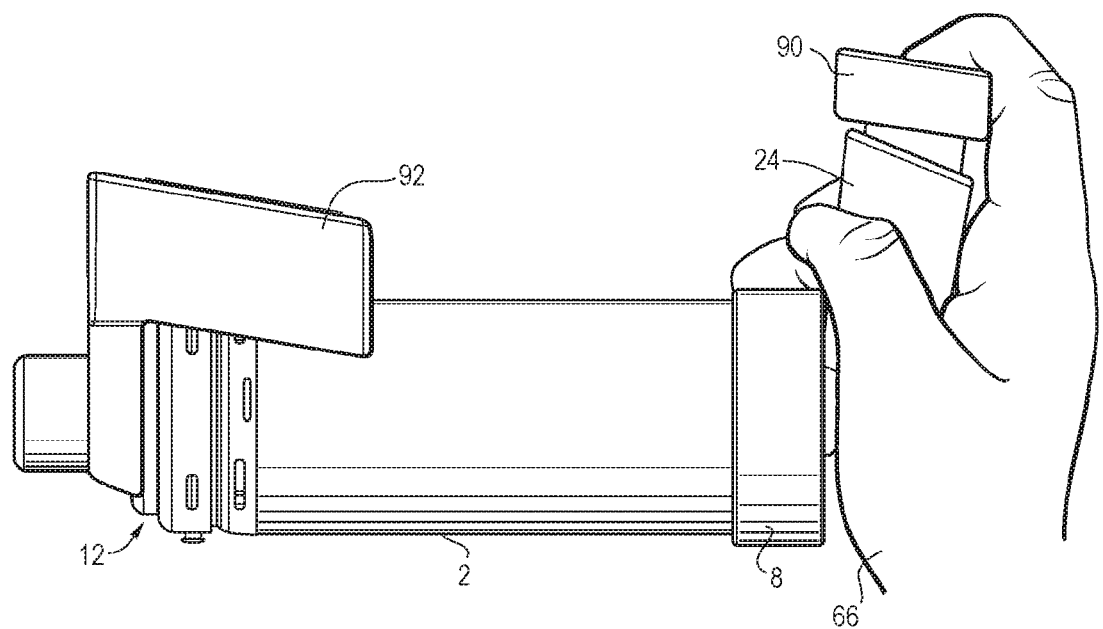
FIG. 78 is a side view of one embodiment of a smart VHC.

8. Communication with Smart MDI 8.1 Referring to FIG. 78, an MDI may be configured with a dose counter module 90, which has been actuated for the purpose of adherence monitoring and captures dose actuation time, count and total. At the same time, the VHC may be configured with a flow detection module 92, which captures inhalation time, duration and count, with the modules being in communication, for example with Bluetooth technology. Communications with these devices from the smart VHC or its application can be used to detect and confirm MDI actuation and technique.

Figure 13:
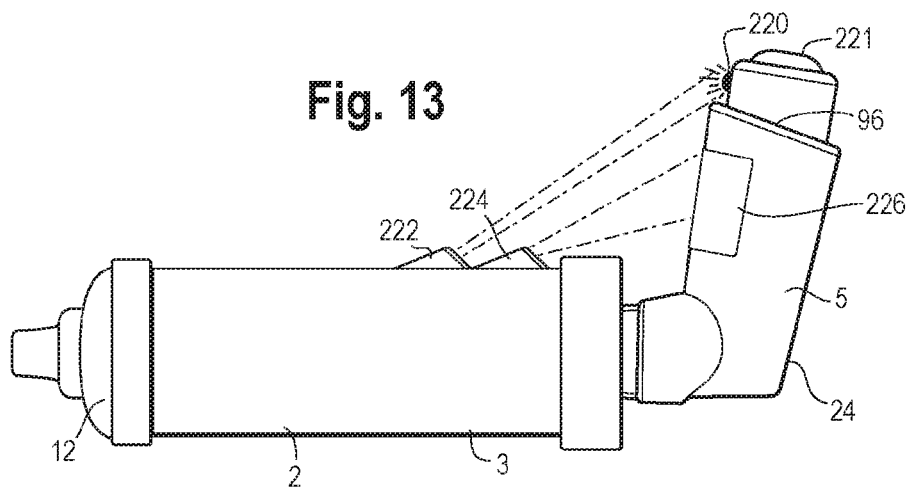
FIG. 13 is a side view of another embodiment of a smart VHC.
Figure 14:
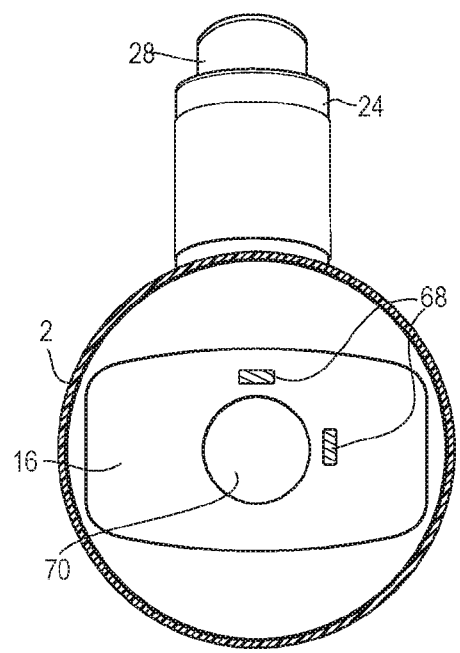
FIG. 14 is an end view of anther embodiment of a smart VHC.

Referring to FIG. 13, the actuation of the MDI is detected by receiving a single from a transmitter 221 placed on top of the MDI canister. Upon actuation, the transmitter outputs a signal that is received by the smart VHC. For example, a piezoelectric disk mounted to the top of the canister, either incorporated into a dose counter coupled to a container or as a separate element, generates enough voltage when pressed to power the transmitter. Several types of transmitter/receivers are possible including IR LED/photodiode, radiofrequency (RF) Tx/Rx or tone generator/microphone. Depending on the type of Tx/Rx, this system may also be used to identify the MDI type, with different RF frequencies being used for controller/rescue inhalers.

MDI Insertion

Providing feedback and confirmation to the user that the MDI has been properly inserted may be a desirable feature of the smart VHC. Additionally, depending on the method used, this feature may govern when the microcontroller or other processor 502 is in a sleep state, further extending the battery life of the device. As an example, when the MDI is inserted, the microcontroller wakes up and draws more current from the power source to power its sensors, displays and communications. Once removed, the microcontroller goes back into a low energy state.

1. Switch
1.1. Limit/Contact Switch

In this embodiment, as shown in FIGS. 19, a limit switch 62 (mechanical), or contact switch, is placed within the backpiece 8 in such a way that upon insertion of the MDI, the switch is closed. The limit switch completes the circuit when the MDI is inserted. The closing of this switch triggers an interrupt in the microcontroller or other processor 502 and permits it to operate in its fully operational state at which point the user is notified through visual or audio cues that the MDI has been fully inserted. When the MDI is removed, the switch opens, prompting the microcontroller to return to its state of low energy requirement. In one embodiment, if the device is inactive for a predetermined time period, e.g., approximately 30 to 120 seconds, the microcontroller may enter into a sleep mode. The predetermined time period may be set/programmed by the user.

Figure 11:
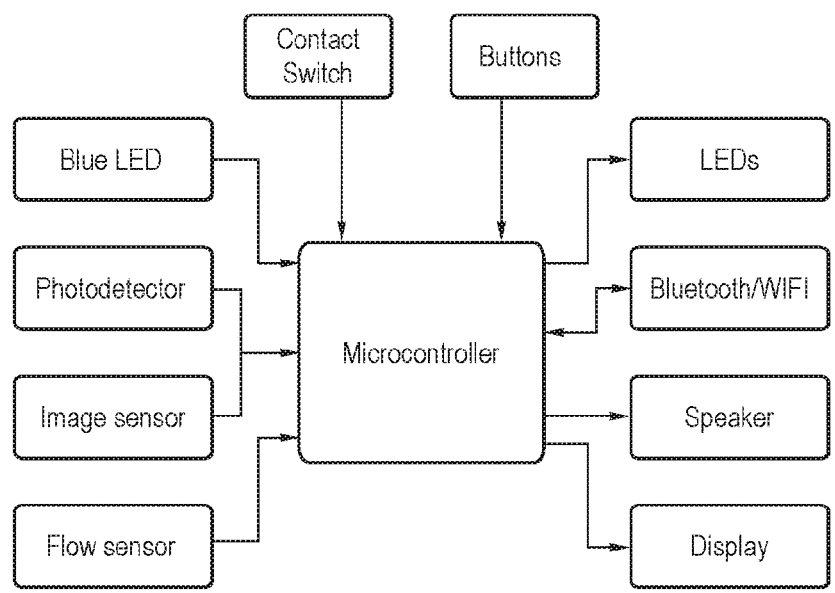
FIG. 11 is a schematic for various input/outputs related to MDI use.

In addition to a contact switch, and referring to FIG. 11, a button may be used to power on/off the system. An audio or visual feedback mechanism, e.g., visual or auditory indicator such as lights and/or an alarm, may be implemented using various LEDs, speakers, and haptic and/or visual displays/indicators.

1.2. Reed Switch

Figure 74:
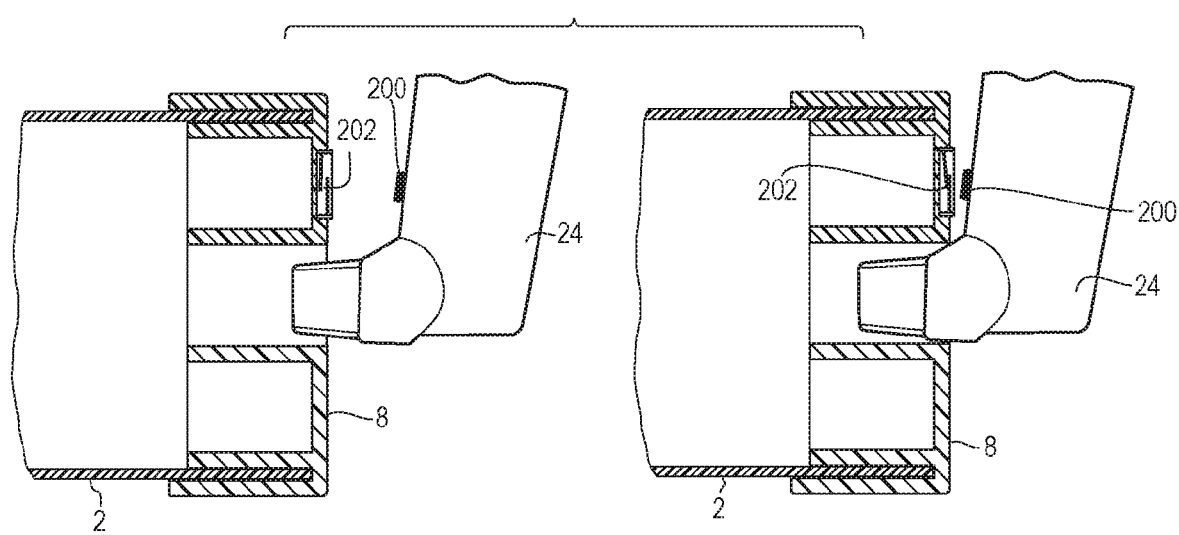
FIG. 74 is an end view of another embodiment of a VHC.

Similar to embodiment 1.1, and referring to FIG. 74, a portion 200 of the MDI is magnetized either with magnetic ink, electromagnets or permanent magnets. When the MDI is inserted, a reed switch 202 is closed. The closing and opening of this switch have identical consequences for microcontroller operation and user feedback as described in 1.1.

1.3. Conductive Path

Figure 75:
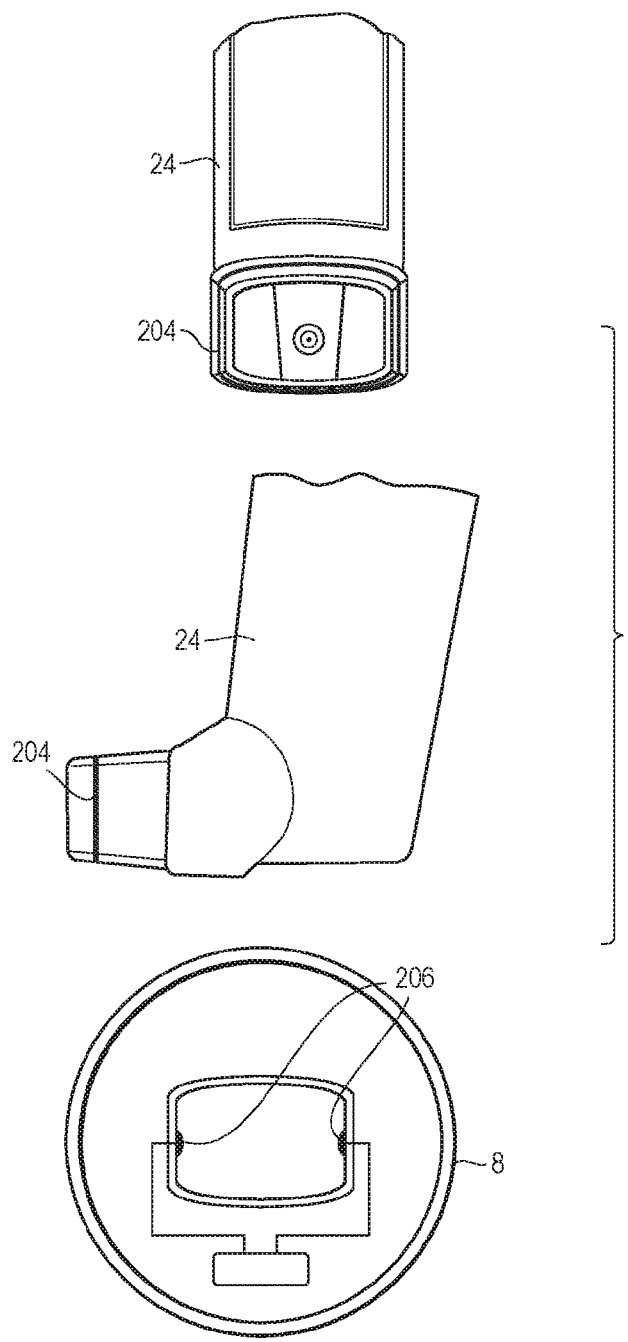
FIG. 75 shows an MDI configured with a conductive material for closing a circuit path in a VHC.
Figure 76:
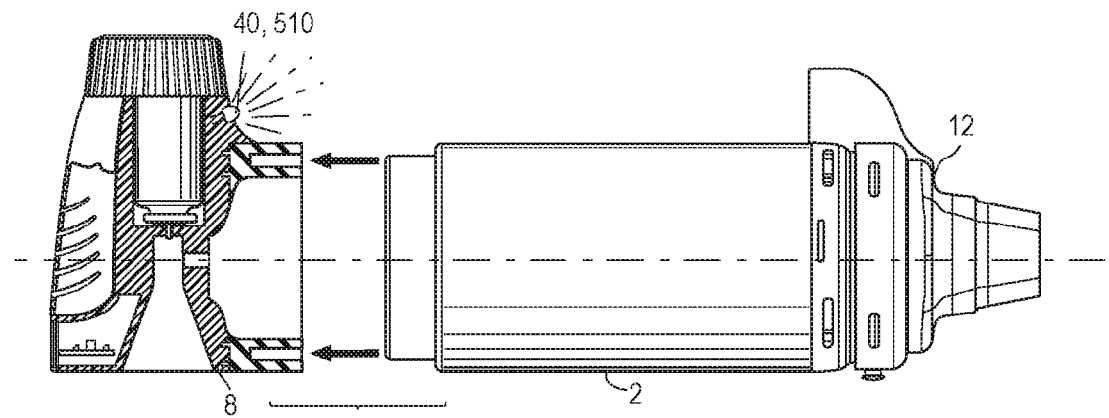
FIG. 76 is a side view of an MDI and VHC.
Figure 77:
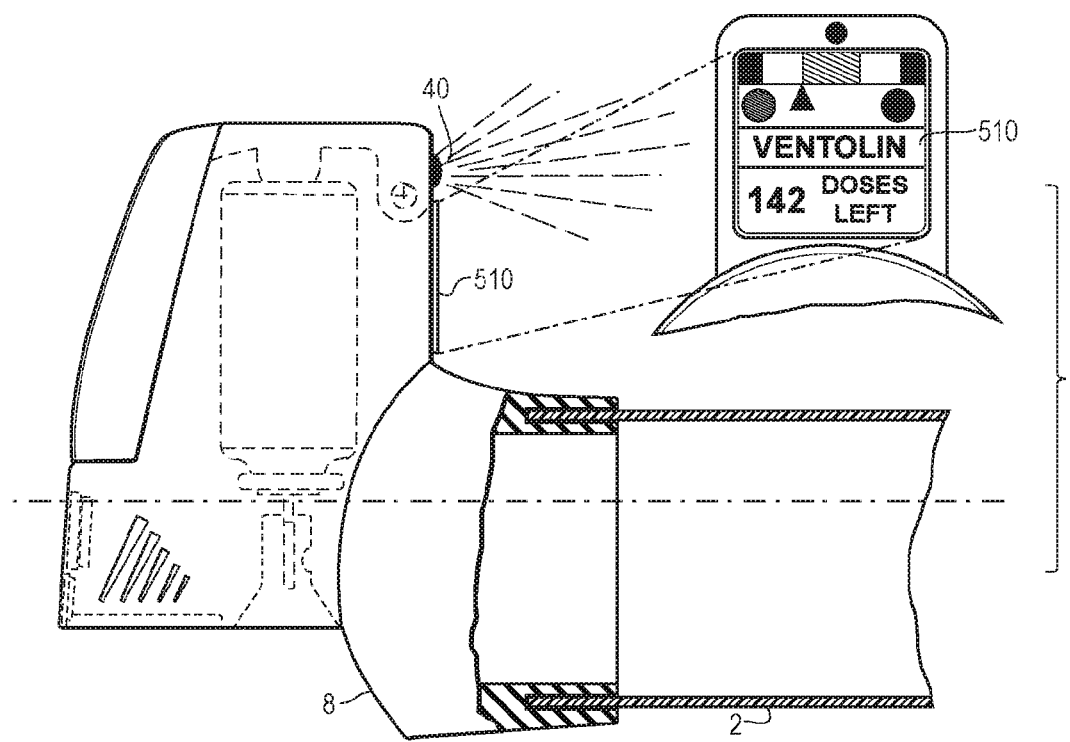
FIG. 77 is a view of a display for an MDI or VHC.

In this embodiment, as shown in FIG. 75, a portion of the MDI, for example the mouthpiece, has an electrically conductive path 204 which, when inserted into the MDI adapter, completes a circuit 206 within the MDI adapter electronics. This circuit is used to provide feedback to the user and enable full functionality of the microcontroller as described in 1.1.

2. Light Curtain 2.1. A light curtain, as disclosed previously, may be used to determine insertion of the MDI into the MDI adapter. In this embodiment, an LED and photodiode are placed opposite each other across the MDI adapter opening. When no MDI is inserted, light from the LED is able to reach the photodiode. Once the MDI is inserted, this light transmission is interrupted which may be detected by the microcontroller and used to provide audio or visual feedback to the user assuring proper insertion of the MDI.

3. Detection of Mouthpiece Shape 3.1. Strain Gauge

Figure 70:
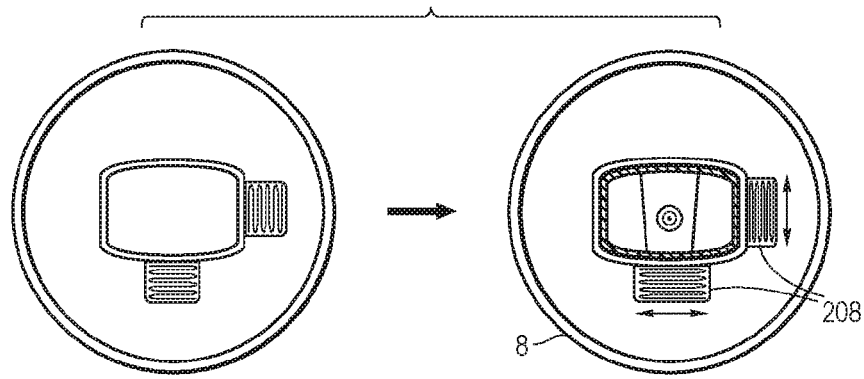
FIG. 70 is an end view of one embodiment of a VHC.

Strain is introduced in the MDI adapter or backpiece as shown in FIG. 70 as the material deforms in order to accommodate the MDI mouthpiece shape. The amount of strain can be measured using strain gauges 206. Monitoring the strain of the MDI adapter can provide a way to detect whether an MDI has been inserted into the MDI adapter. Once strain reaches a certain threshold value, the system can provide feedback to the user to confirm MDI insertion.

3.2. Force Sensitive Resistors (FSR)

Figure 72:
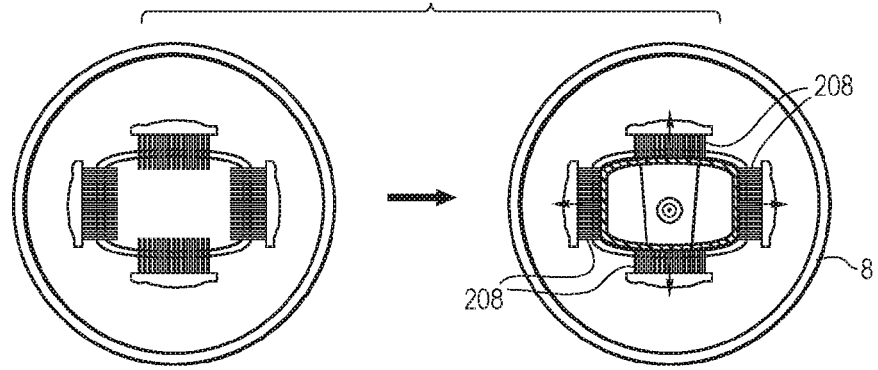
FIG. 72 is an end view of another embodiment of a VHC.

Force sensitive resistors 208 may be placed on or within the MDI adapter or backpiece 8 as shown in FIG. 72. Upon MDI insertion, the MDI mouthpiece exerts a force against the FSR which produces a voltage change that is evaluated by the microcontroller. Depending on the signal coming from the FSR, insertion of the MDI can be concluded and this information relayed back to the user.

3.3. Linear Action Potentiometers

Figure 69:
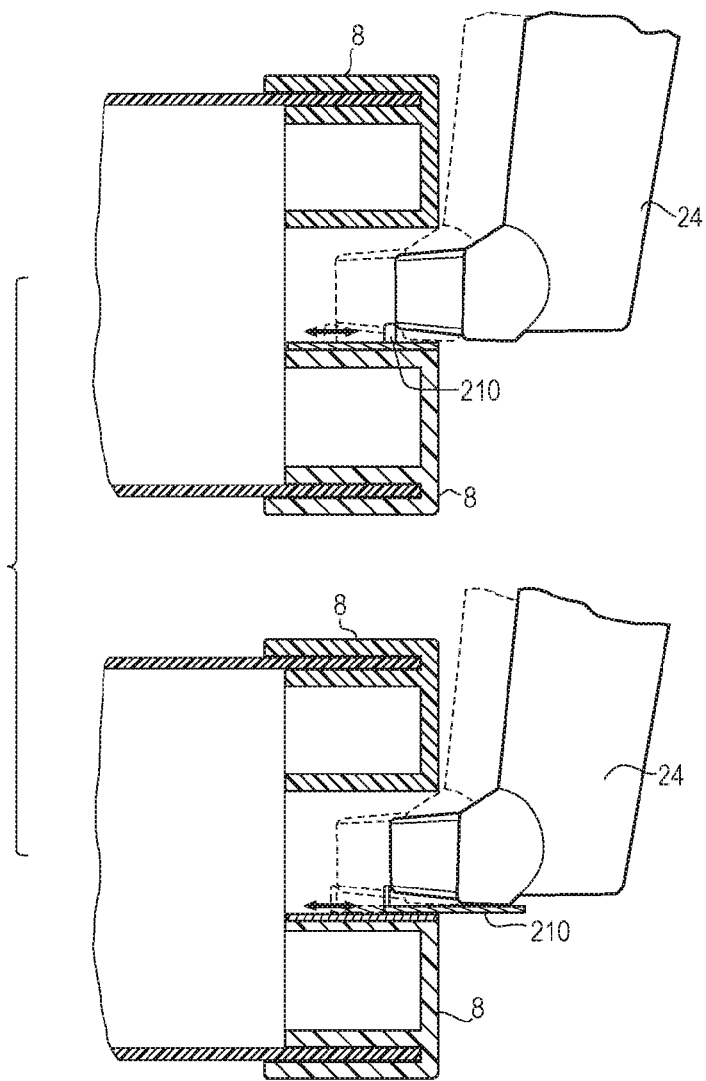
FIG. 69 is a partial, cross-sectional side view of and VHC in a partially and fully inserted position.
Figure 71:
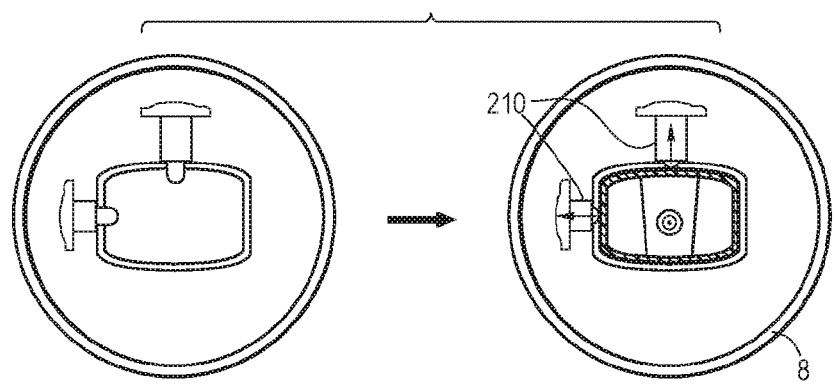
FIG. 71 is an end view of another embodiment of a VHC.

Linear action potentiometers 210 may be positioned on or within the MDI adapter or backpiece as shown in FIGS. 69 and 71. Upon MDI insertion, the potentiometer is displaced which produces a voltage change that is evaluated by the microcontroller. Depending on the signal coming from the potentiometer, insertion of the MDI can be concluded and this information relayed back to the user.

3. Image Processing 4.1. A camera or series of cameras may be used to determine how far a MDI has been inserted into the MDI adapter. Various image processing algorithms may be used to determine this and once confirmed, this information may be relayed back to the user.

Power Supply and Distribution

Problem Identification

All embodiments require the use of electrical power for functionality. Various power supplies may be used on their own or in combination with other sources. Sensors and feedback methods may receive power even if they are on separate chamber components.

Power Supplies

1. Batteries (Single or Multiple Batteries May be Used for Each)

1.1. Permanent, disposable

The power supply may be such that once the battery has been depleted, the entire electronic device is disposed of. The battery would be permanently enclosed within the electronics body such that access is restricted without damaging the device.

1.2. Replaceable

The power supply may be such that once the battery has been depleted, the user is able to access the battery cartridge and replace the depleted cells with full ones. This is similar to many children's toys or watch batteries.

1.3. Rechargeable

The battery may be rechargeable such that once the battery has been depleted, the user can simply recharge it through a DC power jack, USB or other method. Additionally, the battery may be trickle charged throughout its life which can extend its depletion time. Trickle charging refers to charging a battery continuously or periodically with a very small current. Alone, this type of charging would take a very long time to completely recharge a depleted battery but it is useful for extending battery life, especially when charging occurs continuously.

2. Photovoltaic Cells 2.1. Photovoltaic cells generate a voltage in response to light. This may be used to power the device directly depending on the power requirements of the sensors and features or to recharge a battery or super-capacitor.

3. Rectenna 3.1. Rectennas use ambient radio-frequency energy from that of radio transmissions, mobile communications, Wi-Fi networks, etc. to induce small currents within an antenna which are rectified and managed in such a way that they may be used to trickle charge a rechargeable power source.

4. Shake-to-Charge 4.1. Incorporating a freely mobile magnet within conductive coils will allow the system to generate current in the conductive coil when the device is shaken or the magnet is forced to move by other means. The motion of the magnet induces a current in the coils which may be used to charge a battery or other power source.

Distribution

It is preferable to have all electronic components in close proximity to one another to make the distribution of power easier to manage. However, given the requirements of the device, this may not be possible. In the cases where some electronics are housed in the MDI adapter and others are housed towards the mouthpiece or mask adapter, a few power distribution strategies exist.

1. Conductive Paths Along Body 1.1. This method uses only one power source (e.g. one battery) located in either the mouthpiece/mask adapter or the MDI adapter whose power is transferred to the other component through the body. In each case, contacts at both ends of the body ensure the power is reliably transmitted to the other components. The contacts are formed in such a way as to still allow assembly and disassembly of the device for cleaning while providing repeatable, robust connections on each assembly. These conductive paths are also used for data communications between the hardware at the front and the microcontroller at the back.

1.1.1. Conductive Resin

Conductive resin may be used to mold conductive pathways directly into the body component. This would be done through a dual-shot or insert molding manufacturing method.

1.1.2. Conductive Ink

Conductive ink may be used to form the conductive path and can be either pad printed or screen printed onto the body.

1.1.3. Flexible Electronics and Adhesive

Flexible, low profile wires may be used and these could be secured to the body through the use of an adhesive.

2. Two Batteries with Wireless Communications 2.1. The hardware at the mouthpiece/mask adapter end of the VHC may be powered by a completely independent power source (e.g. battery) from the power source at the MDI adapter end of the VHC. Each end of the chamber would likely require its own microcontroller or other processor 502 to handle inputs and outputs at those respective ends. It is very likely in this scenario that the two microcontrollers would need to communicate to share data. This could be done via Bluetooth or other means.

MDI Identification

Identification of the MDI provides assurances to the patient, prescriber and payer that the approved medication regimen is being adhered too. Additionally, it may be used to alert the patient if the wrong drug has been inserted into the chamber which may help in preventing over and under dosing of particular medications. The methods of identification below may be used on their own but may also be used in combination to confidently identify the MDI.

For example, and referring to FIG. 13, a photodiode 222 and color detector sensor 224, or MDI identifier, may be disposed on the exterior surface of the chamber housing wall, or on the backpiece, and be directed toward the MDI, including the actuator boot and container. A unique tag may 226 be attached to each MDI, or a unique rescue tag may be attached to a rescue MDI and a unique controller tag attached to a controller MDI. The sensor 224, e.g., color detector sensor, detects the presence of the tag to identify each specific MDI or to identify each MDI by category, e.g., rescue or controller. The tag may be configured with different colors, barcodes, magnetic properties, surface properties such as reflection/absorption etc.

1. Color Sensing of MDI Boot 1.1. Mouthpiece Color

Referring to FIG. 68, MDI's come in a variety of different colors and some have two color tones differentiating the handle from the mouthpiece. Color sensing may be used to help identify the MDI that is inserted into the MDI adapter by getting a specific color code reading (e.g. RGB, CMYK, L*a*b*) from the mouthpiece portion of the MDI. As the MDI is inserted into the adapter, the color sensing hardware, or sensor 224 (MDI identifier), is triggered to collect the color information from the mouthpiece of the MDI. This color code is then analyzed through software and compared to a database of MDI and their respective color codes. Various algorithms may be used for the comparison and the closest match is used for the MDI identity. Alternatively, the MDI boot color code may be used as an input to a multifactorial algorithm which uses several inputs to identify the MDI.

1.2. Handle Color

As shown in FIG. 68, similar to the mouthpiece color sensing but instead of having the color sensor 224 positioned to obtain the mouthpiece color code, it is positioned to analyze the color of the handle portion of the MDI boot.

1.3. Mouthpiece and Handle Colors

Combining 1.1. and 1.2. to help differentiate two-tone MDI boots.

2. Color Sensing of Aerosol Plume 2.1. There are numerous formulations across all MDI and this may be reflected in different color codes of the aerosol plume. Color sensing hardware is positioned near the mouthpiece of the MDI boot within the MDI adapter and during MDI actuation, the color code of the aerosol plume is collected and compared to a database of various MDI. Various comparison algorithms may be used with the closest match being used for MDI identification. Alternatively, the aerosol color code may be used as an input to a multifactorial algorithm which uses several inputs to identify the MDI.

3. Mouthpiece Shape Detection 3.1. Force Sensitive Resistors (FSR)

Referring to FIG. 72, FSRs 208 are positioned in the MDI adapter such that during MDI insertion, the resistors are compressed by an amount proportional to the size of the MDI mouthpiece in that particular direction causing their signal to change accordingly. Their resistance values are compared to those of the MDI in a database. Various comparison algorithms may be used with the closest match being used for MDI identification. Alternatively, the resistance values may be used as an input to a multifactorial algorithm which uses several inputs to identify the MDI.

3.2. Strain Gauges

The MDI adapter port is intentionally undersized such that it must stretch as MDI are inserted, as shown in FIG. 70. The total strain and locations of high and low strain detected by the strain gauges 208 may be analyzed and compared to a database of different MDI and their strain values to help identify the MDI.

3.3. Referring to FIGS. 69 and 71, and linear action potentiometers 210, similar to the FSR method, potentiometers which are adjusted through linear-motion are adjusted according to the size of the MDI mouthpiece in a particular direction. The resistance values gathered by the system upon MDI insertion are compared to values stored in a database for various MDI. These potentiometers have a biasing spring so that they return to their original positions when the MDI is removed.

4. Mouthpiece Length 4.1. Tactile or Slide Potentiometer

The length of the mouthpiece portion of the MDI may be used as a distinguishing factor.

Upon full insertion into the MDI adapter, the length of the mouthpiece may be measured by means of a tactile or slide potentiometer and compared to the various lengths stored in the system's database as shown in FIG. 69.

5. Resistance to Flow Profile 5.1. Resistance to Flow Profile

Referring to FIGS. 54 and 55, flow through the chamber may monitored as disclosed herein by way of various sensors. The flow may be used to help identify the MDI.

Using this flow information coupled with data from a differential pressure sensor 78 comparing the pressure at the MDI mouthpiece to atmospheric pressure, the Pressure vs. Flow profile can be collected for the MDI. Comparing this profile to those in a database of MDI, a match can be found which could identify the MDI. Alternatively, the resistance profile may be used as an input into a multifactorial algorithm.

6. MDI Sound at Certain Flow Rate

Figure 25:
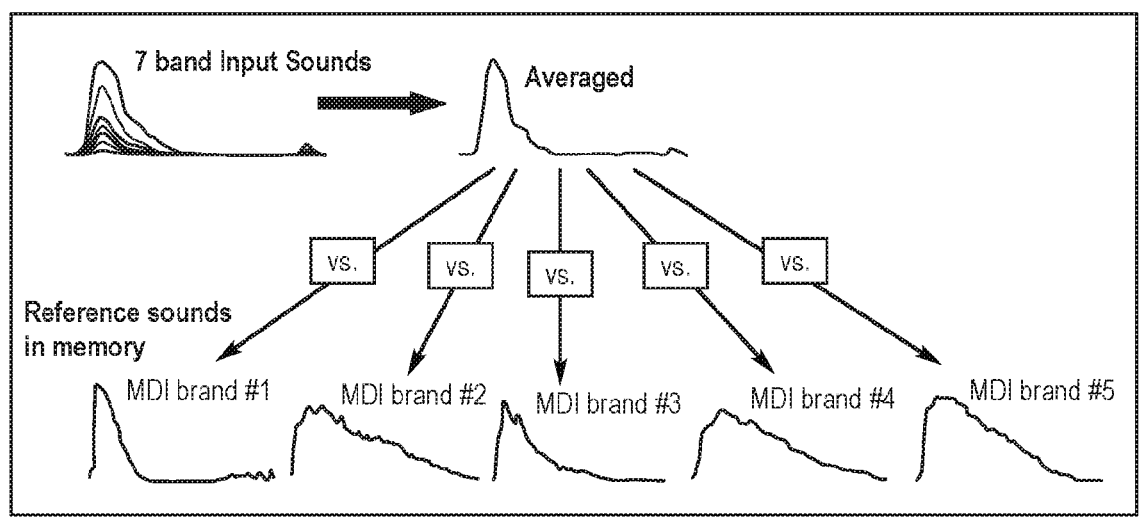
FIG. 25 is a schematic showing MDI recognition via sound.

Referring to FIGS. 24-28, an audio interface includes an equalizer circuit (e.g., 7-band), which divides the audio spectrum into seven bands, including for example but not limited to, 63 Hz, 160 Hz, 400 Hz, 1 kHz, 2.5 kHz, 6.25 kHz and 16 kHz. The seven frequencies are peak detected and multiplexed to the output to provide a representation of the amplitude of each band. The bands are processed by the microcontroller to average the bands into a single amplitude (dB) v. time signal (FIG. 25). The unique sound produced by different brand MDI's may then be compared to a known stored sound within the memory or cloud database. Using normalized correlation, the input sound may be compared to the reference sound with a high degree of certainty. The actuation sound is captured and stored upon MDI actuation, and the comparison and determination may be processed after a treatment, in order to free up processing power for other VHC tasks during treatment, or during treatment, depending on the available processing power. If processing is fast enough, the MDI actuation may be analyzed in real time, and provide feedback about whether the MDI nozzle, or support block, is plugged or partially plugged due to low or insufficient sound produced. The feedback may also include information about whether the MDI needs to be shaken and/or primed, or checked for adequate remaining dose counts.

6.1. A database may be generated which contains the frequency spectrum or dominant frequencies of all MDI at specific flow rates. In use, when this flow rate is reached, the sound is sampled through a microphone and compared to the sound profiles stored in the system database. Various algorithms may be used for this comparison.

7. MDI Sound at Actuation 7.1. A database may be generated which contains the frequency spectrum or dominant frequencies of all MDI actuation sounds. When actuation occurs, the recorded sound is quantitatively compared to those stored in the system's database and the closest match is determined.

8. MDI Sound when Percussed 8.1. A database may be generated which contains the frequency spectrum or dominant frequencies of all MDI sounds when percussed or hammered on. Upon insertion into the MDI adapter, a mechanical hammer is triggered such that it impacts the MDI in the mouthpiece region. The sound that is generated is dependent on the shape, volume, stiffness of the MDI boot and its fit with the MDI adapter. This sound can then be compared quantitatively to those in the system's database.

9. Image Processing 9.1. Read the Label

Figure 4:
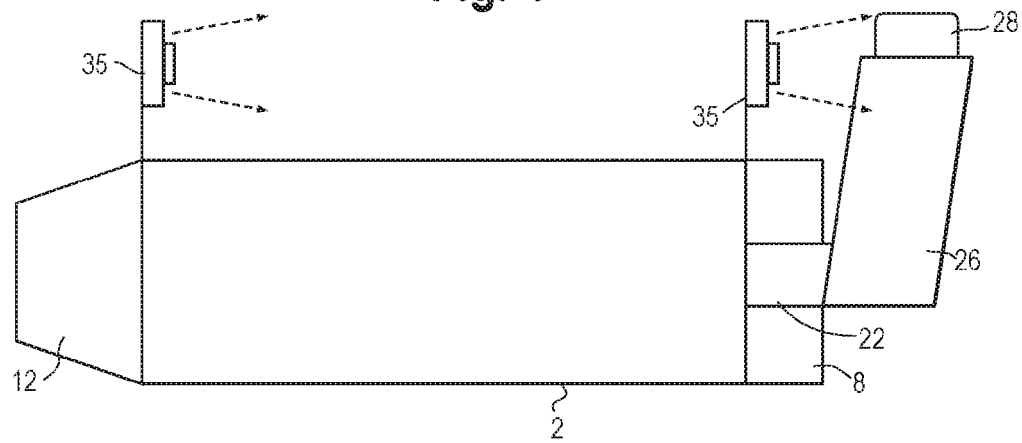
FIG. 4 is a side view of another embodiment of a smart VHC.
Figure 5A:
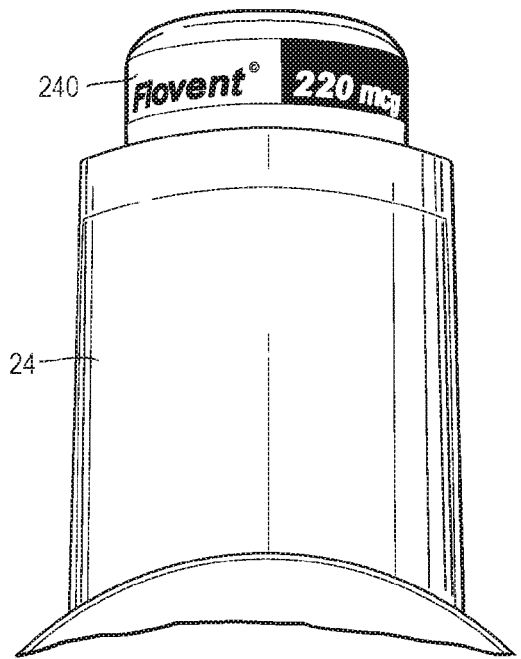
FIGS. 5A and B are actual and greyscale images of a medication container.
Figure 5B:
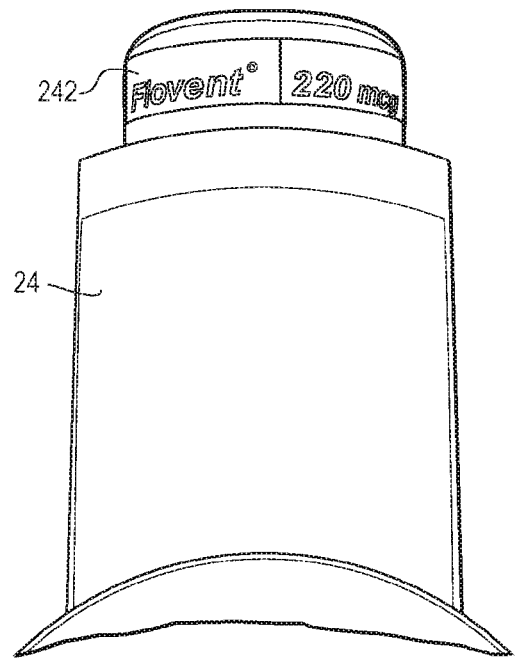
Figure 6:
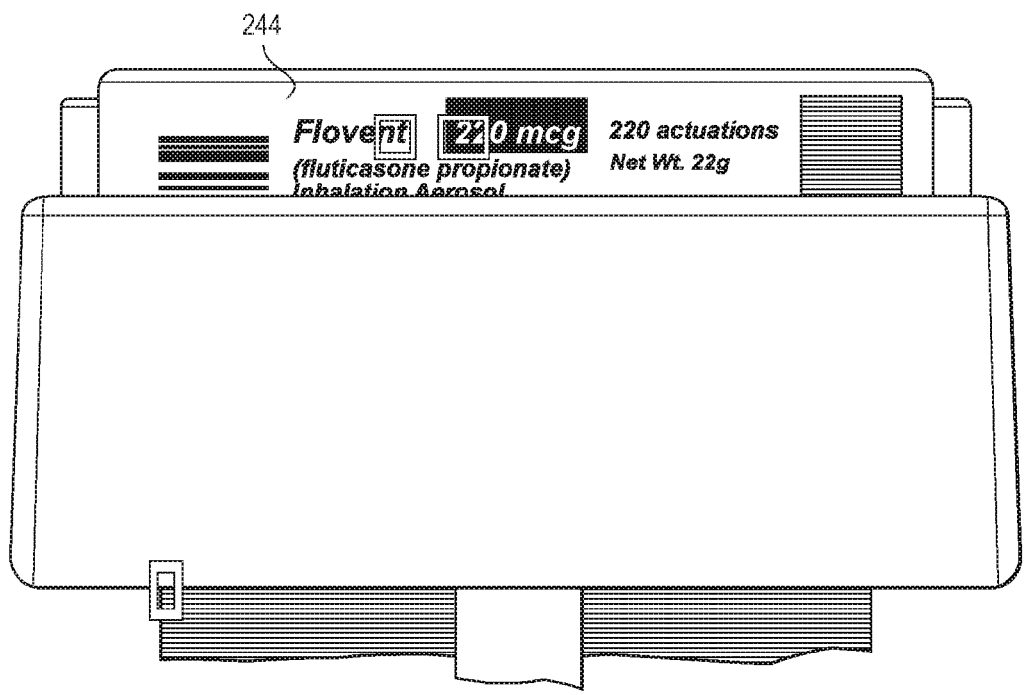
FIG. 6 is an image showing the proper identification of the medication container shown in FIG. 5A.

Use text recognition software to "read" the text on the MDI boot and/or MDI canister. For example, and referring to FIG. 4, the camera 35, or other image sensor (MDI identifier), is mounted to the chamber housing, for example adjacent the input or output ends thereof, or at any location therebetween. The image sensor may also be coupled to the mouthpiece assembly and/or to the backpiece. The camera or image sensor captures an image of the MDI, including various textual information presented on a label 240 coupled to the container and/or actuation boot. An image processing algorithm and/or machine learning technique may be used to extract the textual information, unique shape and/or unique feature that reveals the type and identify of MDI being associated with the VHC. The captured image may further be stored into memory and compared with different types of MDI's in a database to narrow the selection. Referring to FIGS. 5A, 5B and 6, the camera or image sensor capture the image of the MDI and converts to a greyscale image 242 as shown in FIG. 5B. The processor then extracts a plurality of templates (e.g., three) from the captured greyscale image and compares the templates/image with stored images in a database. As shown in FIG. 6, the processor correctly identified the MDI, referring to label 244.

9.2. Combine Color, Shape

Analyze color and shape from a digital image or series of digital images and compare these to colors and shapes of various MDI in a database.

9.3. Feature Recognition

An image kernel may be used to scan the image for similarities to the kernel itself. For example, a kernel in the form of a GSK label may be used to identify GSK boots by computing the correlation product for each position of the kernel on the image and checking to see if the correlation coefficient exceeds a certain threshold value which would indicate good agreement.

10. Spectroscopic Drug ID 10.1 Single Wavelength Infrared/UV

Infrared and ultraviolet spectroscopy are methods used to determine the chemical structure and makeup of a sample. All chemicals absorb infrared and ultraviolet radiation to some degree and will absorb some wavelengths of light more than others depending on the bonds present in their chemical structure. Using a light source of a controlled wavelength, the absorbency of the drug to that particular wavelength can be analyzed by shining the light through the aerosol towards a light detector. This absorbency can then be compared to values in the MDI database.

10.2. Multiple Wavelength Infrared/UV

Similar to 10.1. except that multiple wavelengths may be used.

11. Force to Fire 11.1. Using a force sensitive resistor (FSR), the force at MDI actuation can be determined. This would need to be coupled with MDI actuation detection as described herein. As soon as MDI actuation is detected, the force is recorded and compared to values stored in the MDI database.

12. Temperature of Aerosol (Aerosol/Air Temperature or Contact Evaporation)

12.1. Single Point

Temperature can be monitored at a fixed distance from the MDI and using the temperature detected during MDI actuation, this information can be compared to temperatures stored in the system's MDI database. Despite all MDI using the same family of propellant (HEA 134a or HFA 227), temperature differences of the aerosol are seen at fixed distances from the MDI as a result of the different drug formulations.

12.2. Temperature Vs. Distance

Further to embodiment 12.1., several temperature sensors may be used at fixed distances from the MDI to collect a temperature profile during MDI actuation. This profile may be used and compared to profiles in the system's database.

Figure 73:
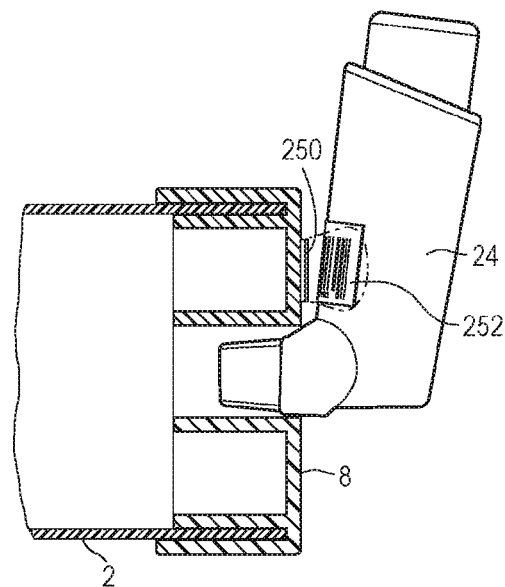
FIG. 73 is an end view of another embodiment of a VHC.

13. RFID on MDI from Supplier 13.1. Referring to FIG. 73, Radio Frequency Identification (RFID) tags or labels 252 may be adhered to or molded in to the MDI by the manufacturer or supplier of the medication. In this case, it is possible to read the RFID label on the MDI with an RFID reader 250 within the MDI adapter or coupled to the backpiece 8 or other component of the VHC.

14. RFID on Dose Counter (Integrated or OEM)

14.1. Similar to embodiment 13.1., RFID tags may be incorporated into integrated or dose counter modules and these may be read with the RFID reader incorporated with the chamber.

15. Label Placed on MDI by User 15.1. RFID

Similar to embodiments 13.1. and 14.1., a RFID tag may be read from the MDI. In this embodiment, the RFID comes in the form of a sticker, adhesive patch or other form that is placed on the MDI by the user.

15.2. Bar Codes (1D and 2D)

Similar to embodiment 15.1. except a bar code may be used in place of a RFID. The chamber then includes a bar code scanner as opposed to a RFID reader.

16. Access Patient Medication List on Cloud 16.1. Bluetooth/Wi-Fi Access

A user's digital medical records may be accessed through the internet and their MDI medication prescriptions may be used to help identify the MDI being used with the VHC. Alternatively to ensure security, the healthcare provider or payer may initiate a 'profile' for the user and select their MDI medication(s), which will then be communicated to the VHC via Bluetooth or Wi-Fi.

17. Communication with Smart Inhalers 17.1. Bluetooth/Wi-Fi Communications

Smart inhalers are already used to track adherence of MDI. Communication with these inhalers will allow the VHC to directly identify the MDI being used. This may be accomplished through Bluetooth or Wi-Fi communications.

18. Manually Selected by User 18.1. Manual Selection

Referring to FIG. 19, user input buttons 260, for example with different colors, shapes or indicia. The user 66 would push the appropriate button, e.g., blue, associated with a rescue MDI, or red, associated with a controller MDI. A combination of pressing both buttons would communicate a combination MDI was being used. Each button may also have a visual indicator, such as a light, which illuminate, and stay illuminated for a predetermined time period (or until the treatment is completed), when pressed. If the wrong indicator is displayed, it provides indicia to the user to start over. A single button may also be used, with a button push being associated with one of the rescue or controller MDI, and with no button push being associated with the other type of MDI. When reviewing patient use data, the prescriber would know which type of drug is associated with each of the rescue and controller MDI's. In addition, the user may input the drug information through an application on a computer, for example in a user profile setting. The user may share the logged medication activity with the prescriber and/or payer.

The user may be given the option of manually selecting the MDI being taken. This may be done at each dose or the list of medications may be specified by the user once upon receiving the smart chamber. For users with only one prescribed medication, the latter method would serve to confidently identify the MDI being used every time whereas for users with multiple medications, this would be used to short list the possible MDI candidates which would then need to be further identified by the system using means described in other embodiments.

19. Capacitance/Dielectric Constant Detection 19.1. Dielectric Constant Detection Two oppositely, electrically charged features are separated by an air gap forming an open capacitor. Upon MDI actuation, this air gap is infiltrated with aerosol. Assuming that aerosols have different dielectric constants from one another, the capacitance change of the open capacitor can be measured and this capacitance value can be matched to those in a database of known aerosols and used to identify the MDI.

20. Resonant Frequency of MDI 20.1. A sound generator is located within the VHC which produces a range of frequencies in a sweeping fashion. When the resonance frequency of the MDI is produced by the sound generator, a spike in volume may occur which can be detected by means of a microphone.

21. Infrared Reflection of MDI Boot 21.1. Using infrared (IR) emitter(s) and IR detector(s), an infrared "signature" may be generated for various MDIs. The IR emitter(s) and detector(s), and positioning thereof, may be the same as the white LED and color sensors discussed above and shown in the attached Figures. IR Radiation is directed towards the mouthpiece and/or handle portion of the MDI boot and the amount of radiation absorbed/reflected is used to identify the MDI. Specifically, in this embodiment, the amount of radiation reflected is detected by the IR detector and this value is compared to those present in a prerecorded MDI database. The material of the MDI boot, its shape and surface finish all play a role in the amount of reflected IR radiation. A single wavelength IR LED/Detector may be used or several IR LED/detectors with different IR wavelengths may be used.

Mask Force and Seal Feedback

When delivering respiratory medications to users, facemasks 600 are often used. For example, facemasks may be coupled to the mouthpiece assembly 12, or output end, of a VHC 3. In order to maximize the drug delivery, it is important to ensure that a proper seal is formed between the mask and the user's face 602. The proper seal may be determined by measuring the force applied to the mask, VHC or other delivery device, e.g., nebulizer or OPEP device, or by registering contact between the mask and the user's face.

Figure 29:
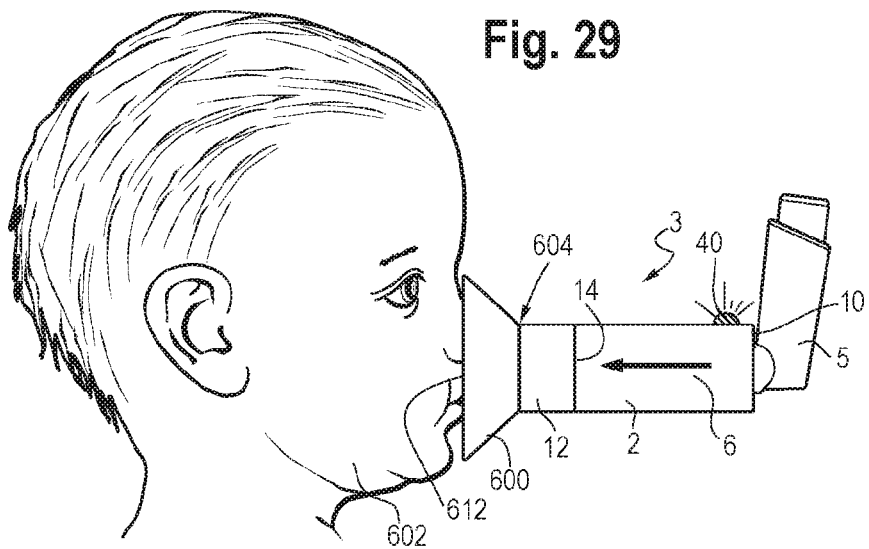
FIG. 29 is a side view showing the use of one embodiment of a medication delivery system.

In one embodiment, shown in FIG. 29, a medication delivery system includes a medication delivery device, e.g., VHC, having an input end 10 and an output end 14. A mask 600 is coupled to the output end. The mask, and delivery device, are moveable along a longitudinal axis 6 to an engaged position with a user's face 602. A force sensor 604 is disposed between the mask 600 and the input end 10 of the medication delivery device. For example, the force sensor 604 may be mounted between the mask 600 and the valve assembly 12 (e.g., mouthpiece assembly), or between the valve assembly 12 and the chamber housing 2. The force sensor 604 may be a load cell that converts mechanical deformation or displacement into electrical signals via a strain gauge, or a piezoelectric sensor that converts changes in force into electrical change through a piezoelectric effect. The force sensor communicates a signal to the computer 500 and processor 502, which may be mounted, for example to the backpiece 8. The VHC microcontroller monitors the force being applied and provides feedback to the user, or caregiver manipulating the delivery device, to either increase, decrease or maintain the force being applied. For example, the force required to achieve a desirable seal may range between 1.5 and 7 lbs. Feedback to the user includes an indicator, whether a visual indicator 40 (e.g., LED), an auditory indicator (speaker) or vibration indicator. The force sensor 604 is responsive to the force being applied along the longitudinal axis to the mask by the medication delivery device. The indicator provides feedback to the user regarding the amount of force being applied to the mask, whether too little or too much, and/or not uniform around the periphery.

Figure 30:
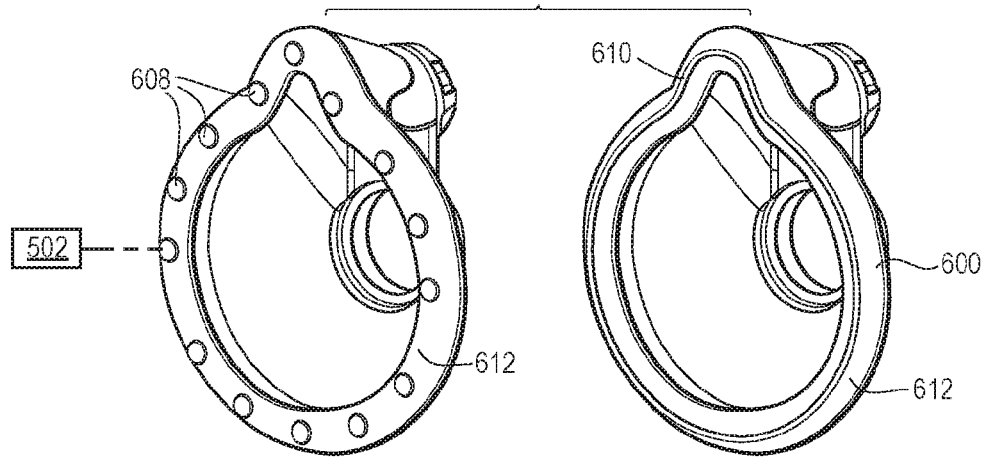
FIG. 30 is a perspective view of alternative embodiments of a mask configured with contact sensors.
Figure 31:
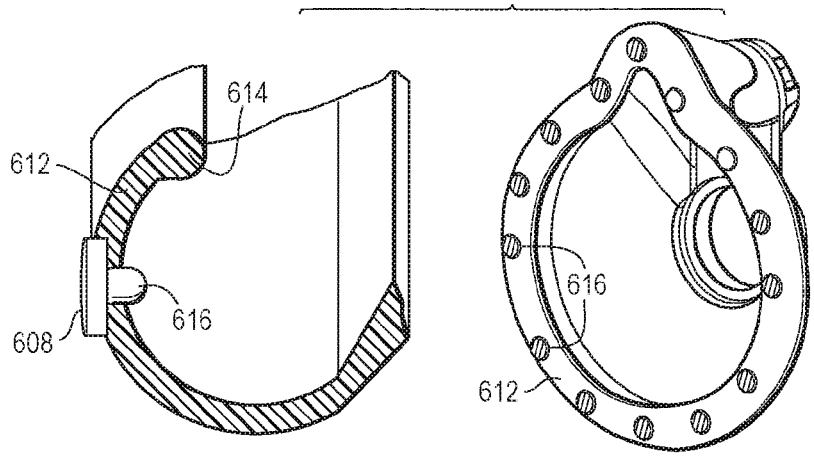
FIG. 31 is a schematic view of a mask, and an enlarged cross-section of a portion of the mask sealing edge.

In another embodiment, shown in FIGS. 30 and 31, contact sensors 608, 610 may be incorporated into the mask 600 to monitor, sense and signal appropriate contact with the user's face around a perimeter of the mask. For example, the mask is configured with a sealing portion 612 adapted to engage the face 602 of the user. The sealing portion 612 may include a turned-in C-shaped lip, terminating at a free end 615. One or more sensors 608 are coupled to the sealing portion, wherein the force sensor is responsive to a force being applied to the sealing edge. In one embodiment, a plurality of sensors are embedded in the sealing portion, and are distributed around the periphery of the mask, or a length of the sealing portion, in spaced apart relationships as shown in FIGS. 30 and 31. In an alternative embodiment, shown in FIG. 30, the sensor 610 comprises a continuous strip extending around the sealing edge.

Referring to FIGS. 30 and 31, an indicator 616 is in communication with the sensor and is adapted to provide feedback to the user regarding the amount of force being applied to the sealing edge, or whether contact has been made with the user's face. For example, the indicator may include a visual, auditory or vibratory indicator. In one embodiment, the visual indicator includes a plurality of lights 616 (e.g., LED's) distributed and spaced apart along the sealing edge, or the periphery of the mask. In one embodiment, the plurality of visual indicators are associated respectively with, and directly coupled to, the plurality of sensors.

Figure 32:
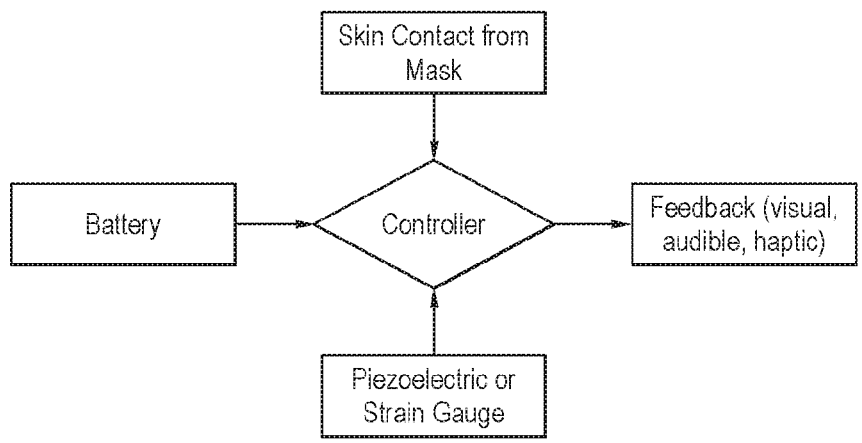
FIG. 32 is a schematic showing the input/output for a controller.
Figure 33:
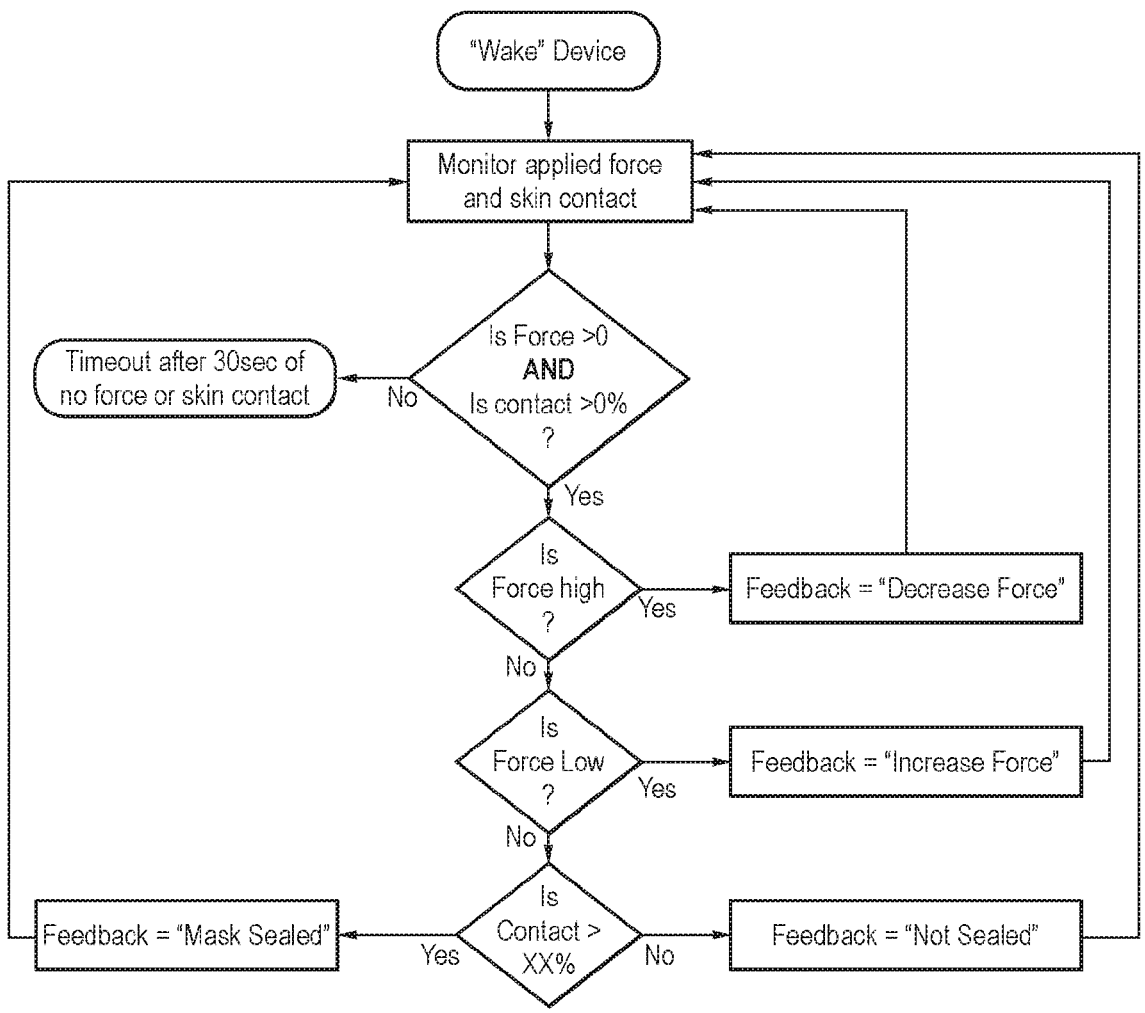
FIG. 33 is a flow chart shown illustrating use of a mask.

In operation, and referring to FIGS. 32 and 33, the user or caregiver applies a force to the mask 600, engages the user's face 602 with the sealing edge 612 of the mask, senses the force being applied to the mask, or alternatively that contact is being made at a particular location on the sealing edge, and provides feedback to the user with an indicator 616 about the force and/or contact being applied. The user/caregiver may then adjust the force being applied to the mask. In one embodiment, the feedback would be illumination of the lights 616 that are coupled to contact sensors 608, 610 where contact has been detected, and with lights not illuminating where contact has not been detected. Similarly, a portion of indicator lights may illuminate where various force sensors have detected a sufficient force has been applied, and lights not illuminating along portions of the mask where insufficient force is being applied. In other embodiments, the lights may illuminate in different colors, or turn off, if too much force is being applied.

Once active, the controller (which may be implemented to include one or more computer 500 elements such as a processor 502 (FIG. 83)) may analyze the output of the force or contact sensor and estimate the quality of the seal. Combining the measurement of force being applied, together with a measurement of the contact with the user's face, allows the device to provide information about whether an adequate seal is formed.

Active Valve

When using various medication delivery devices, such as a VHC, a slow inhalation (<30 L/min maximum), followed by a breath hold, may improve significantly lung deposition of the drug. While various auditory aids are available to provide feedback to the user that the inhalation rate is too high, they are passive, and do not control the rate. As such, they may be misunderstood or confused with positive feedback (e.g., inhaling quickly to make the whistle sound is good, rather that the intended feedback that the sound should be avoided).

As shown in FIGS. 34-37, one embodiment of a valve 700 actively adjusts the resistance to opening or closing during inhalation (or exhalation) so as to actively control the inhalation or exhalation rate. The system may also provide feedback to the user that the valve is actively controlling flow so that the user may adjust the flow rate.

Figure 35:
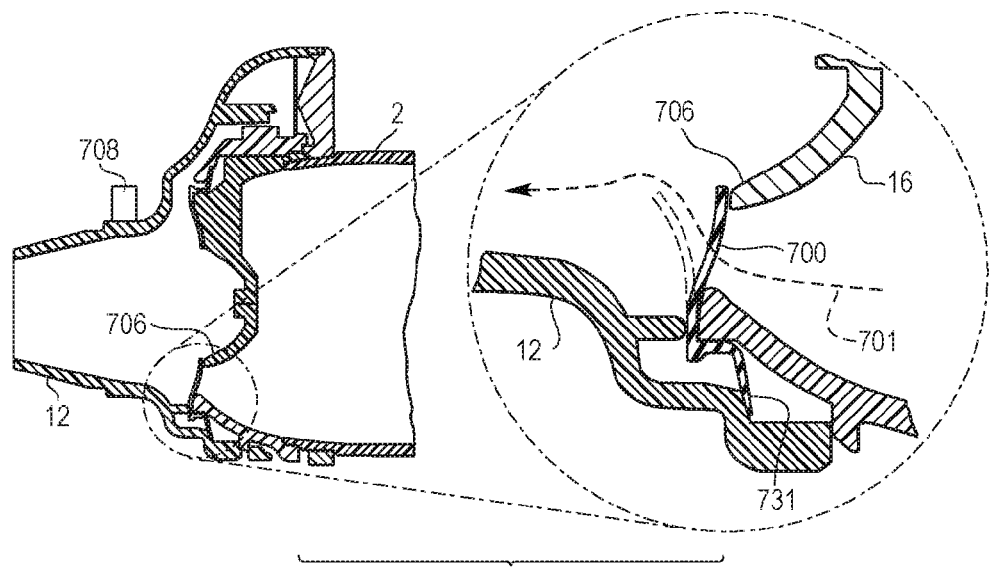
FIG. 35 is a cross-sectional view of one embodiment of an active valve disposed in a flow channel of a medication delivery system.
Figure 36:
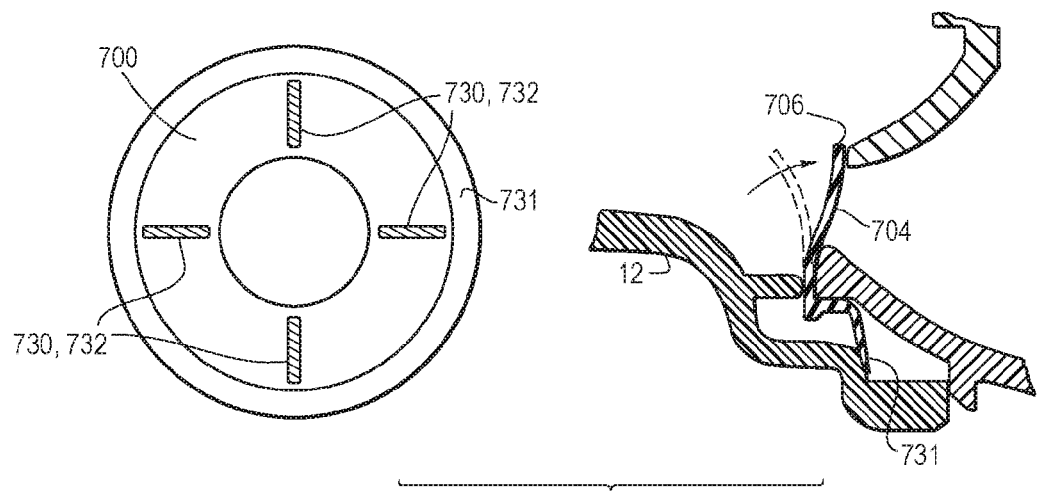
FIG. 36 is an end view of one embodiment of the valve shown in FIG. 35.
Figure 87:
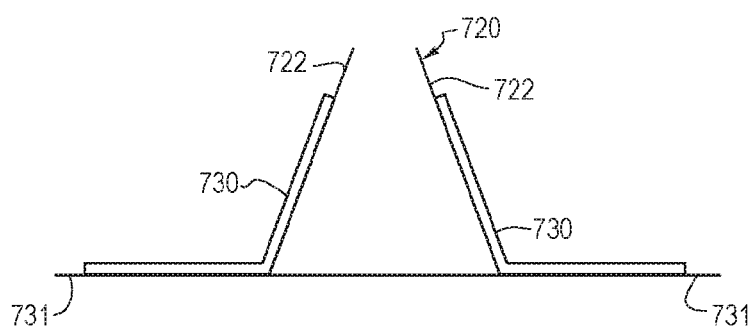
FIG. 87 is a side view of one embodiment of an active valve.

The valve may be configured in various forms, including an annular doughnut valve, as shown in FIGS. 35 and 36, as a duckbill valve 720, as shown in FIG. 87, or as other valves with moveable, bendable or deformable features. The annular valve includes a central opening 702 and an annular flange 704 that bends or deforms outwardly such that the flange is lifted off of a valve seat 706, thereby allowing flow through the opening 702. The duckbill valve 720 has a pair of opposing flaps 722, which open to form an opening in response to flow therethrough. The valve may be made of liquid silicone rubber (LSR).

An actuator portion 730 is applied to, or embedded into, the valve. For example, the actuator portion may be made of an electroactive polymer (EAP). When stimulated by an electric field, the LSR portion becomes stiffer, and resists opening. In one embodiment, the annular flange 704 of the valve is configured with a plurality of EAP strips 732 (shown as four). Other configurations, including more or less strips, or differently shaped portions, would also be suitable. In another embodiment, at least one of the flaps 722 of the duckbill valve 720, and both flaps in one embodiment, are configured with an embedded electroactive polymer actuator portion 730, for example a strip. It should be understood that the actuator portions, or EAP feature, may also be applied to the exhaust valve or exhalation portion 731 of the valves.

The VHC, or other medication delivery device, has a housing 2, 12 defining a flow channel 701. The valve 700, 720 is disposed in the flow channel. The valve is moveable between first and second configurations, for example open and closed (completely or partially) in response to a flow through the flow channel. The flow may be inspiratory or expiratory. The valve is reconfigurable between a first condition and a second condition in response to a stimuli, for example an electrical stimuli. For example, the first and second conditions are first and second stiffnesses, or resistance to bending and/or deformation. The valve has a first resistance to moving between the first and second configurations, for example resistance to bending or deformation, when the valve is in the first condition, and the valve has a second resistance to moving between the first and second configurations when the valve is in the second condition, wherein the first resistance is greater than the second resistance. An actuator 708 applies the electrical stimuli.

Figure 34:
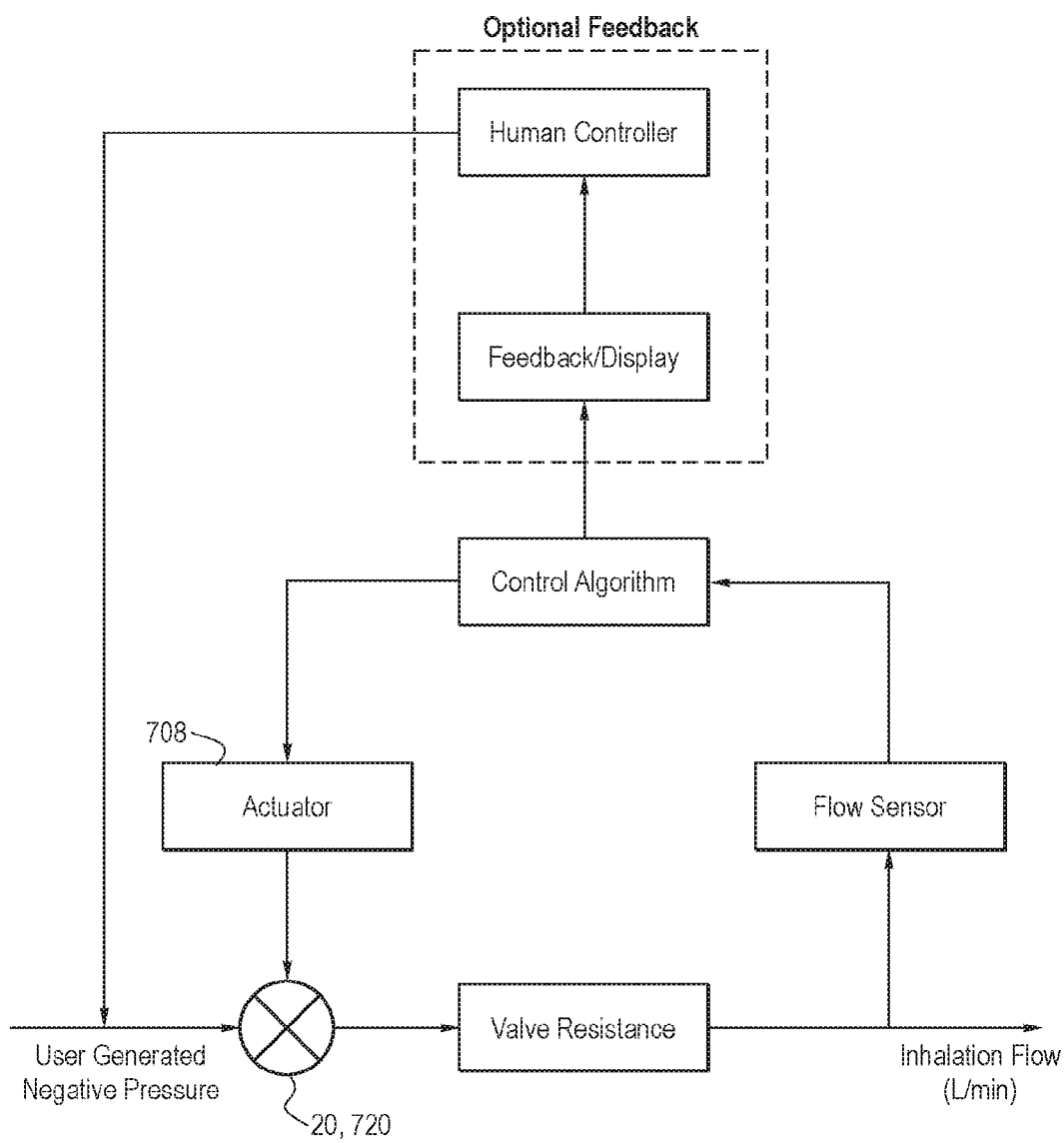
FIG. 34 is a flow chart illustrating use of an active valve.

In operation, a flow is created through the flow channel of the housing, for example by patient inhalation or exhalation. The flow causes the valve 700, 720 to move between first and second configurations in response to the flow through the flow channel. Depending on the flow rate calculated by various sensors and methods described herein in other sections of this disclosure, the actuator 708 may be instructed to apply a stimulus (e.g., electrical) to the valve as shown in FIG. 34. The valve is reconfigured from a first condition to a second condition in response to the stimulus. The flow through the channel is altered, for example restricted or increased, when the valve is reconfigured to the second condition, e.g., made more resistant to bending or deforming such that the opening formed by the valve, or between the valve and valve seat, is restricted or maintained smaller.

Figure 37:
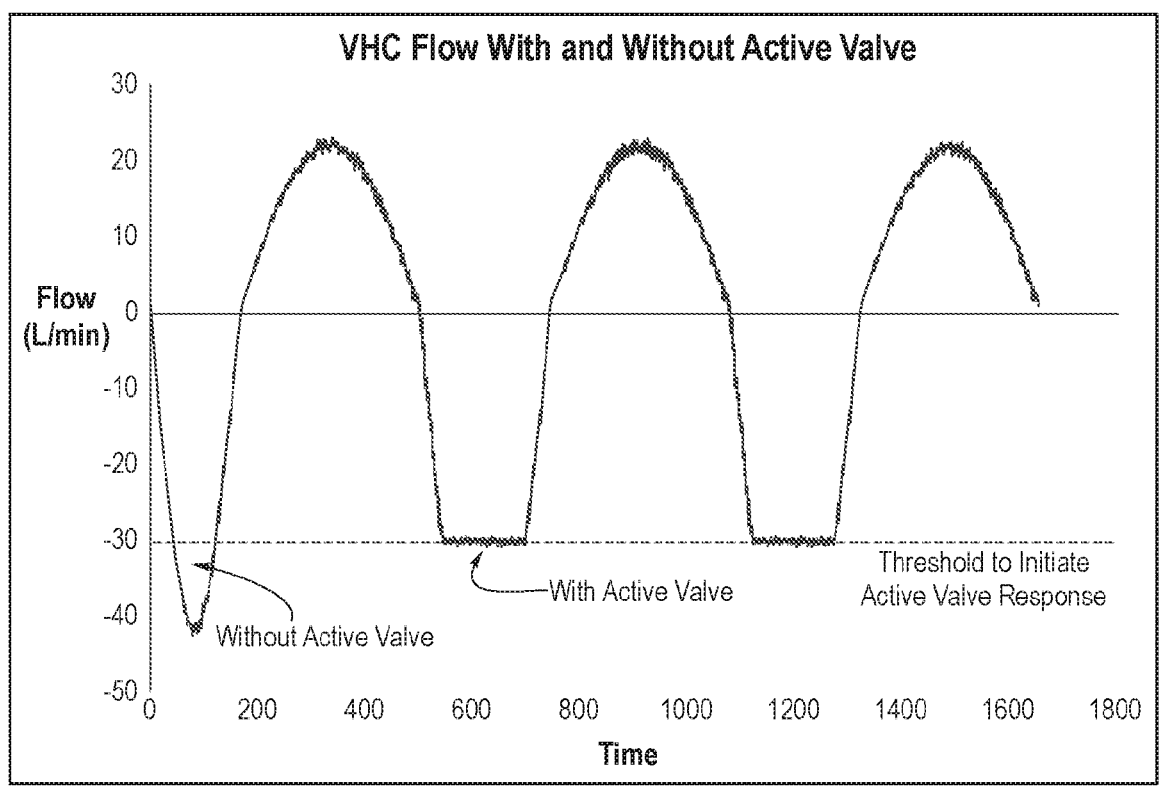
FIG. 37 is a flow v. time graph showing an inhalation and exhalation cycle with and without an active valve.

As shown in FIG. 37, the valve may be actively managed such that the flow rate through the valve, as sensed and detected as described above, does not exceed a predetermined threshold, e.g., 30 L/min.

In any of the above-described embodiments of smart devices, the controller or other processing element that communicates with or controls the sensors, gauges or switches may be integrated into, positioned on or in, or remotely located from the smart device itself. It should be understood that the various sensors, gauges or switches may serve multiple functions and may be used in various combinations, all in communication with the controller or other processing element. Additionally, for any of the smart devices described above, some or all of the data gathered and feedback provided to a user of the device by sensors, switches or gauges may simultaneously be transmitted to a remotely located caregiver. The remotely located caregiver or monitoring agency may intervene to provide further advice or information during a therapy session. Alternatively, the data and feedback transmitted to the caregiver or monitoring agency in parallel with the user may be stored remotely for later assessment by medical professionals. Concurrent transmission to a remote source of information, including the sensed data and any feedback, may also prevent problems with tampering or corruption of data stored on the smart device itself.

The battery or other power supply for any controller circuitry, sensors, gauges and switches may be rechargeable or removable in different embodiments of smart devices described herein. In order to minimize battery drain, certain of the sensors may be configured for a predetermined sampling frequency rather than a continuous measurement mode. Also, the circuitry on the smart device may only activate upon the detection of a particular event and may automatically turn off after a predetermined period from the initial trigger or after sensed idle period for the device.

Although the present invention has been described with reference to preferred embodiments. Those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. A medication delivery system comprising:
a medication delivery device having an input end and an output end;
a mask coupled to the output end, wherein the mask is moveable along a longitudinal axis to an engaged position with a user's face and is configured for forming a seal between the mask and the user's face;
a force sensor mounted on the medication delivery device and disposed between the mask and the input end of the medication delivery device, wherein the force sensor is configured to sense a force applied to the medication delivery device and is responsive to a force being applied along the longitudinal axis to the mask by the medication delivery device; and
an indicator configured to provide feedback to the user or a caregiver regarding an amount of contact made between the user's face and the mask and/or the force being applied along the longitudinal axis to the mask by the medication delivery device.

2. The medication delivery system of claim 1, wherein the medication delivery device comprises a body portion defining the input end and a valve assembly coupled to the body portion and defining the output end, wherein the mask is coupled to the valve assembly.

3. The medication delivery system of claim 2, wherein the force sensor is disposed between the mask and the valve assembly.

4. The medication delivery system of claim 2, wherein the force sensor is disposed between the valve assembly and the body portion.

5. The medication delivery system of claim 1, wherein the mask comprises a contact sensor configured to sense engagement of the mask with the user's face.

6. The medication delivery system of claim 5, wherein the contact sensor is configured to monitor, sense and signal appropriate contact with the user's face.

7. The medication delivery system of claim 5, wherein the contact sensor is coupled to a sealing portion of the mask and distributed around a periphery of the mask.

8. The medication delivery system of claim 7, wherein the contact sensor comprises a continuous strip extending around the sealing portion of the mask.

9. The medication delivery system of claim 7, wherein the contact sensor comprises a plurality of spaced apart contact sensors positioned around the periphery of the mask.

10. The medication delivery system of claim 9, wherein the indicator comprises a plurality of indicators associated with the plurality of contact sensors respectively.

11. The medication delivery system of claim 10, wherein the plurality of indicators comprises a plurality of lights.

12. The medication delivery system of claim 1, wherein the indicator comprises a visual indicator.

13. The medication delivery system of claim 1, wherein the indicator comprises an auditory indicator.

14. The medication delivery system of claim 1, wherein the indicator comprises a vibratory indicator.

15. The medication delivery system of claim 1, further comprising a controller configured to analyze an output of the force sensor and estimate a quality of the seal.

16. The medication delivery system of claim 1, wherein the medication delivery device comprises one of a valved holding chamber, a nebulizer or an oscillating positive expiratory pressure device.

17. The medication delivery system of claim 1, wherein the indicator is configured to provide the feedback to the user or the caregiver about a desirable seal when the force being applied along the longitudinal axis to the mask is between 1.5 and 7.0 lbs.

18. The medication delivery system of claim 1, wherein the indicator is disposed on the medication delivery device.

19. A medication delivery system comprising:
a medication delivery device having an input end and an output end;
a mask coupled to the output end, wherein the mask is moveable along a longitudinal axis to an engaged position with a user's face and is configured for forming a seal between the mask and the user's face;
a force sensor mounted on the medication delivery device and disposed between the mask and the input end of the medication delivery device, wherein the force sensor is configured to sense a force applied to the medication delivery device and is responsive to a force being applied along the longitudinal axis to the mask by the medication delivery device;

a contact sensor configured to sense engagement of the mask with the user's face; and an indicator configured to provide feedback to the user or a caregiver regarding an amount of contact made between the user's face and the mask and/or the force being applied along the longitudinal axis to the mask by the medication delivery device.

20. The medication delivery system of claim 19, wherein the medication delivery device comprises a body portion defining the input end and a valve assembly coupled to the body portion and defining the output end, wherein the mask is coupled to the valve assembly.

21. The medication delivery system of claim 20, wherein the force sensor is disposed between the mask and the valve assembly.

22. The medication delivery system of claim 20, wherein the force sensor is disposed between the valve assembly and the body portion.

23. The medication delivery system of claim 19, wherein the contact sensor is coupled to a sealing portion of the mask and distributed around a periphery of the mask.

24. The medication delivery system of claim 19, wherein the indicator is disposed on the mask.

25. The medication delivery system of claim 19, wherein the indicator is disposed on the medication delivery device.

* * * * *